(12) United States Patent
Asanoi

(10) Patent No.: US 10,195,377 B2
(45) Date of Patent: Feb. 5, 2019

(54) DEVICE FOR CALCULATING RESPIRATORY WAVEFORM INFORMATION AND MEDICAL INSTRUMENT USING RESPIRATORY WAVEFORM INFORMATION

(75) Inventor: Hidetsugu Asanoi, Imizu (JP)

(73) Assignees: Hidetsugu Asanoi, Imizu-shi, Toyama (JP); Teijin Pharma Limited, Tokyo (JP)

(*) Notice: Subject to any disclaimer, the term of this patent is extended or adjusted under 35 U.S.C. 154(b) by 950 days.

(21) Appl. No.: 13/388,414

(22) PCT Filed: Aug. 11, 2010

(86) PCT No.: PCT/JP2010/063892
§ 371 (c)(1),
(2), (4) Date: Feb. 1, 2012

(87) PCT Pub. No.: WO2011/019091
PCT Pub. Date: Feb. 17, 2011

(65) Prior Publication Data
US 2012/0125337 A1     May 24, 2012

(30) Foreign Application Priority Data
Aug. 13, 2009   (JP) .................................. 2009-187759

(51) Int. Cl.
*A61B 5/087* (2006.01)
*A61M 16/00* (2006.01)
(Continued)

(52) U.S. Cl.
CPC ............. *A61M 16/00* (2013.01); *A61B 5/087* (2013.01); *A61B 5/0816* (2013.01); *A61B 5/415* (2013.01);
(Continued)

(58) Field of Classification Search
CPC ....... A61B 5/0816; A61B 5/087; A61B 5/415; A61B 5/4812; A61B 5/4815;
(Continued)

(56) References Cited

U.S. PATENT DOCUMENTS 7,427,270 B2 * 9/2008 Izumi et al. .................. 600/534
2006/0070624 A1   4/2006 Kane et al.
(Continued)

FOREIGN PATENT DOCUMENTS

CN    101087559 A    12/2007
EP    1568314 A1     8/2005
(Continued)

OTHER PUBLICATIONS

Machine translation of JP 2009-078139 A from the JPO website. Oct. 7, 2014.*
(Continued)

*Primary Examiner* — Navin Natnithithadha
(74) *Attorney, Agent, or Firm* — Sughrue Mion, PLLC

(57) ABSTRACT

Provided is a configuration capable of executing a detection test for a comfort level including the quality of sleep, which is measurable at home without requiring the measurement of brain waves or electrocardiogram. The respiratory waveform of a subject during sleep is continuously measured and recorded from the respiratory gas flow, etc., and is window-Fourier transformed at each measurement time to generate a frequency spectrum, and a bandwidth including a respiratory frequency is extracted. The index indicating the regularity of the respiratory period of the subject is also calculated at each time point during the sleep, and the time-dependency of this index during the sleep is represented as a graph. A medical device includes a sleep evaluation system equipped with a control means for performing control so that a sleep cycle repeated at a cycle of about 90 minutes is clearly observed (Continued)

if the comfort level including the quality of sleep of the subject is favorable.

7 Claims, 40 Drawing Sheets

(51) Int. Cl.
| | | |
|---|---|---|
| *A61B 5/08* | (2006.01) | |
| *A61B 5/00* | (2006.01) | |
| *A61M 16/10* | (2006.01) | |
| *G06F 19/00* | (2018.01) | |

(52) U.S. Cl.
CPC .......... *A61B 5/4812* (2013.01); *A61B 5/4815* (2013.01); *A61B 5/7257* (2013.01); *A61M 16/026* (2017.08); *A61M 16/101* (2014.02); *G06F 19/00* (2013.01); *A61M 16/107* (2014.02); *A61M 2016/1025* (2013.01); *A61M 2202/0208* (2013.01); *A61M 2202/03* (2013.01)

(58) Field of Classification Search
CPC ... A61B 5/7257; A61M 16/00; A61M 16/101; A61M 2202/0208
See application file for complete search history.

(56) References Cited

U.S. PATENT DOCUMENTS

| | | | | |
|---|---|---|---|---|
| 2006/0169282 | A1* | 8/2006 | Izumi et al. | 128/204.23 |
| 2006/0247546 | A1 | 11/2006 | Imose | |
| 2007/0093724 | A1 | 4/2007 | Nakano | |
| 2008/0033306 | A1 | 2/2008 | Joeken | |
| 2009/0015842 | A1* | 1/2009 | Leitgeb et al. | 356/456 |
| 2009/0149718 | A1 | 6/2009 | Kim et al. | |
| 2010/0331715 | A1* | 12/2010 | Addison et al. | 600/529 |

FOREIGN PATENT DOCUMENTS

| | | |
|---|---|---|
| EP | 2 000 090 A2 | 12/2008 |
| JP | 07-275362 A | 10/1995 |
| JP | 2950038 B | 9/1999 |
| JP | 2002-071825 A | 3/2002 |
| JP | 2003-199831 A | 7/2003 |
| JP | 2003-310679 A | 11/2003 |
| JP | 2004-283194 A | 10/2004 |
| JP | 2004-305258 A | 11/2004 |
| JP | 2005-237569 A | 9/2005 |
| JP | 2005-270570 A | 10/2005 |
| JP | 3868326 B | 1/2007 |
| JP | 2007-068906 A | 3/2007 |
| JP | 2007-089716 A | 4/2007 |
| JP | 2008-532587 A | 8/2008 |
| JP | 2008-301951 A | 12/2008 |
| JP | 2009-078138 A | 4/2009 |
| JP | 2009078139 A * | 4/2009 |
| WO | 01/95971 A2 | 12/2001 |
| WO | 2006/133494 A1 | 12/2006 |
| WO | 2007/064682 A1 | 6/2007 |
| WO | 2008/046146 A1 | 4/2008 |
| WO | 2008/057884 A2 | 5/2008 |
| WO | 2008/138040 A1 | 11/2008 |
| WO | 2011/005376 A1 | 1/2011 |

OTHER PUBLICATIONS

Communication dated May 6, 2014, issued by the Intellectual Property Office of Singapore in corresponding Singapore Application No. 2012009478.
Miltos P. Vassiliou et al., "Respiratory mechanics determined by Fourier analysis in mechanically ventilated COPD and ARDS patients", Clinical Study, Pneumon No. 2, Apr.-Jun. 2007, vol. 20, pp. 187-193.
Extended European Search Report dated Dec. 11, 2014, issued by the European Patent Office in counterpart European application No. 10808269.4.
"Microwave Respiratory Sensor for Evaluation" (http://www3.ocn.ne.jp/~mwlhp/kokyu.PDF).
"Introduction to Digital Signal Processing" Kennichi Kido, pp. 13-15, (Jul. 20, 1985, Maruzen).
"What is Wavelet Transform" Michio Yamada, ("Mathematical Science," Dec. 1992, pp. 11-14, Saiensu-sha Co., Ltd.).
"Wavelet Analysis ~ Birth/Development/Application" Ryuichi Ashino, Shizuo Yamamoto, pp. 23-25 and 131-133 (Jun. 5, 1997, Kyoritsu Shuppan Co., Ltd.).
Hamlin RL, Smith CR and Smetzer DL. "Sinus Arrhythmia in the Dog" Am J Physiol 1966; 210, pp. 321-328.
Shykoff BE, Naqvi SJ, Menon AS and Slutsky AS. "Respiratory Sinus Arrhythmia in Dogs: Effects of Phasic Afferents and Chemostimulation" J Clin Invest 1991; 87: 1612-1627.
Tara BH, Simon PM, Dempsey JA, Skatrud JB and Iber C. "Respiratory Sinus Arrhythmia in Humans: An Obligatory Role for Vagal Feedback from the Lungs" J Appl Physiol 1995; 78: 638-645.
Kobe Kyodo Hospital—"Sleep Apnea Syndrome" (http://homepage3.nifty.com/SAS-kyo/titration.pdf#search="titration").
Kazuyuki Shimada, et al., Joint Research Report in 1998-1999 "Guideline Relating to Use Standard of 24-Hour Blood Pressure Meter (ABPM)" (Japanese Circulation Journal vol. 64, Suppl. V, 2000).
Tsugiyoshi Yamazaki, "Suiminji Mukokyu Shokogun to Ukketsusei Shinfuzen" Journal of Blood Pressure, (Jan. 11, 2005), vol. 12, No. 11, 2005, pp. 1177-1181.
Jun'ya Takakawa, "Shinfuzen to Suiminji Mukokyu Shokogun" Cardioangiology, (Oct. 28, 2007), vol. 26, No. 4, pp. 374-380.
Extended European Search Report dated Jul. 15, 2015 from the European Patent Office in counterpart European Application No. 10808269.4.

* cited by examiner

FIG. 2
(A)
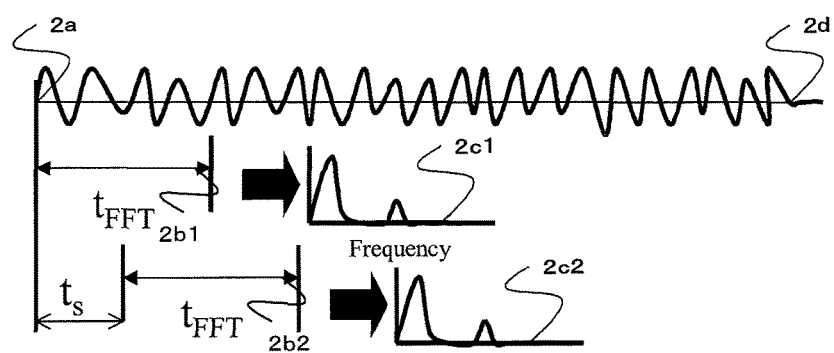
(B)
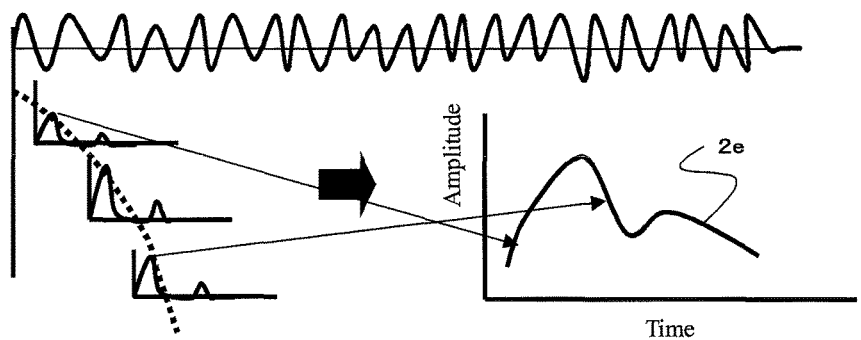

Noise waveform (noise) is created by subtracting smoothing respiratory waveform (smooth) from lower envelope (bottom) of respiratory sensor output waveform (resp4) obtained by moving average four measurements Conceptual diagram of fluctuation index (var) of respiratory cycle

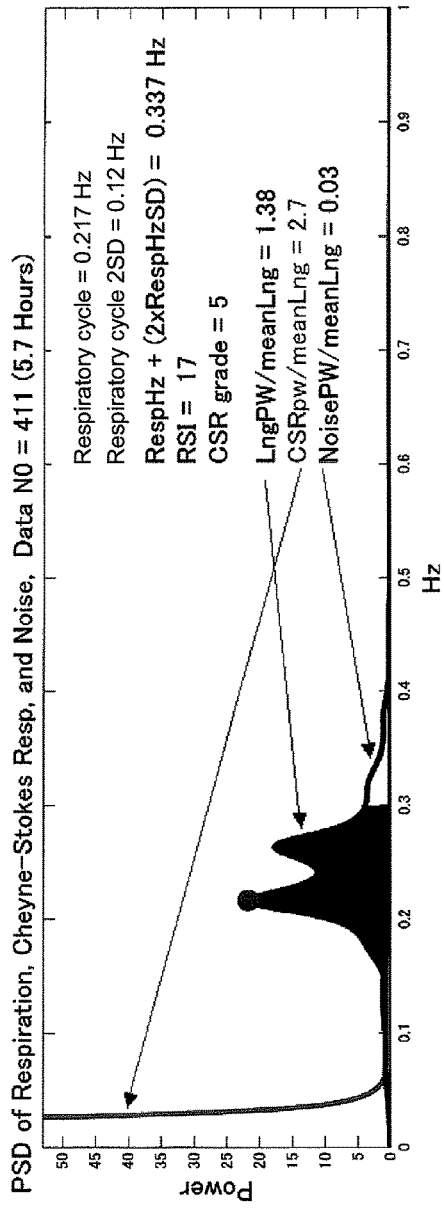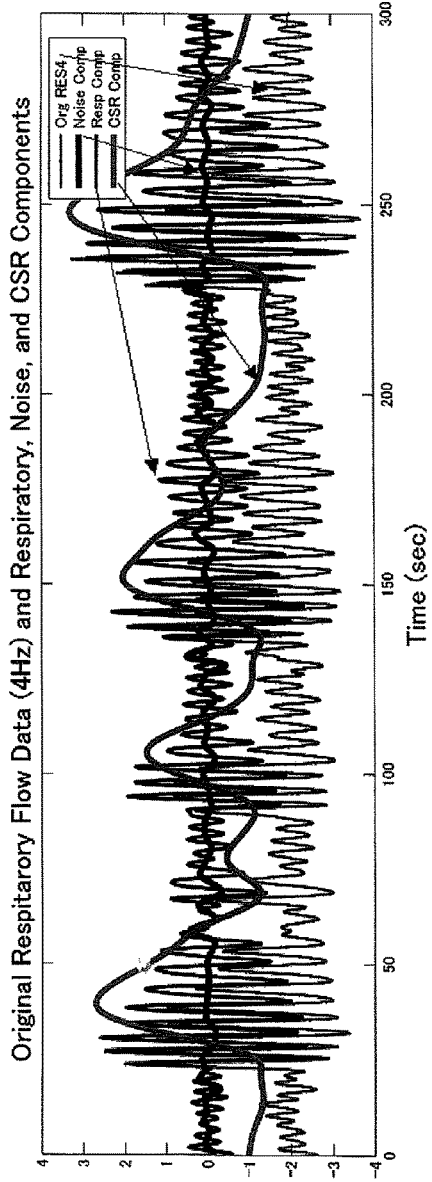
FIG. 11

First case (healthy person)

(iii) Frequency distribution of brain wave SWA and respiratory cycle RSI

Second case (NYHA I, BNP=47)   FIG. 18

(iii) Frequency distribution of brain wave SWA and respiratory cycle RSI

FIG. 21
Second case (NYHA I, BNP=47)
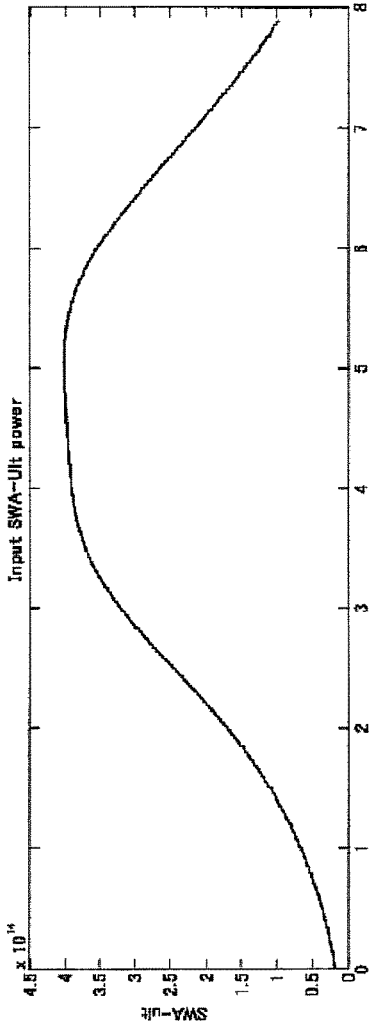
(xi) Change of ultradian power included in brain wave SWA trend
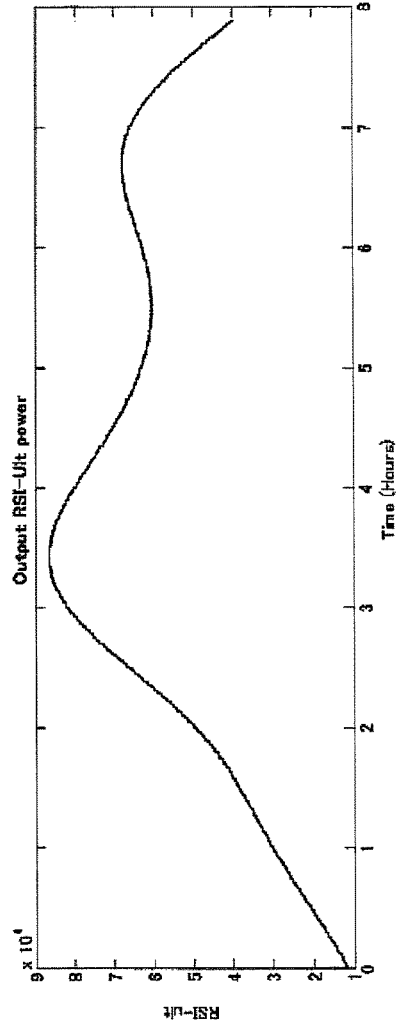
(xii) Change of ultradian power included in respiratory cycle RSI trend Fourth case (NYHA III, BNP=1000)

(vii) Brain wave SWA trend (viii) Trend of ultradian power included in brain wave SWA trend Fourth case (NYHA III, BNP=1000)

(xi) Change of ultradian power included in brain wave SWA trend (xii) Change of ultradian power included in respiratory cycle RSI trend

DEVICE FOR CALCULATING RESPIRATORY WAVEFORM INFORMATION AND MEDICAL INSTRUMENT USING RESPIRATORY WAVEFORM INFORMATION

CROSS REFERENCE TO RELATED APPLICATIONS

This application is a National Stage of International Application No. PCT/JP2010/063892 filed Aug. 11, 2010, claiming priority based on Japanese Patent Application No. 2009-187759, filed Aug. 13, 2009, the contents of all of which are incorporated herein by reference in their entirety.

TECHNICAL FIELD

The present invention relates to a device for calculating respiratory waveform information, a device which evaluates comfort level including a quality of sleep, a device for calculating physiological data, a computer program for calculation using the respiratory waveform information, a computer program for evaluating comfort level including the quality of sleep of a subject, a respiratory assisting device, a device for curing chronic cardiac diseases, a device for inspection to be used in titration, a blood-pressure testing device, a computer program for blood pressure test, a polysomnography testing device and the like and particularly provides a configuration which enables reliable evaluation of comfort level including a quality of sleep of a subject without requiring inpatient tests in a medical institution by simplifying and facilitating a prior-art configuration.

BACKGROUND ART

Evaluation of a quality of sleep, which is one of comfort levels of a subject, is important in diagnosis and medical treatment of various diseases.

Including a period of being awake, sleep of a human includes six stages, that is, an arousal period, a REM period (Rapid Eye Movement: sleep period during which eye movement is found), a NREM (non-REM) period, first stage (inclined sleep initial stage), a NREM period, second stage (inclined sleep stage), a NREM period, third stage (moderate sleep stage), and a NREM period, fourth stage (deep sleep stage).

In a normal sleep, when entering a sleep state from an arousal period, transition of a sleep state is repeated three cycles in one night, each cycle being 90 minutes typically or 60 to 120 minutes in general, called a sleep cycle (ultradian rhythm), and each cycle includes a part of or all of the above-described stages in the REM period and the NREM period, in which the depth of sleep cyclically (periodically) changes in each cycle and also changes with a tendency of gradually changing from a deep sleep state in the sleep initial stage to a light sleep in the whole sleep in one night.

Therefore, the level of comfort including the quality of sleep is evaluated on the basis of whether the cycle of sleep repeated in this ultradian rhythm is clearly found or in each cycle, whether cyclic sleep stage transition is clearly found in each cycle or whether the depth of sleep gradually changes from the sleep initial stage to a light end stage in the whole sleep in one night.

In a sleep with a non-favorable quality, the ultradian rhythm is not clear in the transition of the sleep state, and there can be a case in which a deep sleep stage is not found in the sleep initial stage but to the contrary, the deep sleep stage comes in the end stage, for example.

There are various diseases that cause obstruction in a good-quality sleep, and in OSAS (Obstructive sleep apnea syndrome), for example, a tongue part of a patient during sleep lowers by a gravitational force and physically blocks an airway, which obstructs respiration and causes arousal and prevents entry to a deep sleep stage.

Also, CSR (Cheyne-Stokes Respiration) considered to be found in approximately 40% of CHF (congestive heart failure) patients also causes a drop in the comfort level including the quality of sleep.

The CSR is respiration in which after a tidal volume gradually increases from small respiration, the tidal volume gradually decreases, and respiratory arrest (apnea for approximately 10 to 20 seconds) occurs and then, the similar cycle is repeated.

A factor to cause occurrence of CSR in the CHF patients is understood as follows.

The respiratory center of the brain executes respiratory control by detecting a $CO_2$ partial pressure in blood in a normal time. The CHF patient has high brain sensitivity to the $CO_2$ partial pressure while being awake and is in a hyperventilation state.

However, during sleep, this sensitivity is somewhat recovered and lowered, and thus, unless the $CO_2$ partial pressure in blood rises higher than in arousal (that is, apnea), respiration is not started, and the above-described CSR occurs.

The Cheyne-Stokes Respiration symptom is often observed in the CHF and is accompanied by sleep disorder caused by a nocturnal hypoxia state and arousal. The nocturnal hypoxia state and arousal cause an increase in a pulmonary artery pressure and sympathetic nerve activities, lowers exercise tolerance and deteriorates prognosis.

As described above, since the comfort level including the quality of sleep is lowered due to various diseases, it is necessary to evaluate the comfort level including the quality of sleep of a subject and to utilize the result for diagnosis and treatment.

First, a prior-art method of evaluating the comfort level including the quality of sleep will be described.

In the past, in order to evaluate the comfort level including the quality of sleep, the following sleep test using a device called PSG (Polysomnography) (hereinafter, this sleep test is called "PSG" or "PSG test") has been conducted in general. The PSG is a test in which a medical staff quantitatively evaluates the depth of sleep (sleep stage), fragmentation of sleep, presence of arousal reactions and the like by measuring respiratory flows, snoring sound, oxygen saturation in blood ($SpO_2$), brain waves, electromyograms, eye movement and the like over a sleep period of a subject.

The medical staff identifies the sleep cyclic period from a change in the brain waveform, for example, using the measurement result of the PSG and makes evaluations by means of a method such as discrimination between the REM period and the NREM period from the presence of eye movement and surface electromyography. These PSGs are disclosed in the following Patent Document 1 and Patent Document 2, for example.

Also, though it is different from the PSG, Patent Document 3 describes a method, as indicated in the paragraph 0023, in which respiratory data and motion data such as roll-over in each sleep stage of a subject are accumulated in advance by using the PSG and the current sleep stage is identified only from the respiratory data and the motion data in a test not using the PSG. Execution of the PSG is needed for creating initial data for identification, and identification accuracy is an important issue in the work of identification of the sleep stage from the measurement data . . .

Next, a prior-art technology relating to observation and detection of the Cheyne-Stokes respiration will be described.

In the detection of the Cheyne-Stokes respiration, the above-described PSG has been used in general. That is, the brain waves, eye movement, respiratory flows, ventilation motion by thoracoabdominal movement, arterial oxygen saturation, electrocardiogram (including heart rate) and the like are measured during the sleep period at night using PSG, and if gradual increase and gradual decrease of respiratory flows and respiratory efforts are found to occur repeatedly during the NREM sleep 1 to 2 (light sleep) from the measurement result report, the medical staff makes a diagnosis that occurrence of the Cheyne-Stokes respiration is suspected or the like.

With the purpose of simplified and reliable discovery of such Cheyne-Stokes respiration, Teijin Limited has proposed a biological information monitoring device with which a medical staff can observe the Cheyne-Stokes respiration symptom from an analysis result of the measurement result of an autonomic nerve alternation state on the basis of heart-rate alternation analysis and the measurement results of respiratory flows and respiratory efforts (ventilation motion), and the configuration is disclosed in Patent Document 4.

However, these prior-art technical configurations for detecting the Cheyne-Stokes respiration are all used such that the medical staff observes physiological data and detects the Cheyne-Stokes respiration. That is, though the Cheyne-Stokes respiration is recognized as an important risk factor in chronic heart failure, a configuration of automatically detecting occurrence of the Cheyne-Stokes respiration has not been proposed up to now.

CITATION LIST

Patent Document

Patent Document 1: Japanese Patent No. 2950038
Patent Document 2: Japanese Unexamined Patent Application Publication No. 2004-305258
Patent Document 3: Japanese Unexamined Patent Application Publication No. 2008-301951
Patent Document 4: Japanese Unexamined Patent Application Publication No. 2004-283194

SUMMARY OF INVENTION

Technical Problem

Since the PSG described above requires measurement of brain waves, the size of a device for PSG in use is large and needs to be installed in a medical institution and also, since high-level manipulation is required in attachment of an electrode for detecting brain waves to a subject, a professional engineer performs the attachment work and the subject to which the electrode was attached cannot move easily.

Thus, to take the PSG, a subject needs to be hospitalized in a dedicated medical institution or a dedicated test facility called sleep lab with a schedule of three days and two nights (the first night for PSG test and the second night for determination of prescription for treatment) and take tests in such medical institutions in many cases. The PSG, which is a test requiring overnight stay, needs hospitalization and preparation of sophisticated/complicated devices including a brain wave testing division and manipulation by professional engineers, and thus, a problem of increasing testing cost cannot be solved.

Also, with the technology disclosed in Patent Document 3, execution of the PSG is required for creating initial data for identification, and the work in which the device automatically executes identification of the sleep stage from the measurement data has a problem of validity and accuracy of the identification algorithm.

Moreover, if arrhythmia that is frequently found in CHF patients is included in the data, accurate evaluation is difficult.

Furthermore, there has been a technical problem that a work of identifying a peak from observation of an electrocardiogram waveform by a professional engineer is needed and attachment of an electrode for measurement of the electrocardiogram requires accuracy and skills, and thus, attachment of a testing device in a medical institution is necessary.

Also, in the prior-art technologies, a configuration in which a medical staff can observe a comfort level including the quality of sleep and occurrence of the Cheyne-Stokes respiration directly on the basis of physiological grounds only from the respiratory flow waveforms, which is important physiological data of a subject in sleep or a configuration of automatic evaluation or automatic extraction of them is not disclosed at all.

The present invention was made in view of the above circumstances and has an object to provide a device to be used for evaluating the comfort level including the quality of sleep reliably and simply without requiring inpatient tests and by using only the respiratory waveforms and for calculating the respiratory waveform information to be used in detecting the Cheyne-Stokes respiration symptom, a device for evaluating the comfort level including the quality of sleep, a device for calculating physiological data, a computer program for calculation by using the respiratory waveform information, a computer program for evaluating the comfort level including the quality of sleep of the subject, a respiratory assisting device, a device for treating chronic cardiac diseases, a testing device used for a titration work, a blood pressure testing device, a computer program for conducting a blood pressure test, and a polysomnography testing device.

Solution to Problem

The present invention provides, in order to solve the above problems, a device for calculating respiratory waveform information described in 1) to 42) below, a device for evaluating the comfort level including the quality of sleep, a device for calculating physiological data, a computer program for calculation by using the respiratory waveform information, a computer program for evaluating the comfort level including the quality of sleep of the subject, a respiratory assisting device, a device for treating chronic cardiac diseases, a testing device used for a titration work, a blood pressure testing device, a computer program for conducting a blood pressure test, and a polysomnography testing device.

1) A device for calculating respiratory waveform information, comprising (1) measuring means which measures a change in a respiratory flow of a subject for a predetermined measurement period including sleep; (2) calculating means which performs calculation including the following steps A to C with respect to the waveform of the respiratory flow measured by the measuring means; and (3) output means which executes at least any of processing of display, printing or sending to the outside the device of information of a calculation result calculated by the calculating means:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

2) A device for calculating respiratory waveform information, comprising (1) measuring means which measures a change in a respiratory flow of a subject for a predetermined measurement period; (2) calculating means which performs calculation including the following steps A to C with respect to the waveform of the respiratory flow measured by the measuring means; and (3) output means which executes at least any of processing of display, printing or sending to the outside of the device of information of a calculation result calculated by the calculating means:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

3) The device for calculating respiratory waveform information described in 1) or 2), wherein the index indicating the regularity of the respiratory cycle is configured as a value in inverse proportion to a standard deviation of respiratory frequency variation in a certain period.

4) The device for calculating respiratory waveform information described in any of 1) to 3), further comprising a step of creating at least any of information of (a) a waveform indicating a temporal change; (b) a maximum value; (c) an average value; and (d) time from start of sleep to time when the maximum value is reached of the power of ultradian rhythm included in the waveform indicating temporal change of the index indicating regularity of the respiratory cycle as information of a result of the calculation.

5) A device for calculating respiratory waveform information, wherein an operation performed by the measuring means in (1) described in any of 1) to 4) is performed by a respiratory waveform recording meter, and an operation performed by the calculating means in (2) and the output means in (3) described in any of 1) to 4) is performed by a respiratory waveform analyzing device on the basis of the waveform recorded in the respiratory waveform recording meter.

6) The device for calculating respiratory waveform information described in 5), wherein the information of the respiratory waveform recorded in the respiratory waveform recording meter is transmitted to the respiratory waveform analyzing device via a recording medium or a communication path.

7) A device for evaluating a comfort level including the quality of sleep, comprising (1) measuring means which measures a change in a respiratory flow of a subject for a predetermined measurement period including sleep; (2) calculating means which performs calculation including the following steps A to C with respect to the waveform of the respiratory flow measured by the measuring means; and (3) evaluating means which makes evaluation of the comfort level including the quality of sleep on the basis of the size of a numeral value of at least any one of (a) a maximum value; (b) an average value; and (c) time from start of the sleep to time when the maximum value is reached of power of ultradian rhythm included in the waveform indicating the temporal change of an index indicating regularity of the respiratory cycle obtained by the calculating means:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

8) A device for evaluating a comfort level including the quality of sleep, wherein an operation performed by the measuring means in (1) described in 7) is performed by a respiratory waveform recording meter, and an operation performed by the calculating means in (2) and the output means in (3) described in 7) is performed by a respiratory waveform analyzing device on the basis of the waveform recorded in the respiratory waveform recording meter.

9) The device for evaluating a comfort level including the quality of sleep described in 8), wherein the information of the respiratory waveform recorded in the respiratory waveform recording meter is transmitted to the respiratory waveform analyzing device via a recording medium or a communication path.

10) A device for calculating physiological data, comprising measuring means which measures physiological data of a subject for a predetermined measurement period; creating means which creates an index at each measurement time indicating stability of the measured value at each measurement time during the measurement period and creates data of a temporal change of the index during the measurement period; and output means which executes output processing of at least any one of display, printing or sending to the outside of the device of the created data.

11) A device for calculating physiological data, wherein that an operation performed by the measuring means described in 10) is performed by a physiological data recording meter and an operation performed by the creating means and the output means described in 10) is performed by a physiological data analyzing device on the basis of the waveform recorded in the physiological data recording meter.

12) The device for calculating physiological data described in 11), wherein the information of the physiological data recorded in the physiological data recording meter is transmitted to the physiological data analyzing device via a recording medium or a communication path.

13) A device for calculating respiratory waveform information, comprising at least (1) measuring means which measures a change in a respiratory flow of a subject for a predetermined measurement period including sleep; (2) calculating means which performs calculation including the following steps A and B with respect to the waveform of the respiratory flow measured by the measuring means; and (3) output means which executes at least any of output processing of display, printing or sending to the outside of the device of information of a calculation result calculated by the calculating means:

Step A: A step of creating a frequency spectrum at each time by sequentially executing window Fourier transform with a displaced start point at a predetermined displacement time interval with respect to the respiratory waveforms; and Step B: A step of extracting and creating a specific frequency domain power waveform of the respiratory flow waveform, which is waveform data of the power in a specific frequency domain changing over time, from a frequency spectrum at each time obtained in the Step A as information of the calculation result.

14) The device for calculating respiratory waveform information described in 13), wherein the specific frequency domain includes a respiratory frequency of a human body.

15) The device for calculating respiratory waveform information described in 13) or 14), wherein the specific frequency region includes an occurrence frequency of the Cheyne-Stokes respiratory symptom of a human body.

16) The device for calculating respiratory waveform information described in any of 13 to 15), wherein the calculating means further creates and outputs a waveform obtained by extracting a noise component caused by measurement performed by the measuring means from the waveform of the respiratory flow.

17) The device for calculating respiratory waveform information described in any one of 13) to 16), further comprising means for selecting arbitrary time in the measurement period from a specific frequency domain power waveform subjected to the output processing; and means for further creating (A) waveform information which enlarges the specific frequency domain power waveform in a neighboring region including the selected time and/or (B) information of the frequency spectrum in the neighboring region including the selected time as the information of the calculation result.

18) A device for calculating respiratory waveform information, wherein an operation performed by measuring means described in any of 13) to 17) is performed by a respiratory waveform recording meter, and an operation performed by the calculating means and the output means described in any of 13) to 17) is performed by a respiratory waveform analyzing device on the basis of the waveform recorded in the respiratory waveform recording meter.

19) The device for calculating respiratory waveform information described in 18), wherein the information of the respiratory waveform recorded in the respiratory waveform recording meter is transmitted to the respiratory waveform analyzing device via a recording medium or a communication path.

20) A computer program for performing calculation using respiratory waveform information, comprising (1) a measurement step in which measuring means measures a in a respiratory flow of a subject for a predetermined measurement period including sleep; (2) a calculation step in which calculating means performs calculation including the following steps A to C with respect to the waveform of the respiratory flow measured by the measurement step; and (3) an output step in which output means executes at least any of processing of display, printing or sending to the outside of the device of information of a calculation result calculated by the calculating means:

Step A: A step of creating a frequency spectrum at each time by sequentially executing window Fourier transform with a displaced start point at a predetermined displacement time interval with respect to the respiratory waveforms; and Step B: A step of creating an index indicating regularity of a respiratory cycle of the subject in the Fourier window time at the respective times; and Step C: A step of creating the waveform information indicating a temporal change of the index as the information of the calculation result.

21) The computer program for performing calculation using respiratory waveform information described in 20), wherein the calculation step executes the calculation, further comprising a step of creating information of at least any one of (a) a waveform indicating a temporal change; (b) a maximum value; (c) an average value; and (d) time from start of the sleep to time when the maximum value is reached of power of ultradian rhythm included in the waveform indicating the temporal change of an index indicating regularity of the respiratory cycle.

22) A computer program to be executed for evaluating a comfort level including the quality of sleep of a subject, comprising (1) a measurement step in which measuring means measures a change in a respiratory flow of the subject for a predetermined measurement period including sleep; (2) a calculation step in which calculating means performs calculation including the following steps A to C with respect to the waveform of the respiratory flow measured in measurement step; and (3) an evaluation step in which evaluating means makes evaluation of the comfort level including the quality of sleep on the basis of the size of a numeral value of at least any of (a) a maximum value; (b) an average value; and (c) time from start of the sleep to time when the maximum value is reached of power of ultradian rhythm included in the waveform indicating the temporal change of an index indicating regularity of the respiratory cycle obtained by the calculating step:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

23) A computer program for performing calculation using respiratory waveform information, comprising at least (1) a measurement step in which measuring means measures a change in a respiratory flow of a subject for a predetermined measurement period including sleep; (2) a calculation step in which calculating means performs calculation including the following steps A and B with respect to the waveform of the respiratory flow measured by the measurement step; and (3) an output step in which output means executes at least any of output processing of display, printing or sending to the outside of the device of the information of a calculation result calculated by the calculating means:

Step A: A step of creating a frequency spectrum at each time by sequentially executing window Fourier transform with a displaced start point at a predetermined displacement time interval with respect to the respiratory waveforms; and Step B: A step of extracting and creating a specific frequency domain power waveform of the respiratory flow waveform, which is waveform data of a temporal change of the power in a specific frequency domain of the following (A) or (B), and/or the extracted waveform of the following (C) from a frequency spectrum at each time obtained in Step A as information of the calculation result:

(A) A frequency band including a respiratory frequency of a body;

(B) A frequency band including a generation frequency of the Cheyne-Stokes respiration of a human body;

(C) A waveform obtained by extracting a noise component caused by measurement executed in the measurement step from the respiratory waveform.

24) A respiratory assisting device, comprising compressed air feeding means configured to feed out compressed air with a pressure higher than the atmospheric pressure and capable of changing the feeding-out pressure; duct means connected to the feeding-out side of the compressed air feeding means; and mask means provided on the other end part of the duct means and attached to a patient for treatment for supplying the compressed air to the patient, the respiratory assisting device continuously supplying the compressed air to the patient in a sleep state through the mask means, further comprising:

(1) biological information obtaining means which continuously obtains biological information of the patient to whom the compressed air is supplied; and (2) control means which changes and controls the feeding-out pressure of the compressed air feeding means to a direction to improve the comfort level including the quality of sleep of the patient by using the biological information obtained as above, wherein the biological information is information relating to the respiratory waveform of the patient, and the control means executes change and control of the feeding-out pressure on the basis of a temporal change of an index indicating regularity of a respiratory cycle of the subject, the respiratory cycle having been continuously obtained.

25) A device for treating chronic cardiac diseases, comprising compressed air feeding means configured to feed out compressed air with a pressure higher than the atmospheric pressure and capable of changing the feeding-out pressure; duct means connected to the feeding-out side of the compressed air feeding means; and mask means provided on the other end part of the duct means and attached to a patient for treatment for supplying the compressed air to the patient, the device being configured to continuously supply the compressed air to the patient in a sleep state through the mask means, further comprising:

(1) biological information obtaining means which continuously obtains biological information of the patient to whom the compressed air is supplied; and (2) control means which changes and controls the feeding-out pressure of the compressed air feeding means to a direction to improve the comfort level including the quality of sleep of the patient by using the biological information obtained as above, in which the biological information is information relating to the respiratory waveform of the patient, and the control means executes change and control of the feeding-out pressure on the basis of a temporal change of an index indicating regularity of a respiratory cycle of the subject, the respiratory cycle having been continuously obtained.

26) The device described in 24) or 25), wherein the compressed air feeding means is configured to automatically change and control the feeding-out pressure so that the pulmonary ventilation of the treatment patient and/or a respiratory frequency of the treatment patient gets close to a certain quantity set in advance.

27) A device wherein the operation performed by the biological information obtaining means of (1) described in any one of 24) to 26) is performed by a respiratory waveform recording meter and the operation performed by the control means of (2) described in any one of 24) to 26) is performed by a device for changing/controlling a feeding-out pressure on the basis of the waveform recorded in the respiratory waveform recording meter.

28) The device described in 27), wherein the information of the respiratory waveform recorded in the respiratory waveform recording meter is transmitted to the device for changing/controlling a feeding-out pressure through a recording medium or a communication path.

29) A testing device used in a titration work, comprising a respiratory assisting device provided with compressed air feeding means which feeds out compressed air with a pressure higher than the atmospheric pressure, duct means connected to the feeding-out side of the compressed air feeding means, and mask means provided on the other end part of the duct means and attached to a treatment patient for supplying the compressed air to the patient, the respiratory assisting device being configured to continuously supply the compressed air to the patient through the mask means at a constant pressure or a variable pressure, wherein a medical staff determines at least any one of (1) a pressure value of the compressed air; (2) a change pattern of the pressure value of the compressed air; and (3) selection from plurality of the respiratory assisting devices so as to be suitable for the treatment, further comprising:

detecting means which continuously detects the respiratory waveform information of the treatment patient; calculating means which calculates an index indicating regularity of the respiratory cycle of the patient from the respiratory information; and output means which performs at least any one of display, printing, and output to the outside so that a temporal change of the pressure of the compressed air and a temporal change of the index indicating the regularity of the respiratory cycle can be observed simultaneously.

30) A testing device used in a titration work, wherein the operation performed by the detecting means described in 29) is performed by a respiratory waveform recording meter, and the operation performed by the calculating means and the output means described in 29) is performed by a respiratory waveform analyzing device on the basis of the waveform recorded in the respiratory waveform recording meter.

31) The testing device used in a titration work described in 30), wherein the information of the respiratory waveform recorded in the respiratory waveform recording meter is transmitted to the respiratory waveform analyzing device through a recording medium or a communication path.

32) A blood-pressure detecting device, comprising (1) respiratory flow measuring means which measures a change of the respiratory flow of a subject for a first predetermined measurement period; (2) calculating means which performs calculation including the following steps A to C with respect to the waveform of the respiratory flow measured by the respiratory flow measuring means and outputs the result as information; (3) blood-pressure value measuring means which measures a temporal change of a blood pressure value of the subject for a second predetermined measurement period having a period matched with the first predetermined period; and (4) output means which performs at least any of processing of display, printing or sending to the outside of the device of the information of the outputted calculation result and the information of the trend of the measured blood pressure value in a mode capable of comparison with each other:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

33) The blood-pressure testing device described in 32), wherein the first predetermined measurement period and/or the second predetermined measurement period is configured so as to include a period during sleep of the subject.

34) A blood-pressure testing device, wherein the operation performed by the respiratory flow measuring means described in 32) or 33) is performed by a respiratory waveform recording meter, and/or the operation performed by the blood-pressure value measuring means is performed by a blood-pressure value recording meter, and the operation performed by the calculating means and the output means described in 32) or 33) is performed by an analyzing device on the basis of the waveform recorded in the respiratory waveform recording meter and/or the value recorded in the blood-pressure value recording meter.

35) The blood-pressure testing device described in 34), wherein the information of the respiratory waveform recorded in the respiratory waveform recording meter and/or the blood pressure value recorded in the blood-pressure value recording meter is transmitted to the analyzing device through a recording medium or a communication path.

36) A blood-pressure testing device, comprising (1) blood-pressure value measuring means which measures and obtains a blood pressure value of a subject in accordance with an obtainment command; (2) respiratory flow measuring means which measures a temporal change of the respiratory flow of the subject; (3) calculating means which performs calculation including the following steps A to C with respect to the waveform of the respiratory flow measured by the respiratory flow measuring means; and (4) obtainment command creating means which creates the obtainment command if an index indicating regularity of a respiratory cycle described in the following step B included in the information calculated by the calculating means exceeds a threshold value set in advance:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

37) The blood-pressure testing device described in any of 32) to 36), wherein the index indicating the regularity of the respiratory cycle is configured as a value in inverse proportion to a standard deviation of respiratory frequency variation in a certain period.

38) A computer program for performing a blood pressure test, comprising (1) a step in which respiratory flow measuring means measures a change in a respiratory flow of a subject for a first predetermined measurement period; (2) a step in which calculating means performs calculation including the following steps A to C with respect to the waveform of the respiratory flow measured by the respiratory flow measuring means; (3) a step in which blood-pressure measuring means measures a change of a blood pressure value of the subject for a second predetermined measurement period having a period matched with the first predetermined period; and (4) a step in which output means performs at least any of processing of display, printing or sending to the outside of the device of the information of the calculated calculation result and the information of the change of the measured blood pressure value in a mode capable of comparison with each other:

Step A: A step of creating a frequency spectrum at each time by sequentially executing window Fourier transform with a displaced start point at a predetermined displacement time interval with respect to the respiratory waveforms;

Step B: A step of creating an index indicating regularity of a respiratory cycle of the subject in the Fourier window time at the respective times; and Step C: A step of creating the waveform information indicating a temporal change of the index as the information of the calculation result.

39) A computer program for performing a blood pressure test of 38), wherein the index indicating the regularity of the respiratory cycle is configured as a value in inverse proportion to a standard deviation of respiratory frequency variation in a certain period.

40) A polysomnography testing device comprising measuring means which measures a blood pressure value of a subject.

41) A blood-pressure testing device comprising (1) measuring means which measures a change of a single piece of or a plurality of physiological data of a subject for a first predetermined measurement period including sleep; (2) determining means which continuously determines whether or not the subject is in a slow-wave sleep state at each measurement time on the basis of the physiological data measured by the measuring means; (3) blood-pressure value measuring means which measures a change of the blood pressure value of the subject for a second predetermined measurement period having a period matched with the first predetermined measurement period; and (4) output means which performs at least any of processing of display, printing or sending to the outside of the device of the information of the determination result and the information of the change of the measured blood pressure value in a mode capable of comparison with each other.

42) A blood-pressure testing device, comprising (1) blood-pressure value measuring means which measures and obtains a blood pressure value of a subject in accordance with an obtainment command; (2) measuring means which measures a change of a single piece of or a plurality of physiological data of the subject; (3) determining means which continuously determines whether or not the subject is in a slow-wave sleep state at each measurement time on the basis of the physiological data measured by the measuring means; and (4) obtainment command creating means which creates the obtainment command if the determining means determines that the subject is in the slow-wave sleep state.

43) An oxygen supply device for supplying oxygen gas for suction or oxygen concentrated gas for suction, comprising (1) biological information obtaining means which continuously obtains biological information of a target patient to whom the gas is supplied; and (2) control means which changes and controls a supply flow of the gas in a direction to improve the comfort level of the patient by using the obtained biological information.

44) The oxygen supply device described in 43), wherein that the biological information is information relating to a respiratory waveform of the patient, and the control means executes control of the supply flow on the basis of the information of respiratory cycle stability obtained from the information relating to this respiratory waveform.

45) The oxygen supply device described in 44), further comprising respiratory synchronization means which executes control of supply of the gas in accordance with inspired air of a user on the basis of a signal of a sensor which detects a state of at least either of inspired air or expired air of the patient, wherein the control means obtains the information relating to the respiratory waveform on the basis of the signal of the sensor.

46) The oxygen supply device described in any one of 43) to 45), wherein a supply source of the gas is any of the following (A) to (D) provided inside or outside the device:

(A) Means which separates oxygen in the air and creates the oxygen concentrated gas;

(B) A high-pressure gas container which compresses and stores the oxygen gas and discharges it in accordance with an operation;

(C) A liquid oxygen container which stores the liquefied oxygen gas and discharges it as oxygen gas in accordance with the operation; and (D) Piping means having one end connected to the high-pressure gas container and the other end to the oxygen supply device.

47) A testing system, comprising sensor means which detects a state of inspired air and/or expired air of a subject; first creating means which creates respiratory waveform information of the subject on the basis of an output signal of the sensor means; and second creating means which creates information of respiratory cycle stability from the created respiratory waveform information.

48) A patient monitoring system, comprising sensor means which detects a state of inspired air and/or expired air of a subject; first creating means which creates respiratory waveform information of the subject on the basis of an output signal of the sensor means; second creating means which creates information of respiratory cycle stability from the created respiratory waveform information; and transmission means and reception means which transmits/receives the respiratory waveform information and/or the respiratory cycle stability information through a communication path.

49) A medical equipment system, comprising a medical equipment installed in a patient's home or a medical institution; and a transmission terminal connected to or incorporated in the medical equipment, the transmission terminal obtaining information from the medical equipment and transmitting it to a reception terminal installed in a place away from the medical equipment through a communication medium, wherein the transmitted information includes respiratory waveform information obtained by detecting the state of inspired air and/or expired air of the patient on the basis of an output signal of sensor means incorporated in or provided separately from the medical equipment and/or information of respiratory cycle stability obtained from the respiratory waveform information created as above.

50) The medical equipment system described in 49, wherein the transmitted information further includes operation information of the medical equipment.

Each of the above-described configurations can be combined with each other as long as it does not depart from the gist for the present invention.

Advantages of the Invention

The present invention with the above configuration exerts marked advantages of providing a device which calculates respiratory waveform information used for evaluating a comfort level including the quality of sleep and detecting the Cheyne-Stokes respiration symptoms reliably and simply without requiring inpatient test and by using only the respiratory waveforms, a device which evaluates a comfort level including the quality of sleep, a device for calculating physiological data, a computer program for performing calculation by using the respiratory waveform information, a computer program for evaluating the comfort level including the quality of sleep of a subject, a respiratory assisting device, a device for treatment of chronic cardiac diseases, a testing device used in a titration work, a blood-pressure testing device, a computer program for a blood pressure test, and a polysomnography testing device.

BRIEF DESCRIPTION OF THE DRAWINGS

FIG. 2 is a schematic diagram illustrating a principle when the system in FIG. 1 performs measurement.

FIG. 11 is an example of each waveform frequency spectral graph in a selected time domain created by the system in FIG. 1.

FIG. 21 is each index graph of the second case.

BEST MODE FOR CARRYING OUT THE INVENTION

An optimal configuration according to an embodiment of the present invention, which is a sleep evaluation system on the basis of a respiratory waveform (hereinafter also referred to as this system or the sleep evaluation system), will be described below by referring to the attached drawings.

A sleep evaluating device of this embodiment has a main object to create and output waveform information on the basis of a respiratory waveform of a subject so that a medical staff makes a diagnosis on the basis of this waveform information.

Also, in the following description, including each variation, a sleep evaluating device as one embodiment specialized in the purpose of analysis of the respiratory waveform is focused, but technical features and advantages disclosed here are not limited to the purpose of analysis of the respiratory waveform. It is possible to use the device for analysis of other physiological data of a human body, and apart from a measured value as a cycle of the respiratory waveform in the following description, the configuration of this embodiment can be also applied to a cycle or amplitude and other measured values of other physiological data. The specific configurations of those applied configurations can be sufficiently understood from the description of this embodiment.

Also, although the configuration in which the physiological data of a subject during sleep is used is the most important when a state of the body of a subject is observed by using the physiological data such as a respiratory waveform, when the device makes an automatic evaluation, or when a medical equipment or the like is automatically controlled by using the result of the automatic evaluation, it is only one exemplification in various embodiments. Even if the physiological data of a subject in an arousal state is used during daytime or at night, the advantages specific to the present invention illustrated in each of the embodiments below can be shown.

[Configuration of Sleep Evaluating Device on the Basis of Respiratory Waveform]

Figure 1:
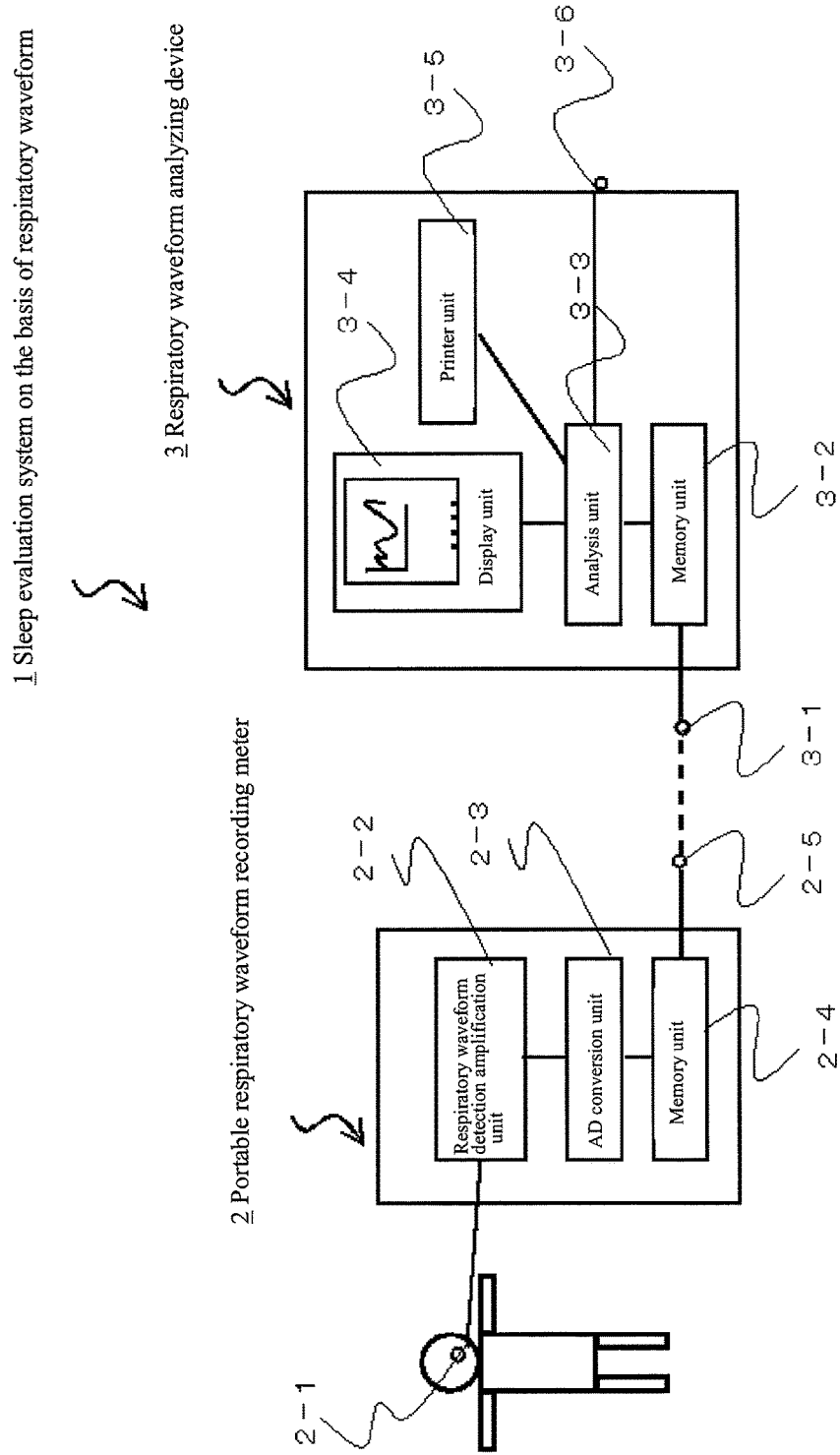
FIG. 1 is a configuration diagram of a sleep evaluation system on the basis of respiratory waveform according to the present invention.

This sleep evaluation system 1 is, as illustrated in a configuration diagram in FIG. 1, provided with a portable respiratory waveform recording meter 2 and a respiratory waveform analyzing device 3.

The portable respiratory waveform recording meter 2 is a portable device which can record a respiratory waveform, and it is preferable that the device is typically lent by a medical institution to a subject so that the subject can continuously record and hold a recorded waveform in one night sleep at home and then, the device is transported to the medical institution. For example, a biological information monitor "Morpheus (registered trademark) R set" (marketing authorization holder Teijin Pharma Limited, medical equipment authorization No. 21300BZY00123000, management medical equipment class, specified maintenance and management medical equipment) employs a pressure sensor (nasal cannula) for detection of an airflow/snoring and configured to finely detect apnea, hypopnea, and snoring, and this equipment may be used.

It is needless to say that the recording of the respiratory waveform may be performed in a medical institution and data of the recorded waveform may be recorded in a recording medium such as a flash memory, a magnetic disk, an optical disk and the like and transported or transmitted via a communication path to a device which conducts analysis. The communication path includes the Internet communication network, a dedicated communication line, a dial-up telephone line and the like, whether it is wired or wireless.

In order to realize the above functions, the portable respiratory waveform recording meter 2 has a respiratory airflow sensor 2-1 to be attached to the skin surface in the vicinity of the nasal cavity of the subject, a respiratory waveform detection amplification unit 2-2, an A/D conversion unit 2-3, a memory unit 2-4 which records and holds the respiratory waveform as a digital signal, and an output terminal 2-5 which outputs the digital respiratory waveform data from the memory unit t 2-4 to the outside.

The respiratory airflow sensor 2-1 is a thermal sensor attached to the vicinity of the nasal cavity of the subject and discriminates the temperature of a respiratory airflow from the temperature of the other outside air, for example, and measures and detects the temperature of the respirator airflow so as to measure presence and intensity of the airflow by respiration of this subject.

As a configuration for measuring the respiratory airflow of a subject, a resistance change method based on deformation of a strip-shaped member due to a respiratory airflow, a configuration of a wind-mill structure using rotation by the airflow and the like can be used other than the thermal sensor as long as presence and intensity of the respiratory airflow can be detected.

Particularly, use of a pressure-sensing respiratory sensor provided with a PVDF (polyvinylidene fluoride) piezoelectric film is a preferable mode as a pressure sensor which detects respiration.

Moreover, the respiratory operation (ventilation motion) of the subject may be measured and recorded not by directly measuring the respiratory airflow but by measuring tension caused by extension of a band wrapped around the chest or stomach of the subject by the respiratory motion or by providing a pressure-sensing sensor in a mat laid under the subject.

These various respiratory sensors are attached to a predetermined part of a patient in order to detect the respiratory airflow of the patient or respiratory efforts (ventilation motion) of the patient, and the medical institution should give guidance on the attachment method in advance to the patient prior to the test. However, as compared with attachment of an electrode for measurement of electrocardiogram at a specific position on the epidermis on the chest of the patient, allowance in the position, direction and the like to attach the respiratory sensor is larger than the case of a sensor for electrocardiogram, and it is easy for a patient or the patient's family to attach the sensor in compliance with the guidance by the medical institution and to obtain a correct measured value.

Moreover, in recent years, instead of detection of a respiratory operation by attaching some sensing means to a subject as above, many types of a non-contact respiratory sensor have been proposed which emits electromagnetic waves to the subject from a distant position and detects the body motion or respiratory operation of the subject by analyzing reflection waves.

For example, in a document "Microwave respiratory sensor for evaluation", which is posted on the World Wide Web and can be accessed (http://www3.ocn.ne.jp/mwlhp/kokyu.PDF), a non-contact respiratory sensor using microwave is disclosed, describing in its configuration, principle, and advantages as "weak microwave impulses are emitted to a subject from a high-gain directional antenna. The microwave impulses reflected on the skin surface of the subject through the bedding and clothes are received as a micromotion reflection signal by a highly sensitive receiver for a gate time. By specifying a detection space by sharp antenna directivity and a distance gate reception, higher sensitivity of the micro-motion sensor can be realized without being affected by disturbance. A demonstration device for evaluation has a detection distance of approximately 2 m and a circle with a diameter of approximately 60 cm, but an oval detection surface which covers a bed width can be realized by antenna design.", "since this is a microwave micromotion sensor accepted for obtaining micro-radio standard not requiring qualification, there is no problem of obtaining license and the like for merchandizing. The radiation electric field intensity of the micro-radio microwave is not more than the electric field intensity of satellite broadcasting and does no harm human bodies. Non-contact detection of the micromotion on the skin surface can be made without being affected by beddings or clothes, and no burden is applied to the subject. By using a ceiling material such as a plaster board with less passage loss of the microwaves, the device can be installed above the ceiling, and no psychological burden is applied to the subject. As compared with a Doppler-type micro-motion detection method, higher sensitivity can be realized without being affected by the disturbance by specifying the detection distance and the detection range, and no mutual interference occurs even if a plurality of devices are installed in proximity."

Similarly, Japanese Unexamined Patent Application Publication No. 2002-71825, which is a known document, and titled as "human body detecting device using microwave", discloses a human body detecting device using microwave, using a microwave as a transmission wave in life scenes such as in a toilet, a washroom, a kitchen, a bathroom, a shower room and the like, comprising a single antenna which receives the microwave, detecting means which detects the microwave received by the antenna, comparing means which compares an output of change component detecting means with a predetermined position, and means for detecting presence of a human and biological information of a human by a signal from the comparing means, the human body detecting device using a microwave described above, wherein the detecting means is provided with a Doppler sensor which detects Doppler shift of a reflection wave to the transmission, the human body detecting device using a microwave described above, wherein the signals obtained by the detecting means and the comparing means are signals synchronized with pulses of a human, and the human body detecting device using a microwave described above, wherein the signals obtained by the detecting means and the comparing means are signals synchronized with a respiratory operation of a human.

Figure 7:
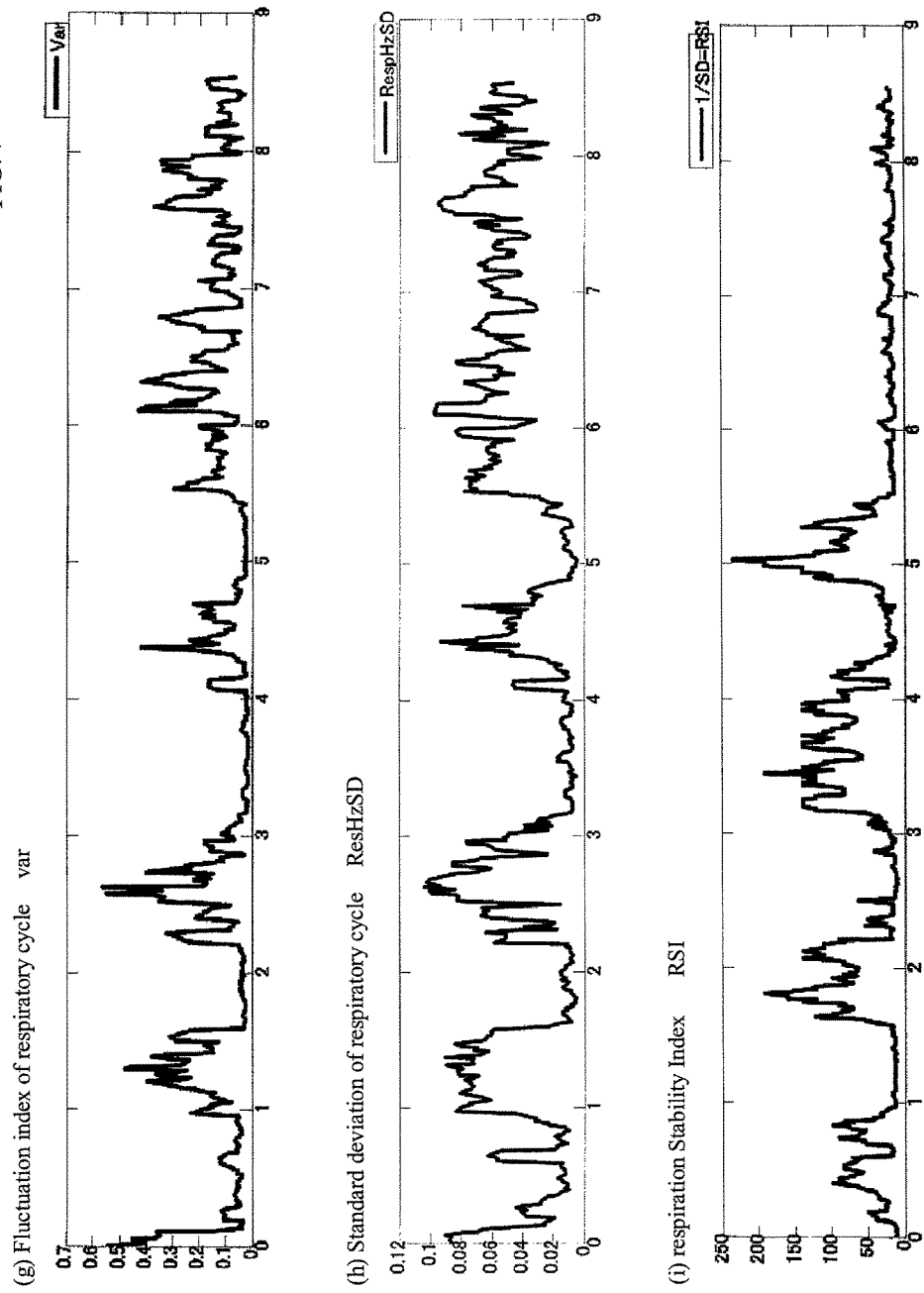
FIG. 7 is a waveform diagram illustrating a temporal change of a plurality of indexes created by using the system in FIG. 1.

Similarly, Japanese Unexamined Patent Application Publication No. 2005-237569, which is a known document and titled as "portable measuring device, health management system and health management method", discloses that "a transmission unit 11*a* of a microwave Doppler sensor 10*a* illustrated in FIG. 2 transmits a microwave toward a user Pa (See FIG. 1). Here, the transmission unit 11*a* transmits the microwave toward the vicinity of the heart of the user Pa (See FIG. 1). The microwave has properties being transmitted through cotton or nylon, which is material of clothes of the user Pa (See FIG. 1) and reflected by the body surface and metal. A receiving unit 12*a* receives a reflection wave. Here, the reflection wave is the microwave reflected on the body surface in the vicinity of the heart of the user Pa (See FIG. 1). An amplification unit 15*a* receives the signal of the microwave from the transmission unit 11*a*. The amplification unit 15*a* receives the signal of the reflection wave from the receiving unit 12*a*. The amplification unit 15*a* amplifies the signal of the microwave and the signal of the reflection wave. A calculation unit 16*a* receives a signal relating to the microwave from the amplification unit 15*a* via a processing unit 13*a*. Here, the signal relating to the microwave is a signal obtained by amplifying the signal of the microwave. The calculation unit 16*a* receives a signal relating to the reflection wave from the amplification unit 15*a* via the processing unit 13*a*. Here, the signal relating to the reflection wave is a signal obtained by amplifying the signal of the reflection wave. The calculation unit 16*a* calculates change information (See FIG. 7). The change information (See FIG. 7) is information relating to a change of the signal relating to the reflection wave with respect to the signal relating to the microwave. An extraction unit 14*a* receives the change information (See FIG. 7) from the calculation unit 16*a* via the processing unit 13*a*. The extraction unit 14*a* extracts band information on the basis of the change information (See FIG. 7). The band information is information of a predetermined frequency band (See P1 to P4 in FIG. 7). An analysis unit 17*a* receives the band information (See P1 to P4 in FIG. 7) from the extraction unit 14*a* via the processing unit 13*a*. The analysis unit 17*a* analyzes micro body motion by heart rate of the user Pa (See FIG. 1) on the basis of the band information (See P1 to P4 in FIG. 7). As a result, the analysis part 17*a* analyzes heart rate information (See FIG. 8) on the basis of the band information (See P1 to P4 in FIG. 7). Here, the heart rate information (See FIG. 8) is information relating to a stress degree. A determination unit 18*a* receives the heart rate information (See FIG. 8) from the analysis unit 17*a* via the processing unit 13*a*. The determination unit 18*a* determines abnormality of the user Pa (See FIG. 1) on the basis of the heart rate information (See FIG. 8). If the determination unit 18*a* determines that the user Pa (See FIG. 1) has abnormality, the processing unit 13*a* receives the heart rate information (See FIG. 8) from the analysis unit 17*a* and delivers it to an output device 20*a*. Along with that, the processing unit 13*a* refers to a storage device 40*a*, receives identification information 41*a* from the storage device 40*a* and delivers the identification information 41*a* to the output device 20*a*. If the determination unit 18*a* determines that the user Pa (See FIG. 1) does not have abnormality, the processing unit 13*a* does not deliver any information to the output device 20*a*. A transmission output unit 21*a* of the output device 20*a* receives the heart rate information (See FIG. 8) and the identification information 41*a* from the microwave Doppler sensor 10*a*. The transmission output unit 21*a* transmits the heart rate information (See FIG. 8) and the identification information 41*a* to a management center 60 via a wireless telephone line. The other mobile phones 50b, . . . are similar to a mobile phone 50a.", and the respiration may be detected by a respiratory operation instead of the heart rate operation by using this configuration.

Similarly, Japanese Unexamined Patent Application Publication No. 2005-270570, which is a known document and titled as "biological information monitoring device", discloses "a device which monitors information of a living body by obtaining of information of surface displacement of the living body in a non-contact manner, comprising means which generates high-frequency electromagnetic waves and radiates the same into the space, means which detects the electromagnetic waves scattered on the surface of the living body, and means which calculates temporal fluctuation of positional displacement on the living body surface from a propagation state of the electromagnetic waves, further comprising means which calculates characteristic amounts of vibration such as pulsation, respiration and the like from the temporal fluctuation as biological information, the biological information monitoring device described above, wherein the biological information is obtained from pulsation, pulse wave, respiration, electrocardiographic wave, blood pressure or analysis of them, the biological information monitoring device described above, wherein the high-frequency electromagnetic waves are millimeter waves to terahertz band (30 GHz to 30 THz) and information on the living body surface is obtained through clothes made of organic fibers or the like, the biological information monitoring device described in any of the above, wherein the high-frequency electromagnetic waves are short pulses repeatedly generated and a half bandwidth of the pulse is 33 psec or less, the biological information monitoring device described above, wherein the temporal fluctuation of positional displacement at plural spots on the living body is calculated simultaneously by means which calculates the temporal fluctuation of positional displacement on the living body surface by the electromagnetic waves and a state of propagation of the characteristic amount calculated from the temporal fluctuation through the living body can be detected, the biological information monitoring device described above, further comprising storage means, wherein mental and physical states of a living body are determined by using the characteristic amount stored in advance, the characteristic amount in which an output signal obtained from the means which calculates the biological information is continuously stored, and an actual signal outputted from the means which calculates biological information, the biological information monitoring device described above, wherein the mental and physical states to be determined are a health state such as blood pressure, arterial sclerosis degree and the like obtained from the vibration analysis of pulsation and the vibration analysis of respiration and the determination result is directly displayed in letters or sound or presented on a terminal via a network, the biological information monitoring device described above, wherein the mental and physical states to be determined are an emotional state such as relaxation degree, stress degree, emotions and the like obtained by pulsation analysis of pulses and pulsation analysis of respiration, and the determination result is fed back to a mechanical device or an electronic device so as to be used as a control signal of an interface which operates the mechanical device or the electronic device, and the biological information monitoring device described above, wherein the biological information monitoring device is incorporated in a spot such as a washing basin, a toilet, a chair or the like where a human stays for a certain period of time and biological information is obtained remotely in a non-attached manner at the spot." Thus, these configurations may be used. Inclusion of the configurations using the non-contact respiratory sensor in the scope of the present invention applies to all the examples.

The respiratory waveform analyzing device 3 similarly constituting this sleep evaluation system 1 is realized by a personal computer system typically including a display screen or a printer and a computer program installed in the computer for performing the operation, and the device is installed in a medical institution or the like, to which the portable respiratory waveform recording meter 2 for which obtainment of the respiratory waveform from a subject has been finished is connected, the respiratory waveform data is transmitted, and calculation using the respiratory waveform data is performed in accordance with procedures, which will be described later. Moreover, the respiratory waveforms or a temporal change (temporal) of the waveform, which is the result of the calculation on the basis of the respiratory waveform is displayed on a display screen in a time series or printed by a printer or the both are performed so that a medical staff who observes the screen display or the print result can evaluate the sleep.

In order to realize these functions, the respiratory waveform analyzing device 3 is provided with an input end 3-1 for taking in respiratory waveform digital data from the outside, a memory unit 3-2 which temporarily records and holds the taken-in data, an analysis unit 3-3 which reads out the recorded data and performs a calculation operation using that, which will be described later, a display unit 3-4 which displays time-series data, which is the result of calculation outputted from the analysis unit 3-3, on the display screen, a printer unit 3-5 which similarly prints the outputted time-series data, and a data transmission end 3-6 which transmits the data of the calculation result to the outside.

[Operation of Respiratory Waveform Analyzing Device]

Next, an operation of a respiratory waveform calculation performed by the respiratory waveform analyzing device 3, which is a characteristic configuration of this system 1 will be described.

The analysis portion 3-3 provided in the respiratory waveform analyzing device 3 extracts the respective frequency domains as follows, for example, from a plurality of Fourier spectra at the time which becomes a start point of each Fourier window period obtained by executing Fast Fourier Transform by shifting time by five seconds for 5-minute Fourier window period from the inputted respiratory waveforms and creates and outputs a temporal change of a waveform with the shift interval of 50 seconds:

0.11 to 0.5 Hz (corresponding to the respiratory frequency band)

0.012 to 0.04 Hz (corresponding to the Cheyne-Stokes respiratory frequency band)

The above operation will be described in detail, and in FIG. 2 schematically illustrating the waveform analyzed or generated by this system 1 in each stage, the unprocessed respiratory waveform including various frequency components are as illustrated in FIG. 2A, while the analysis unit 3-3 sets window time tFFT from a start point 2a of this waveform or specifically, a transform window 2b1 for 5 minutes, for example, and executes the fast Fourier transform (FFT) for the waveform included in this section. The window time tFFT is not limited to 5 minutes but can be chosen from a wide range from 30 seconds to 30 minutes, for example, as long as a temporal change of the target frequency band power in the sleep period of the subject can be observed. As the result of the execution, a Fourier spectrum 2c1 of the waveform in this section is created.

Next, the analysis unit 3-3 similarly sets a Fourier transform window 2b2 of the window time tFFT from a position shifted in the time forward direction by shift time ts or specifically by 50 seconds, for example, from the start point 2a of the waveform and executes fast Fourier transform again and as a result, obtains a Fourier spectrum 2c2 in this section.

Similarly to the window time, the shift time ts is not limited to 50 seconds but can be chosen from a wide range from 2 seconds to 5 minutes, for example, as long as a temporal change in the target frequency band power in the sleep period of the subject can be observed.

Similarly, a Fourier spectrum is created by executing fast Fourier transform in the respective Fourier transform windows obtained by shifting the start point of the Fourier transform window by the integral multiple of the shift time ts and continues this operation until the end point of the Fourier transform window reaches an end point 2d of the respiratory waveform. In an actual calculation operation, the respiratory waveform is measured for a predetermined measurement period including sleep time for one night of the subject or 8 hours, for example, and the start point 2a of the waveform corresponds to the start time of the measurement period, while the end point 2d corresponds to the end time of the measurement period.

Next, the analysis unit 3-3 extracts 0.11 to 0.5 Hz (corresponding to the respiratory frequency band), 0.012 to 0.04 Hz (corresponding to the Cheyne-Stokes respiratory frequency band), for example, or other frequency domains in the frequencies included in each Fourier spectrum for all the plurality of Fourier spectra obtained by the above operation and obtains a power changing waveform of a specific frequency domain (hereinafter also referred to as specific frequency waveform) 2e, which is a waveform obtained by plotting the power on the time of the start point of the respective Fourier windows, that is, a waveform illustrating how the power of the specific extracted frequency band changes in accordance with the time in the sleep.

In extracting the specific frequency waveform, only any of the frequency domains may be selected and extracted or other frequency domains can be used. Also, the above-illustrated frequency domains are all examples and can be changed as appropriate in putting the present invention into practice, and the above description is not limiting.

The temporal change of the waveform of this specific frequency power is a waveform illustrating changes of the respiratory frequency component, a Cheyne-Stokes respiratory frequency component or a frequency component of a noise component caused by measurement over time for a period from the start time of the respiratory waveform measurement to the measurement end time or 8 hours, for example.

Therefore, a medical staff who will make a diagnosis of the state during sleep of the subject can clearly observe a temporal change of the respiratory power during sleep, presence of the Cheyne-Stokes respiration and a temporal change of the power, and presence of a noise component caused by the measurement and a temporal change of the power on the basis of direct and physiological grounds from the respiratory waveform data, which is important physiological data directly linked to the state of sleep of the subject, by observing the temporal change of these specific frequency waveforms which is displayed on a screen or printed and can be visually recognized.

Moreover, the physiological data required for the observation can be sufficiently obtained through one channel of a respiratory waveform, and there is no cumbersome problem of placing a large number of electrodes into contact without detachment as in electrocardiography or of a sensor unit required to be attached like an electrode by a medical staff; but measurement is relatively easy.

As a result, instead of the inpatient testing method imposing a large burden of costs and time to the subject and the society as a whole, which is PSG, or by conducting the test using this system with the purpose of a screening test before such inpatient test, the great advantages described above can be obtained.

Also, this system may be configured to have the following functions in addition to the above functions. When the measured respiratory waveform displayed on the display part 3-4, the respiratory frequency extracted waveform or the waveform from which the Cheyne-Stokes frequency is extracted is observed by a medical staff so as to make various diagnoses, there can be a case in which data of a specific measurement time domain instead of the total measurement period is to be enlarged and the neighboring region including the neighboring time thereof, that is, the selected time needs to be particularly observed.

Thus, in this system 1, an operator first selects the time to be displayed in an enlarged manner by moving a cursor on the display unit 3-4 or reading out specific time from the printed-out waveform and inputting the time by an attached keyboard or the like.

The analysis unit 3-3 can be configured to create a frequency spectrum of this respiratory waveform as above at the selected time or the vicinity thereof, that is, in the neighboring region including the selected time and an enlarged diagram of each enlarged waveform with a short time interval and the like and to similarly display, to print or to output it to the outside.

[Case Data]

A process of creating each band extracted waveform and each calculation waveform from original measured respiratory waveforms will be described with exemplified waveform data. The following numeral values are only exemplification, and execution with appropriate change is possible.

Figure 3:
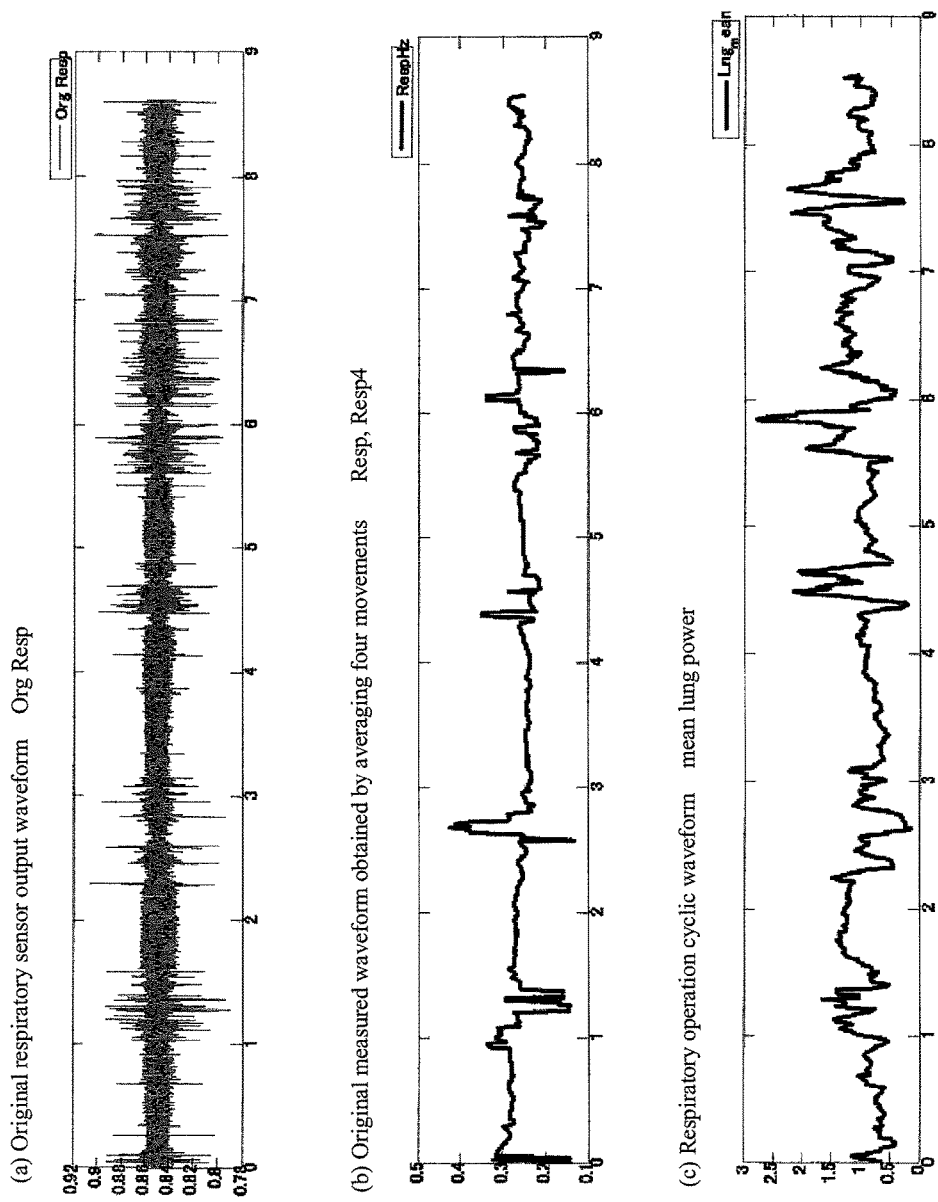
FIG. 3 is an example of a measured waveform by using the system in FIG. 1.

(a) Original Respiratory Sensor Output Waveform: Org Resp (FIG. 3A)

The lateral axis indicates time from start of the measurement and the unit is hour. The vertical axis indicates the size of measured power (The same applies to the following).

The sampling frequency of this original respiratory sensor output waveforms is 16 Hz.

(b) Original Measured Respiratory Waveform Obtained by Averaging Four Measurements: Resp4, Res (FIG. 3B)

In order to suppress unexpected noise involved in sampling, past four measured data are averaged, and this 4 Hz-waveform is used as an original waveform for the subsequent band extraction and data processing.

That is, this corresponds to an unprocessed respiratory waveform in FIG. 2A described above.

(c) Respiratory Operation Cycle Waveform: Mean Lung Power (FIG. 3C)

This is a component of 0.11 to 0.5 Hz, which is a high frequency domain corresponding to the respiratory frequency band from the original measured respiratory waveform Resp obtained by averaging four measurements is extracted and average power of the band of 0.08 Hz before and after the cycle of the maximum power thereof. By tracking and observing the temporal change of this waveform, a temporal change in the size of a respiratory operation of the subject can be known.

This respiratory operation cycle waveform, mean lung power, and the following normalized Cheyne-Stokes respiratory power waveform, CSR/mean lung power, correspond to the power changing waveform 2e of the specific frequency domain illustrated in FIG. 2B.

Figure 4:
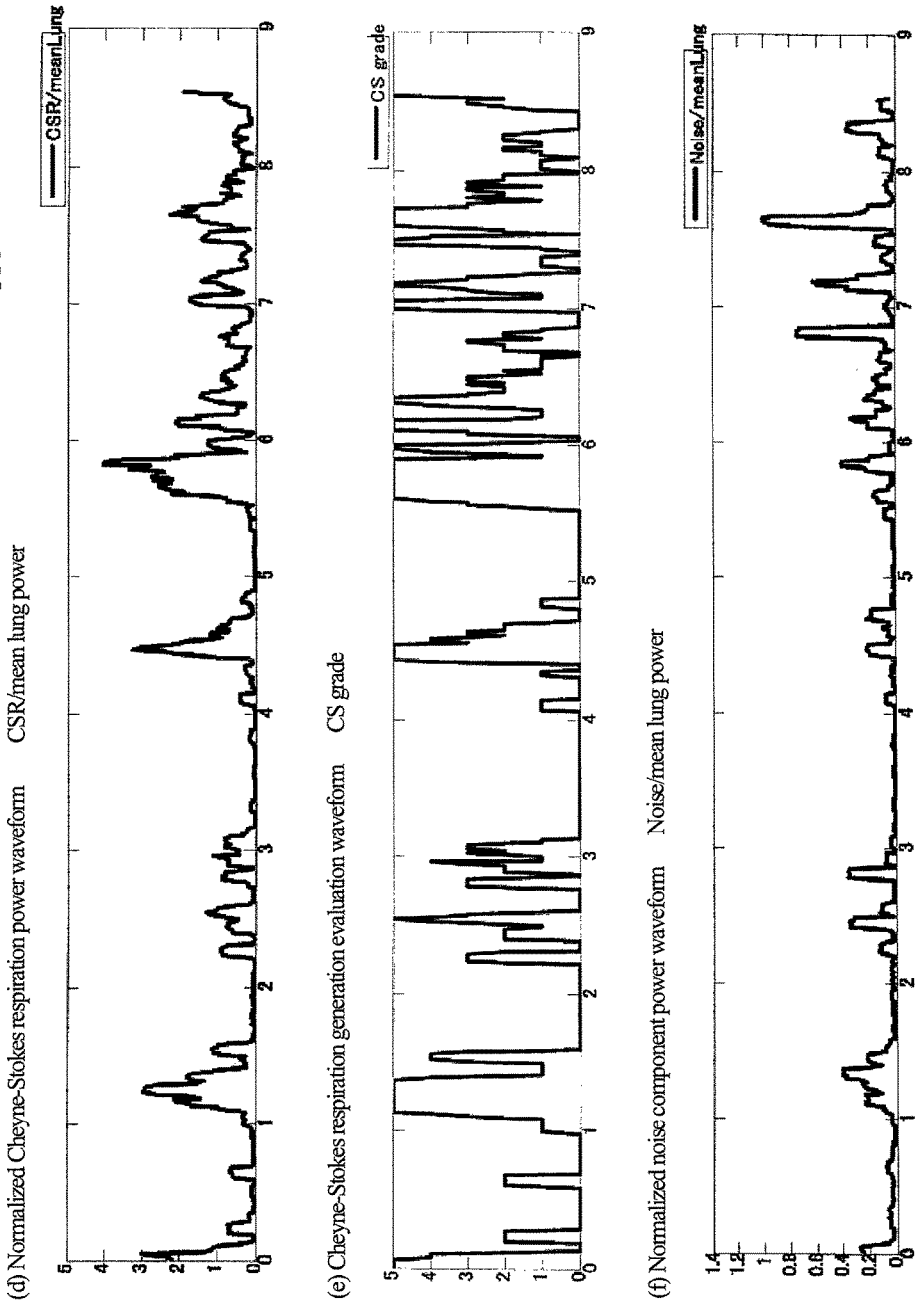
FIG. 4 is an example of a measured waveform by using the system in FIG. 1.

(d) Normalized Cheyne-Stokes Respiratory Power Waveform: CDSR/Mean Lung Power (FIG. 4D)

This is a waveform obtained by extracting a range of 0.012 to 0.04 Hz corresponding to the band of the CSR cycle from the original measured respiratory waveform Resp4 obtained by averaging four measurements. The waveform is divided by the power mean lung power of the respiratory operation cycle waveform and normalized.

(e) Cheyne-Stokes Respiration Generation Evaluation Grade: CS Grade (FIG. 4E)

The above normalized Cheyne-Stokes respiration power is classified into 6 grades from 0 to 5, for example, in accordance with the size of the amplitude, and a temporal change of the grade is displayed.

(f) Normalized Noise Component Power Waveform: Noise/Mean Lung Power (FIG. 4F)

This is a waveform detected by the above-described respiratory sensor but not caused by a respiratory airflow and illustrating a temporal change of the noise component. This noise component is caused by a body motion of the subject, for example, and a temporal change of the size of the body motion of the subject in the sleep period can be observed. Moreover, a body motion sensor, a pressure sensing mat, a body motion detecting band or the like other than the respiratory sensor is not necessary.

As a method of creating this noise component waveform, a specific frequency may be extracted, but in this embodiment, the respiratory waveform Res4 is further subjected to moving average for smoothing, and a part further projecting from the smoothing waveform is detected for creating the waveform.

This method will be described by referring to FIGS. 5 and 6.

Figure 5:
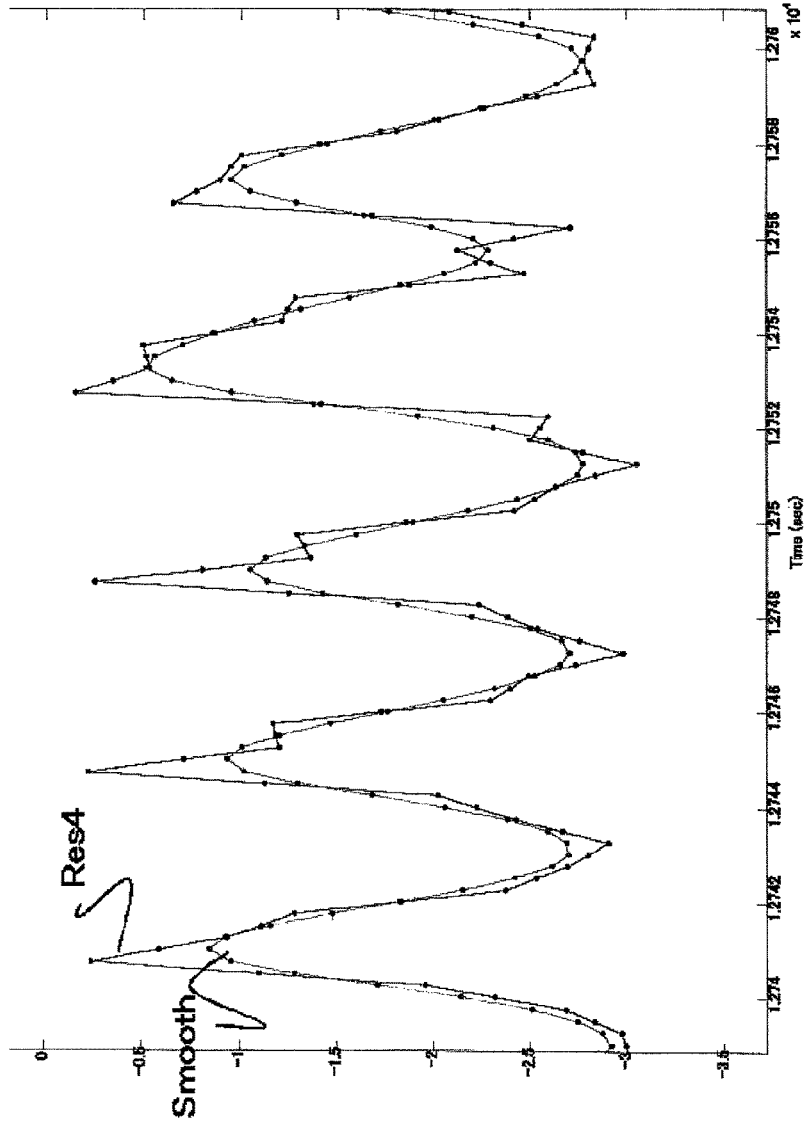
FIG. 5 is an example of a measured waveform by using the system in FIG. 1.

FIG. 5 illustrates the respiratory sensor output waveform obtained by averaging four measurements (Res4) and the smoothing waveform subjected to moving average of the past 5 seconds of this Res4 (Smooth) in a juxtaposed manner. A part of the measured waveform over the entire sleep period is taken out and illustrated, in which the lateral axis indicates elapsed time (Sec, 104 scale).

Figure 6:
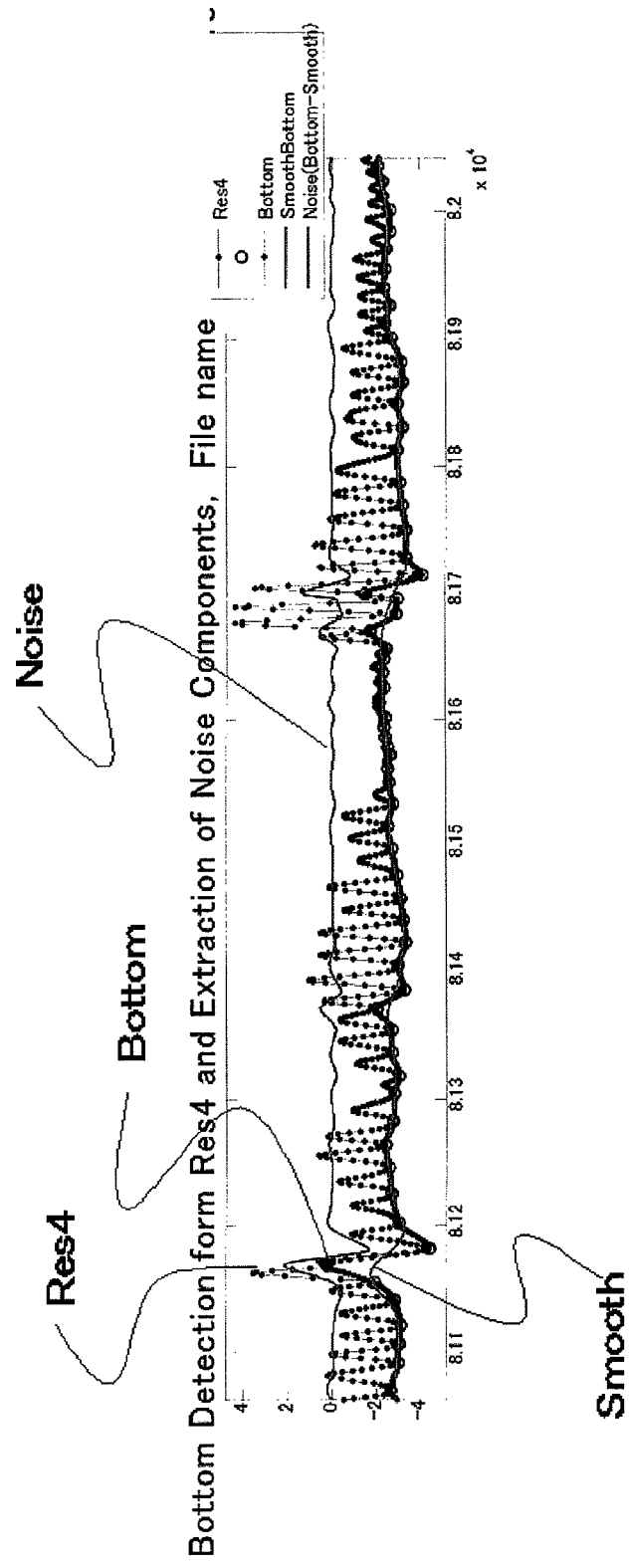
FIG. 6 is a waveform diagram for explaining a method of creating a noise waveform by using the system in FIG. 1.

FIG. 6 further illustrates a method of creating a noise component waveform (Noise), in which an envelope (bottom) on the lower part of the respiratory sensor output waveform obtained by averaging four measurements (Res4) is created first, and the smoothing waveform (Smooth) is subtracted from this bottom, and the result is the noise waveform (Noise).

That is, in the light of the smoothing waveform (Smooth) indicating the trend of the respiratory waveform, the sensor output departing from this trend is extracted as a noise portion.

FIG. 4F illustrates a temporal change of the normalized noise component power waveform Noise/mean lung power in the sleep period obtained by being divided by the above-described mean lung power and normalized.

(g) Variation Index of Respiratory Cycle: Var (FIG. 7G)

Next, the variation index, var, of the respiratory cycle to see a temporal change in the variation of the respiratory cycle of the subject will be described by referring to FIG. 8.

Figure 8:
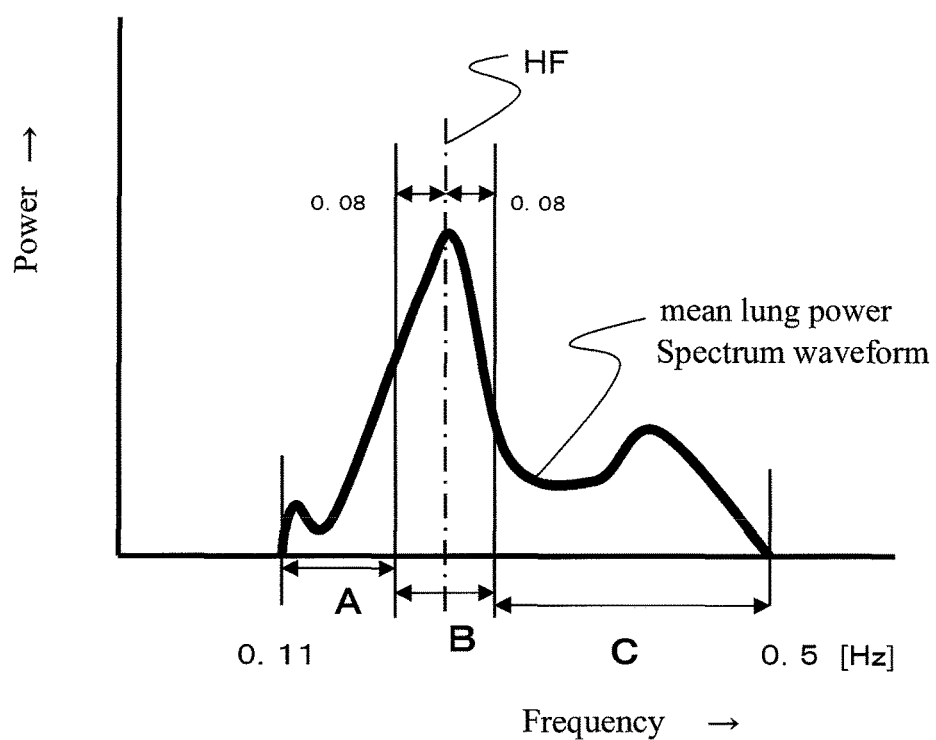
FIG. 8 is a schematic diagram for explaining a principle for calculating a variable index by using the system in FIG. 1.

In FIG. 8, first, the above-described respiratory operation cycle waveform, mean lung power, is schematically illustrated. In accordance with the above definition, the band is 0.11 to 0.50 Hz as illustrated. The lateral axis of FIG. 8 indicates a frequency and the vertical axis indicates power.

Here, a peak frequency found in the mean lung power, that is, a central frequency of the respiratory cycle is defined as HF (high frequency), and regions defined with the width of 0.08 Hz on the both sides of the HF are defined as central band regions (B). And a region having lower frequencies than the central band region is defined as left side band region (A), while a region having higher frequencies than the central band region is defined as a right side band region (C).

Here, if variation of the respiratory cycle of the subject is large, in the spectral diagram in FIG. 8, a quotient obtained by dividing the value obtained by integrating the spectral power of the left side band region (A) and the right side band region (C), that is, the regions of A and C with respect to frequency by a value obtained by integrating the entire spectral power, that is, the regions of A, B, and C with respect to frequency should be larger. This value is called a variation index (var) of the respiratory cycle, and a temporal change of an actually measured value is illustrated in FIG. 7G (h) Standard Deviation of Respiratory Cycle: RespHzSD (FIG. 7H)

Next, two indexes selected from an approach different from the above-described variation index var of the respiratory cycle in order to see a temporal change in variation of the respiratory cycle of the subject will be described.

The inventor has obtained the following finding in making sleep evaluation diagnoses for a large number of cases using the respiratory waveform measurement information of the subject.

As described in the first place, one cycle made of six types of sleep stages is repeated approximately three times in one night typically with approximately a 90-minute cycle in the sleep, and a change in the physiological data in each cycle can be clearly observed by a slow wave component (SWA: Slow Wave Activity) of brain waves as below. In the case of a subject whose comfort level including the quality of sleep has deteriorated by some causes such as sleep apnea, it has been known by the examination by the inventor that the cycle of the sleep stages by SWA breaks down and cannot be clearly observed.

Figure 9:
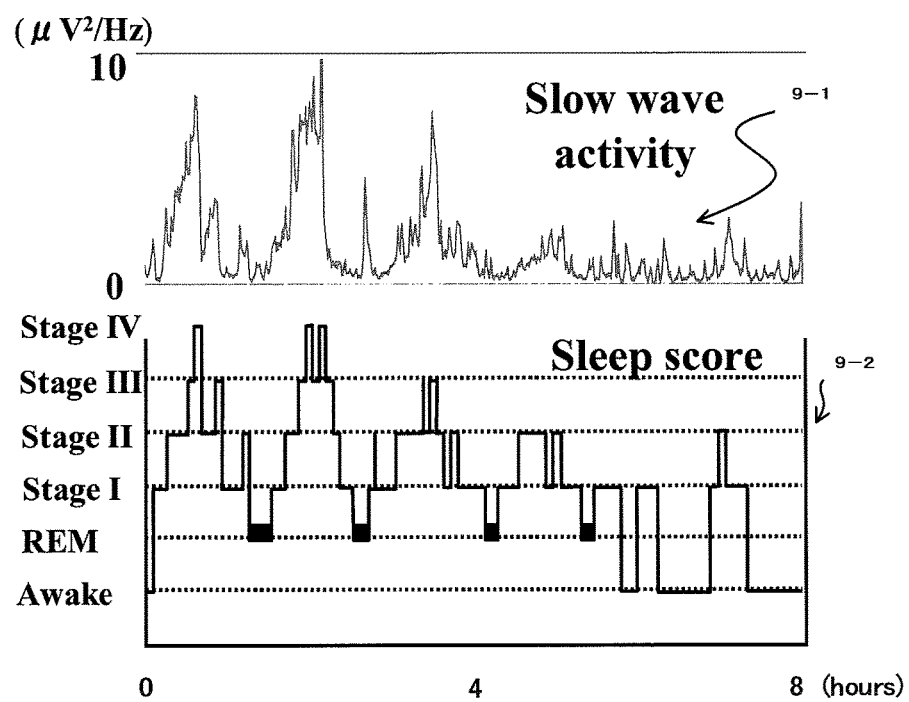
FIG. 9 is a diagram for explaining a typical example of good-quality sleep by using a brain-wave SWA waveform and a temporal change of a sleep stage.

FIG. 9 explains a relationship between the slow wave component (SWA) of the brain waves and the sleep stage for the case of a subject having a good comfort level including the quality of sleep by using a typical pattern. The lateral axis indicates measurement time and represents the whole sleep period for one night (8 hours in the illustration). As clearly known from FIG. 9, the temporal change in the sleep stage cyclically repeated is synchronized with a change in power of the SWA, and particularly the power of the SWA becomes the maximum in a stage 1V in which the sleep is the deepest.

The data in FIGS. 3 to 7 which has been described above is created from the same respiratory sensor output waveform of the same subject found to have no cardiac diseases and a good comfort level including the quality of sleep, but the data in FIG. 9 is not the data of this subject but shows one typical example.

The inventor has paid attention to the respiratory operation of the subject in sleep and has found out that if attention is paid to little change in the respiratory cycle obtained by measurement or in other words, stability of the respiratory frequency or regularity of the respiratory cycle, observation of this sleep cycle and hence, evaluation of the comfort level including the quality of sleep can be made, which has led to completion of the present invention. Hereinafter, the phrase "regularity of a respiratory cycle" is used including properties of little change in the respiratory cycle and stability of the respiratory frequency.

By using the system described above, as a band of the respiratory cycle, the respiratory operation cycle waveform mean lung power described above is extracted, for example, from the respiratory waveform obtained by measurement. By calculating an average value (X bar) of the respiratory frequency first, and further calculating the standard deviation (SD) of the respiratory frequency by using a known statistical method, the size of a change of the respiratory cycle can be known. Moreover, by acquiring an inverse number of the standard deviation (SD), stability of the respiratory cycle can be expressed. Instead of using the average value (X bar) of the respiratory frequency, other indexes such as the respiratory cycle peak frequency (HF) described above may be used.

The inverse number of the standard deviation of the measured respiratory waveform is referred to as RSI (Respiration Stability Index) here. By graphically illustrating the RSI so that a temporal change of sleep in one night can be known, a medical staff can observe and easily determine that the sleep cycle is clearly expressed, and the comfort level including the quality of sleep is good, or clear observation cannot be made and the comfort level including the quality of sleep is poor, or automatic determination can be made by a diagnosing device from the regularity.

On the other hand, in a method of recording and observing a temporal change of the respiratory rate or a temporal change of a heart rate while a subject is sleeping, for example, which is a configuration different from that of this embodiment of the present invention, these waveforms of changes do not match the change of the brain-wave slow wave component (SWA), and thus, it is already known that this method is not suitable for evaluation of the comfort level including the quality of sleep.

Thus, in a system of a variation of the present invention, as described above, from a plurality of Fourier spectra at the time which is a start point of each Fourier window period obtained by executing fast Fourier transform (FFT) by shifting time by 5 seconds of the Fourier window period for 5 minutes from the inputted respiratory waveform, a frequency domain of 0.11 to 0.50 Hz including 0.4 Hz, which is a typical respiratory cycle of a human body, is extracted.

Moreover, in the system of the variation of the present invention, the analysis part 3-3 calculates an average value (X bar) and a standard deviation (SD) of the frequency included in the respiratory frequency band for each Fourier window obtained with the above-described shift interval of 50 seconds.

FIG. 7H illustrates a conventional respiratory cycle standard deviation RespHzSD of a subject. The above-described RSI, which is an inverse number of this SD, is calculated for each Fourier window period having the shift interval of 50 seconds, a graph indicating a temporal change of the RSI in which the power thereof is plotted on the axis orthogonal to the time axis is created, and this can be displayed, printed or outputted to the outside as information of the calculation result. By observing this RSI graph, stability of the sleep cycle and hence, the comfort level including the quality of sleep can be easily observed and diagnosed.

FIG. 7I similarly illustrates the conventional respiratory cycle standard deviation RespHzSD of a subject.

The meaning of the observation of the above-described RSI will be qualitatively described from another point of view.

Figure 10:
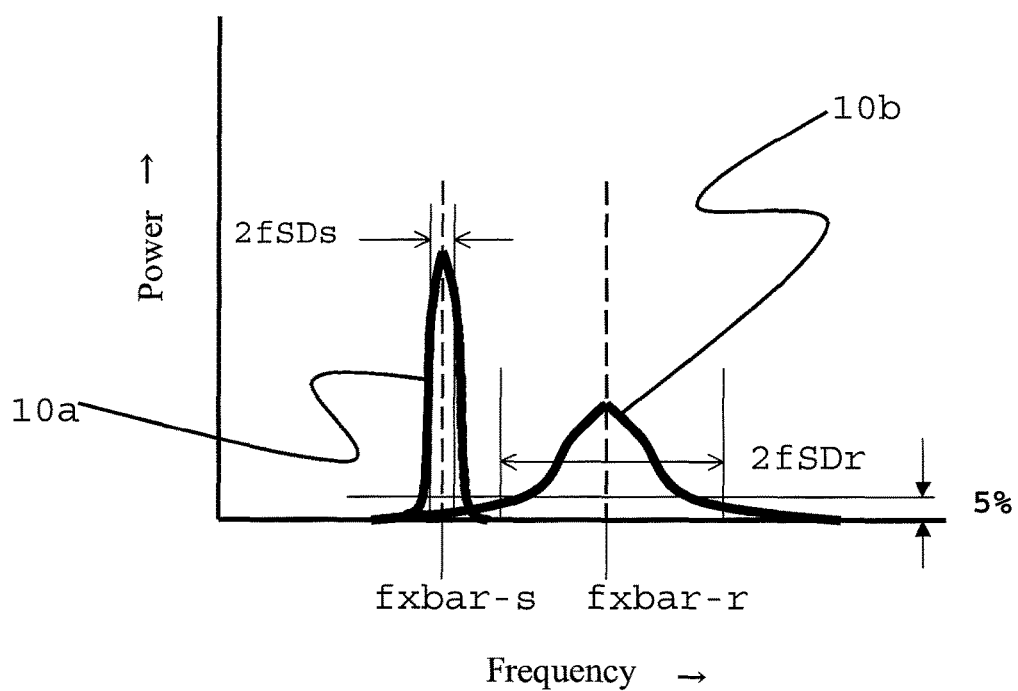
FIG. 10 is a schematic diagram for explaining a principle of calculating a standard deviation of a respiratory cycle by using the system in FIG. 1.
Figure 12:
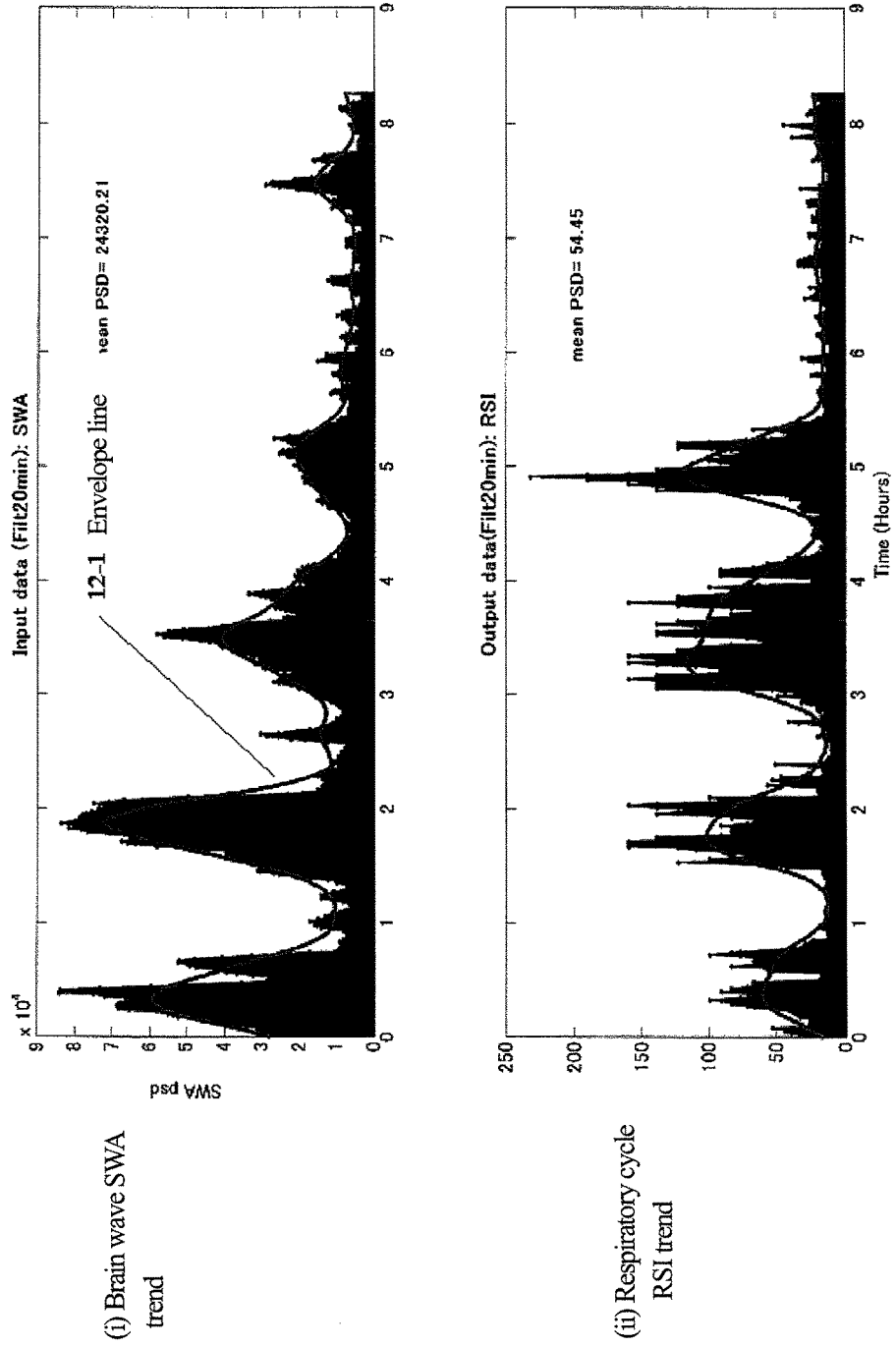
FIG. 12 is each index graph of a first case.
Figure 13:
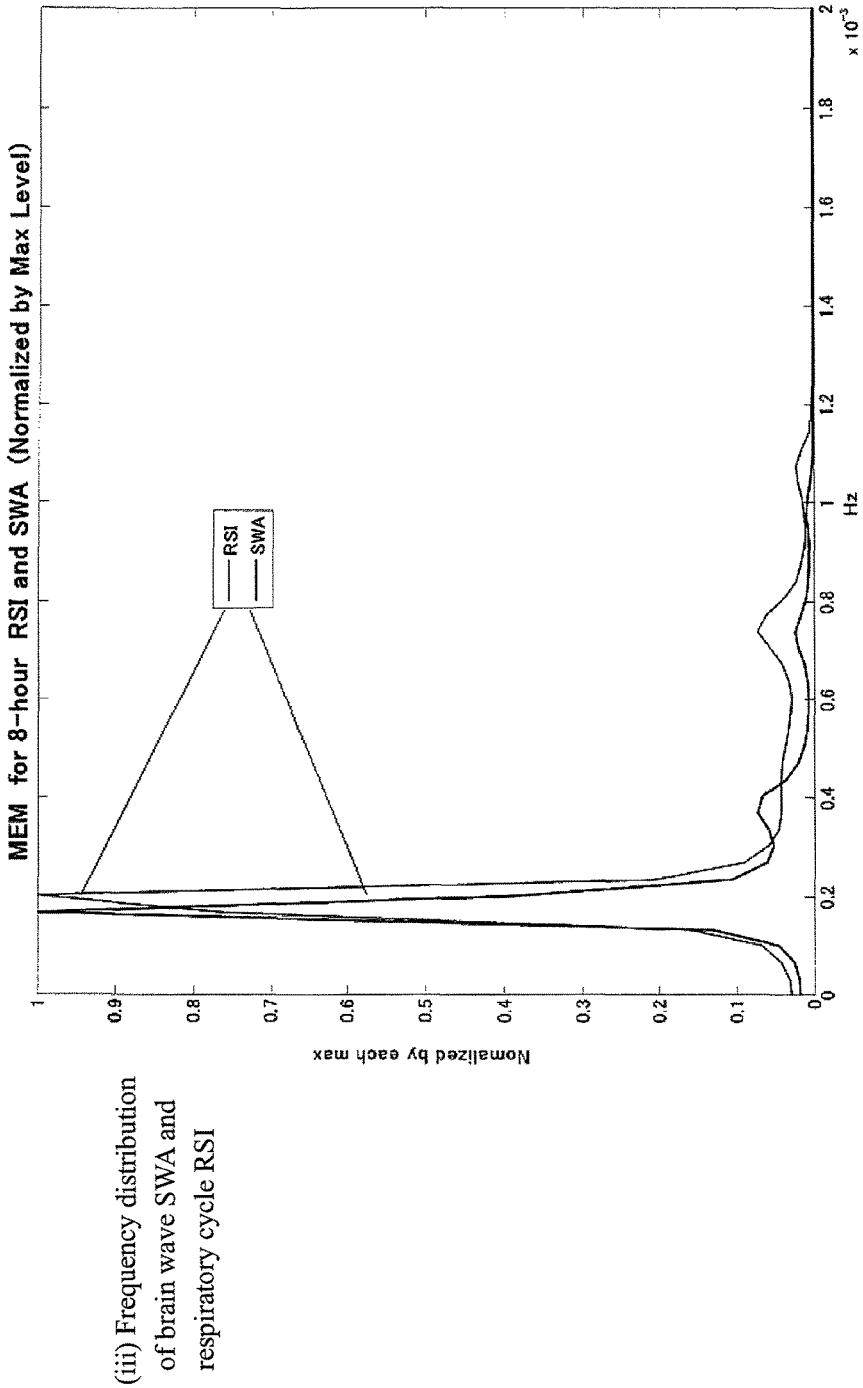
FIG. 13 is each index graph of the first case.
Figure 14:
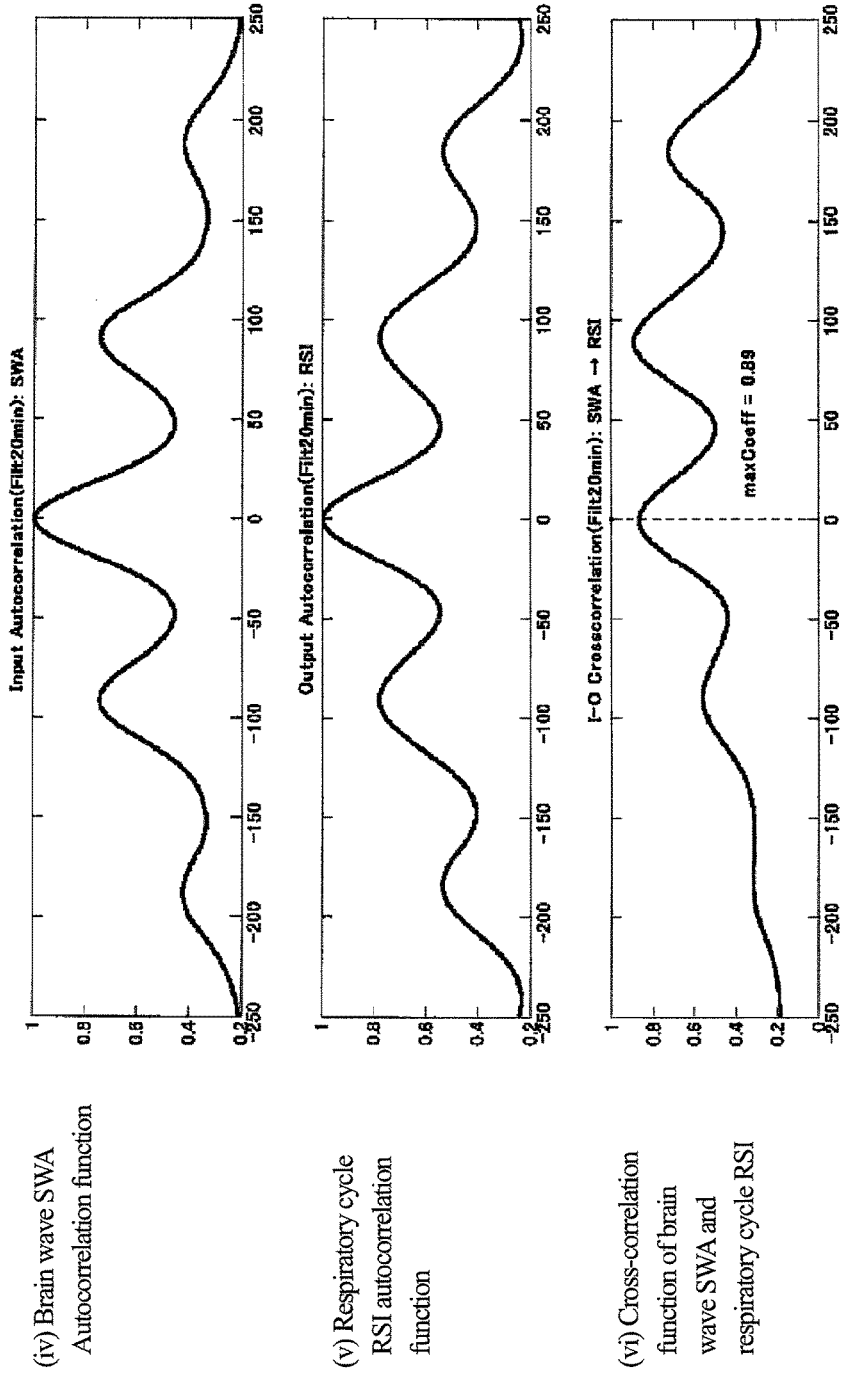
FIG. 14 is each index graph of the first case.
Figure 15:
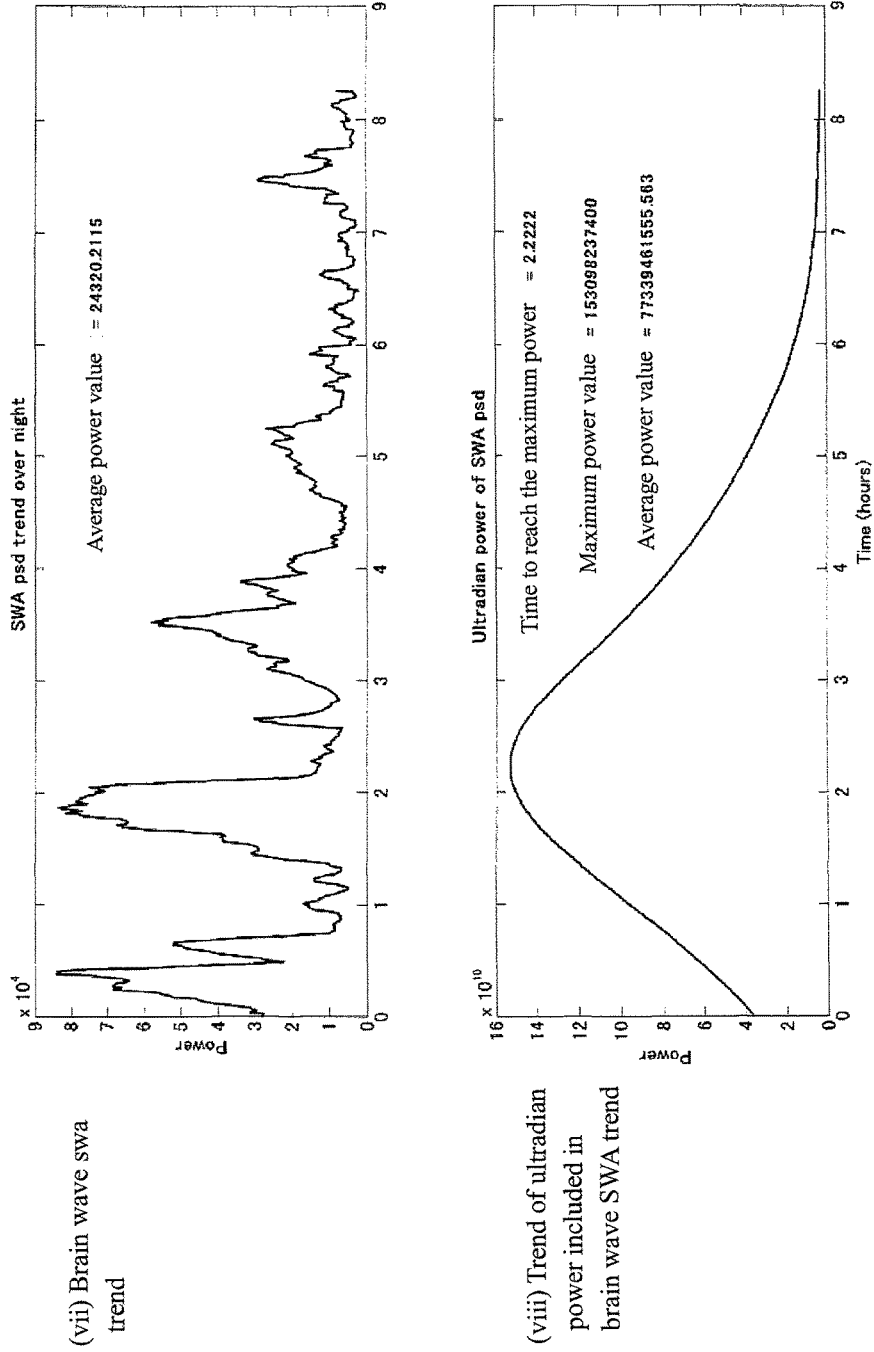
FIG. 15 is each index graph of the first case.
Figure 16:
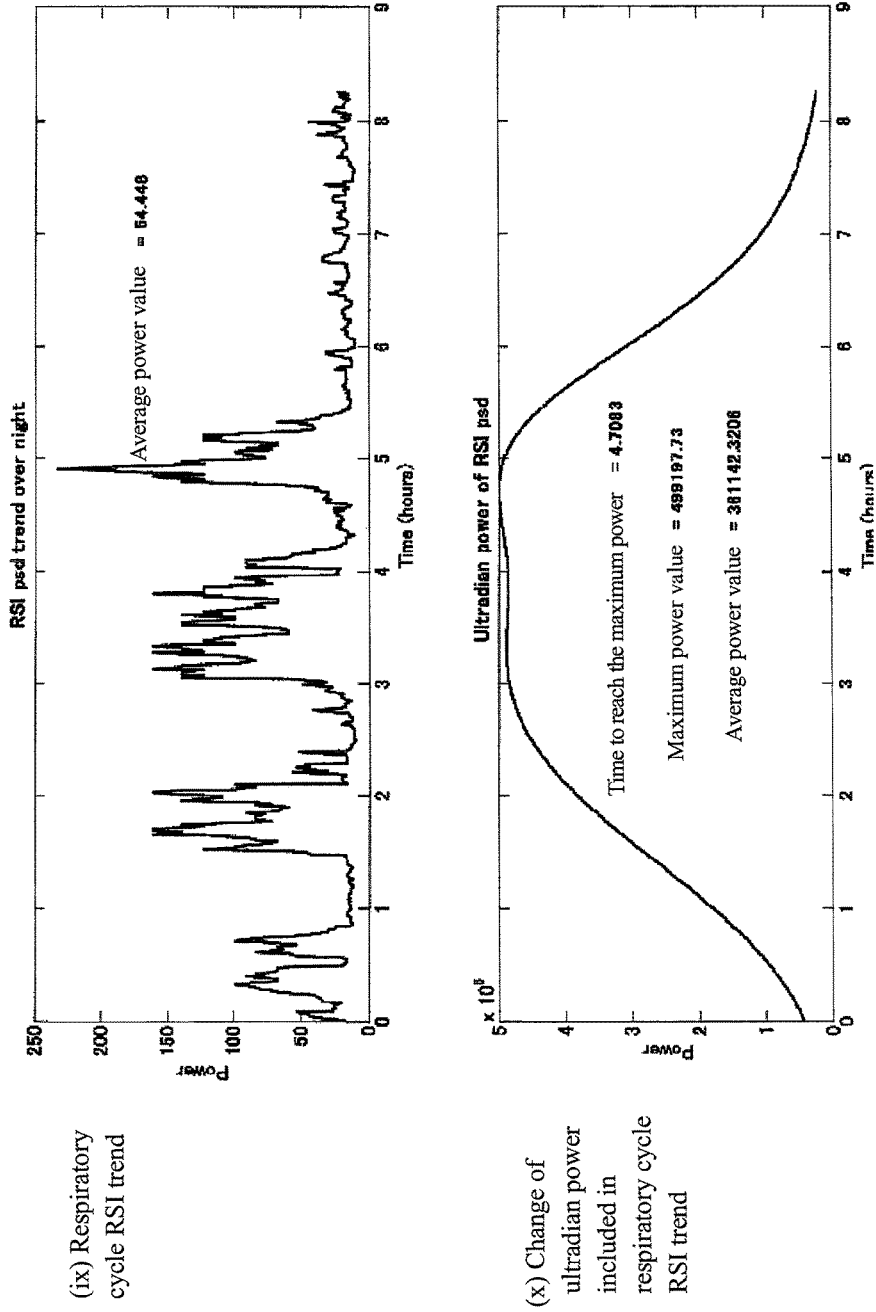
FIG. 16 is each index graph of the first case.
Figure 17:
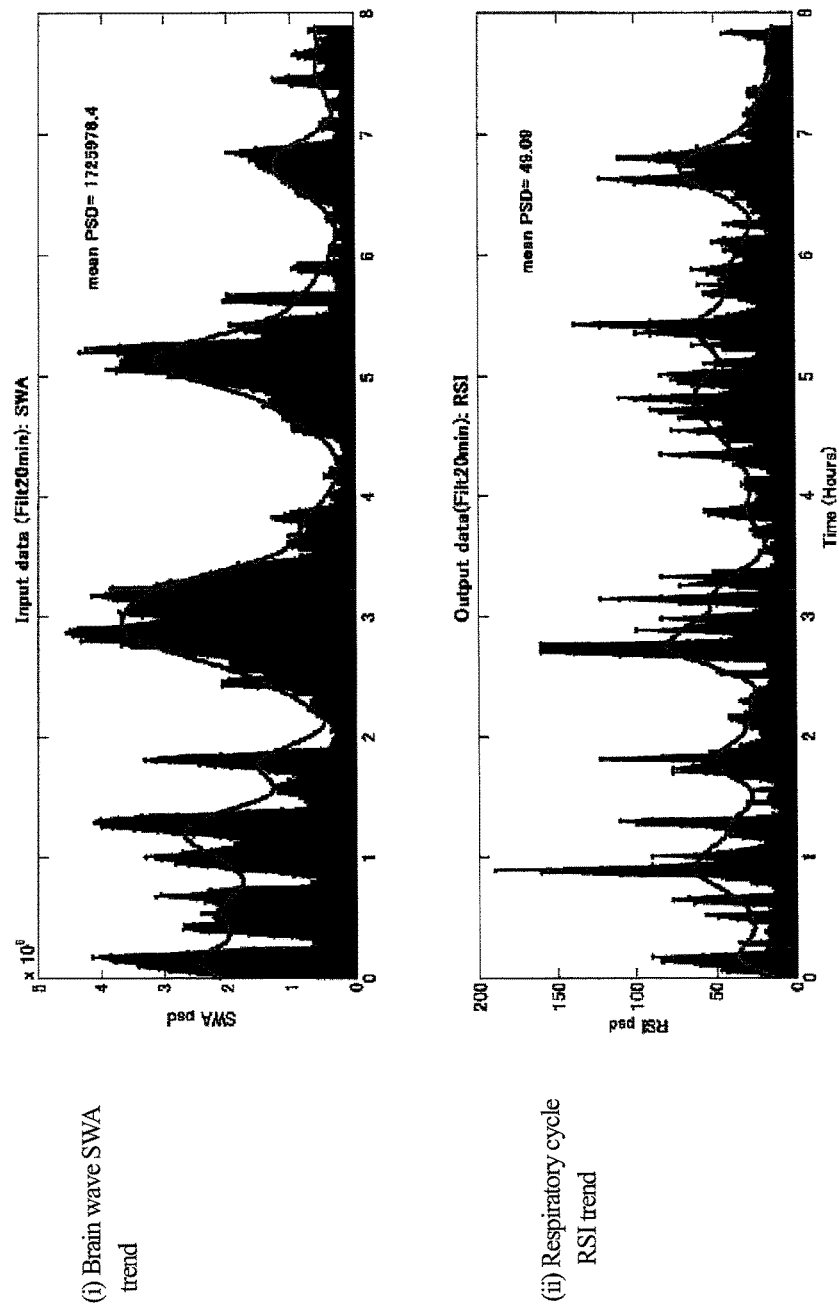
FIG. 17 is each index graph of a second case.
Figure 18:
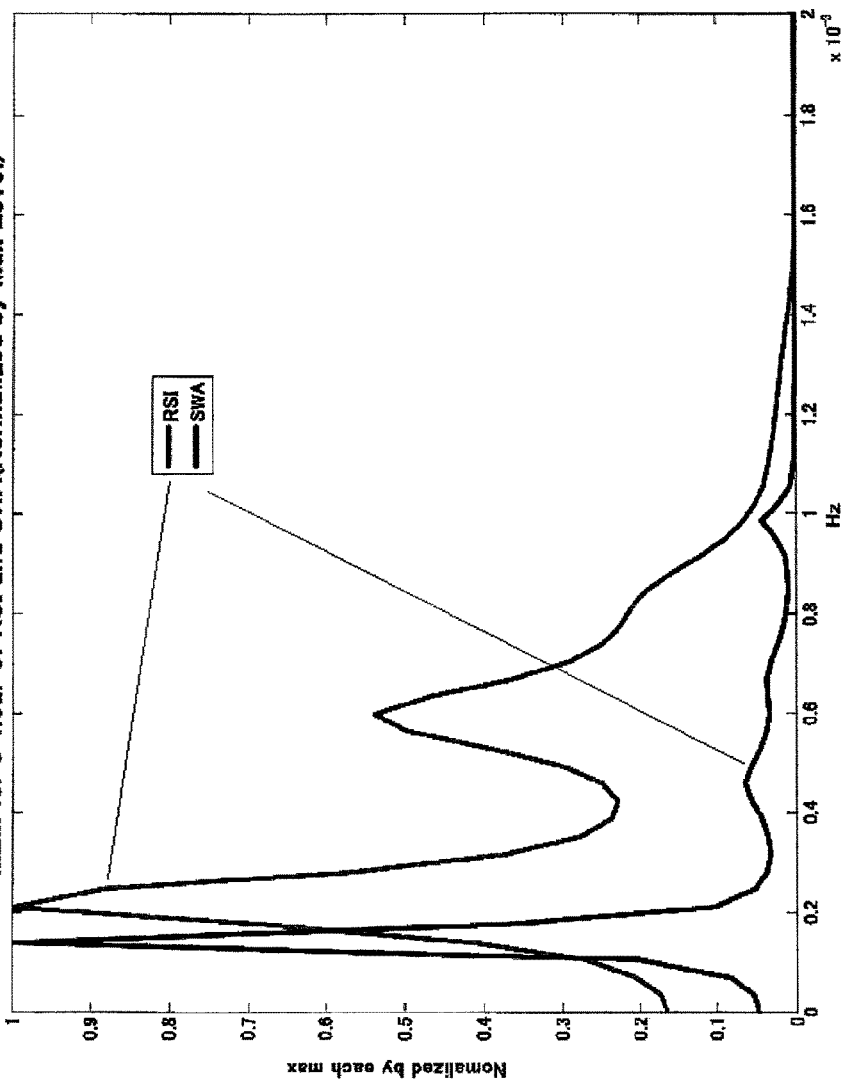
FIG. 18 is each index graph of the second case.
Figure 19:
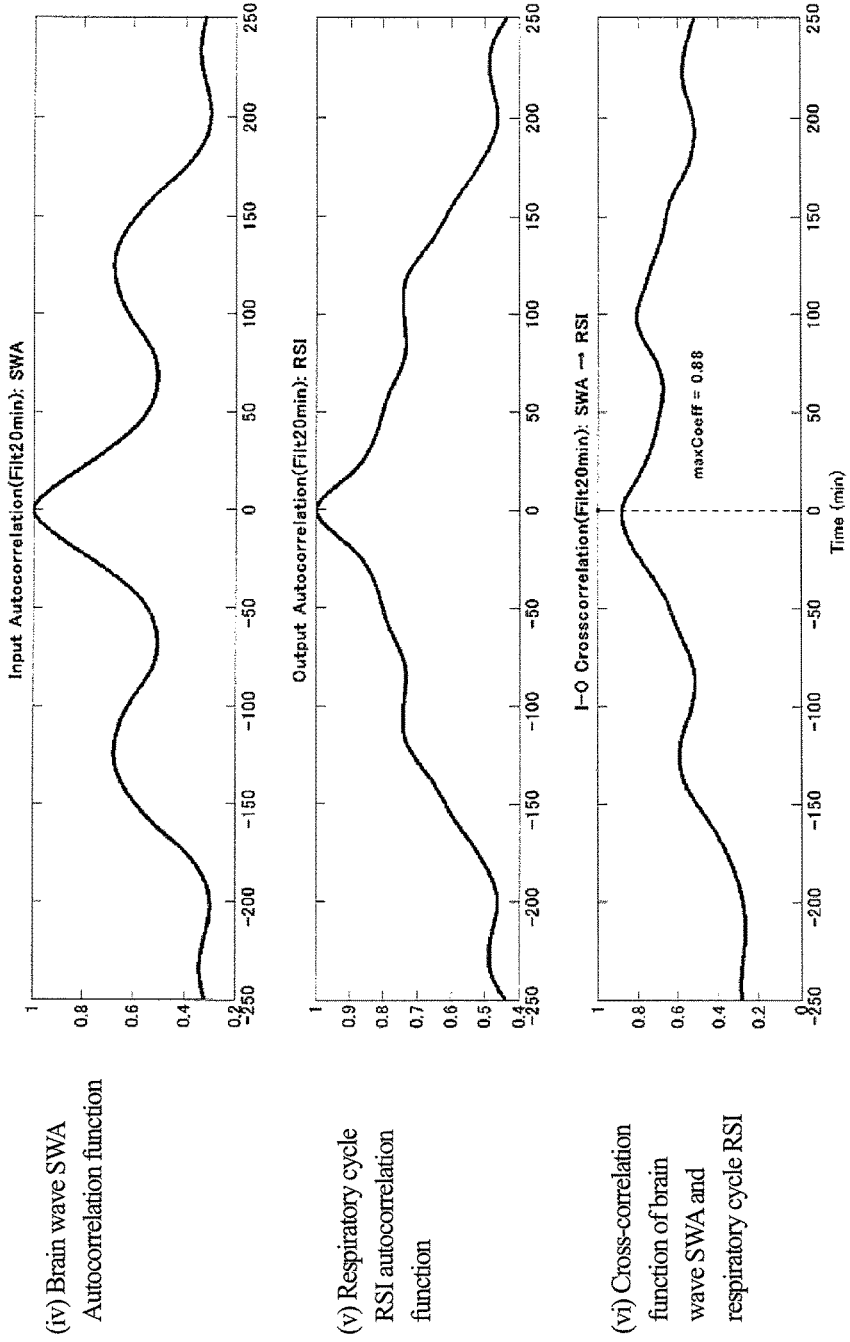
FIG. 19 is each index graph of the second case.
Figure 20:
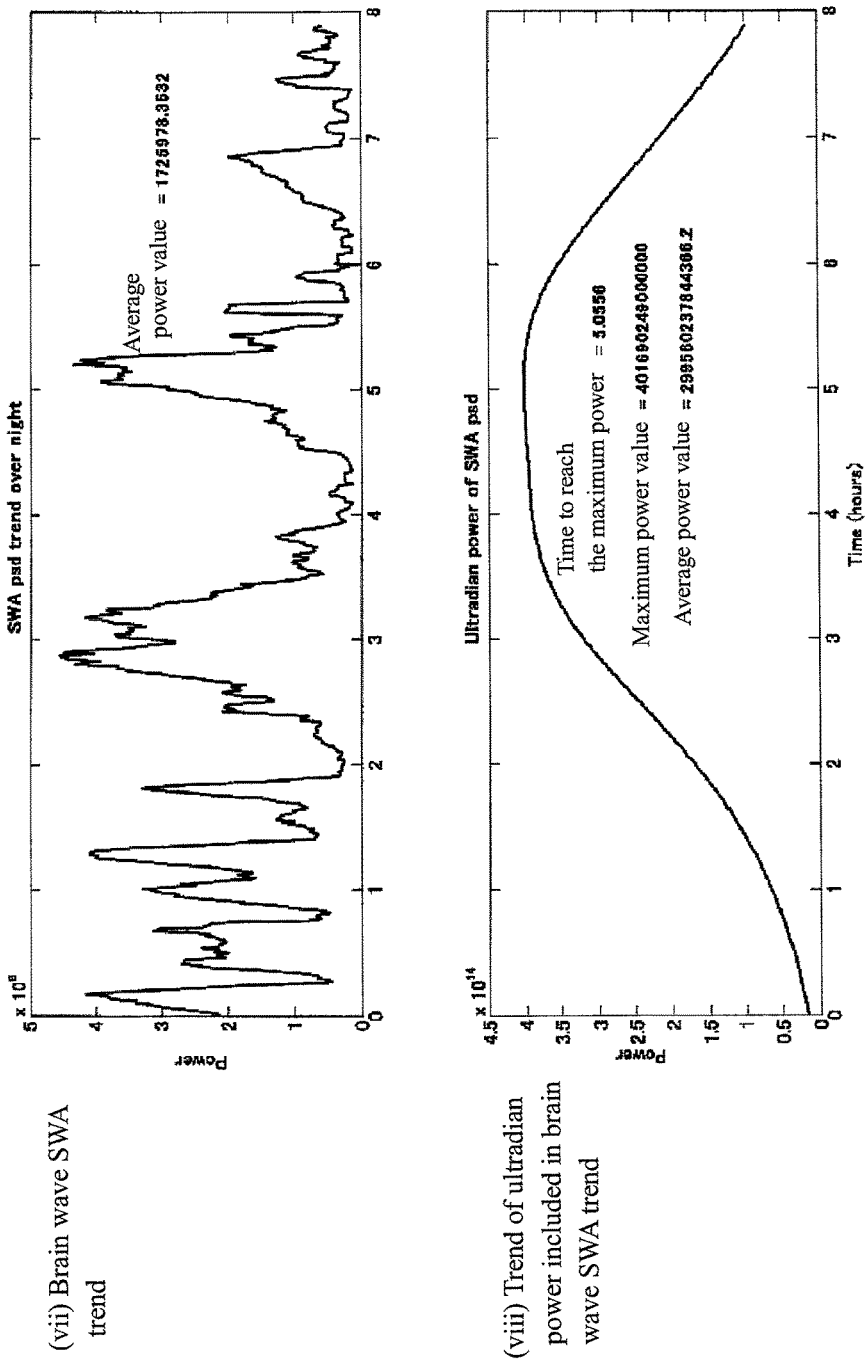
FIG. 20 is each index graph of the second case.
Figure 22:
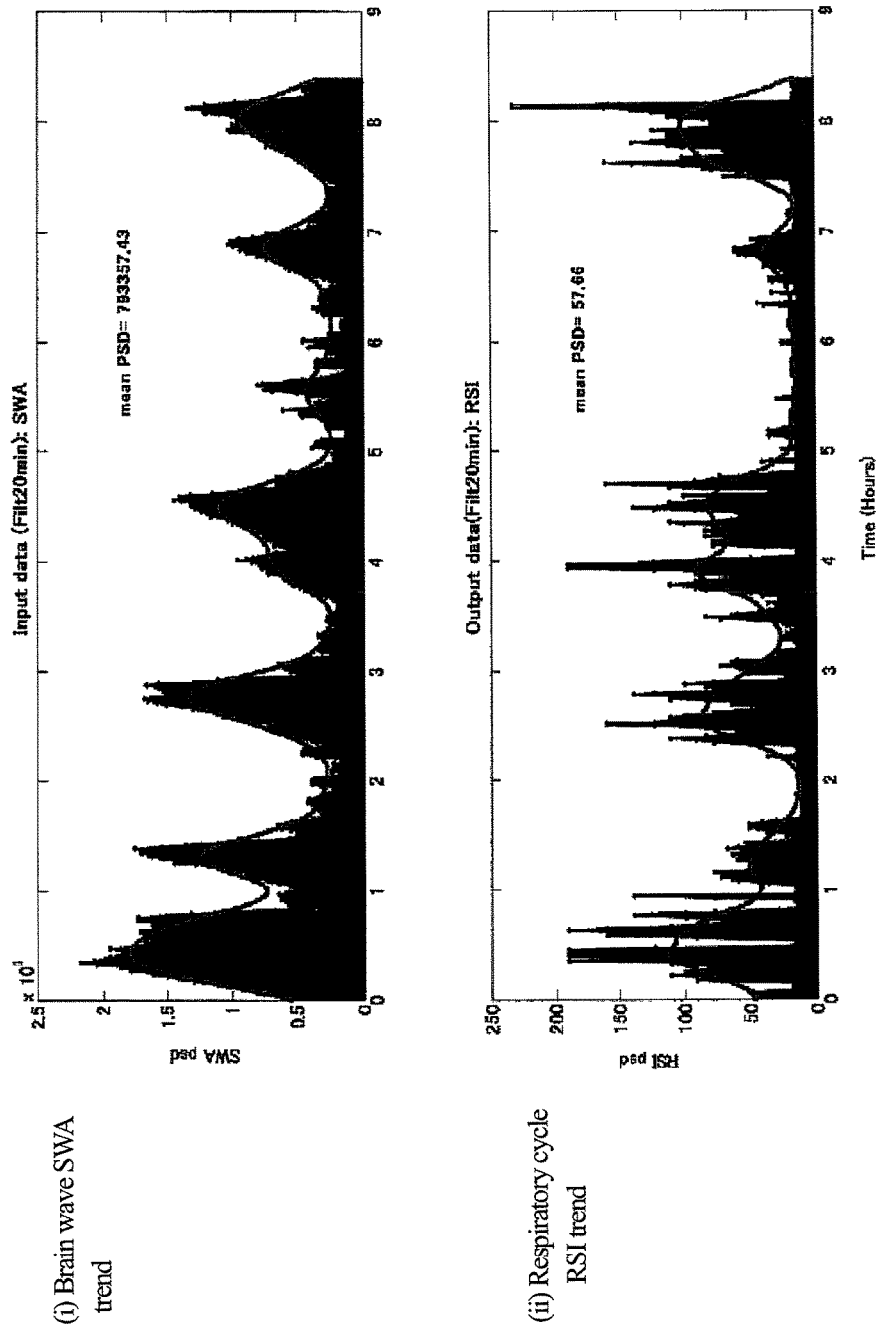
FIG. 22 is each index graph of a third case.
Figure 23:
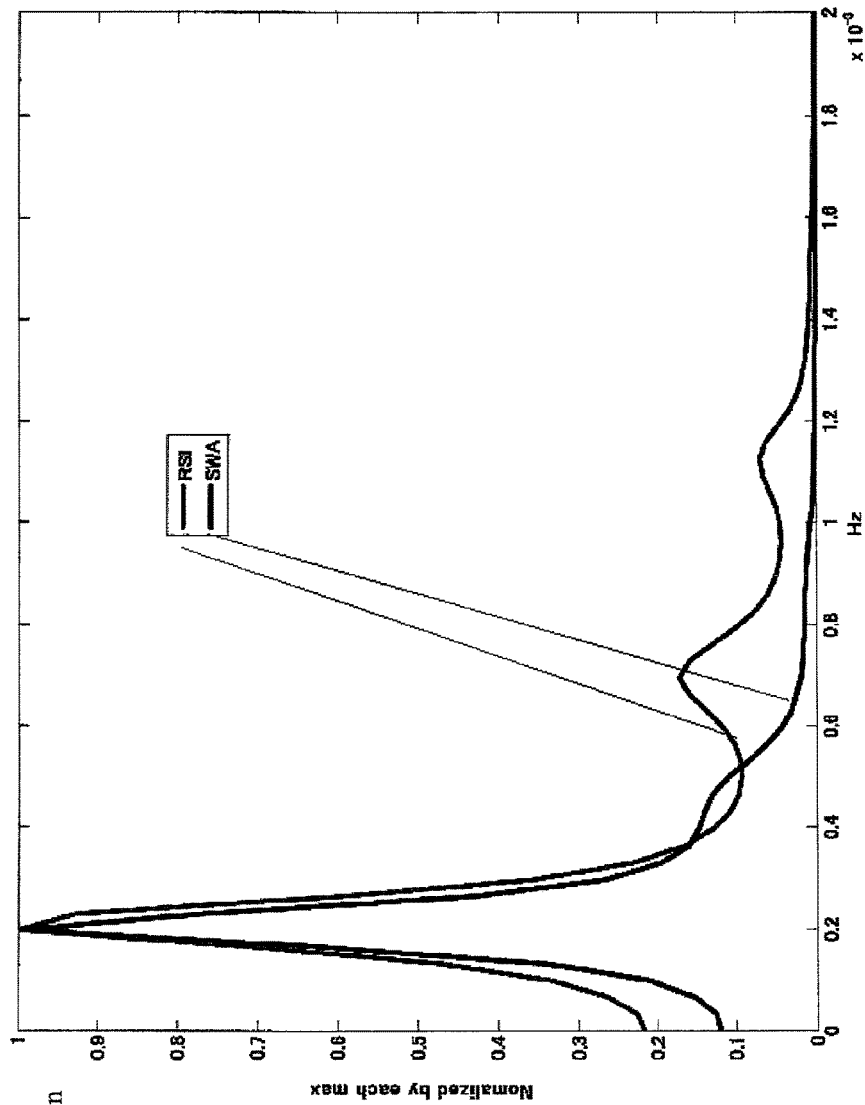
FIG. 23 is each index graph of the third case.
Figure 24:
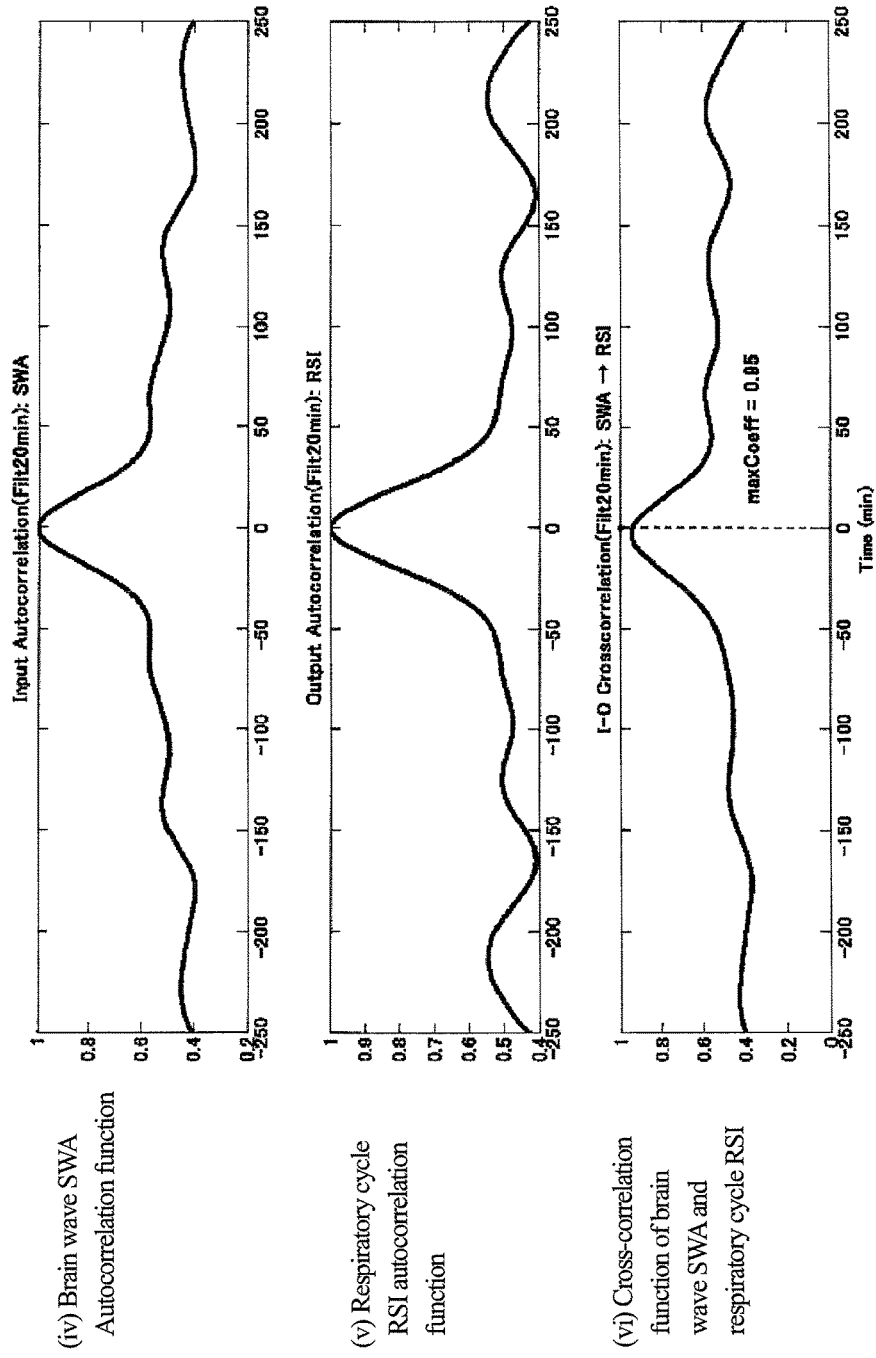
FIG. 24 is each index graph of the third case.
Figure 25:
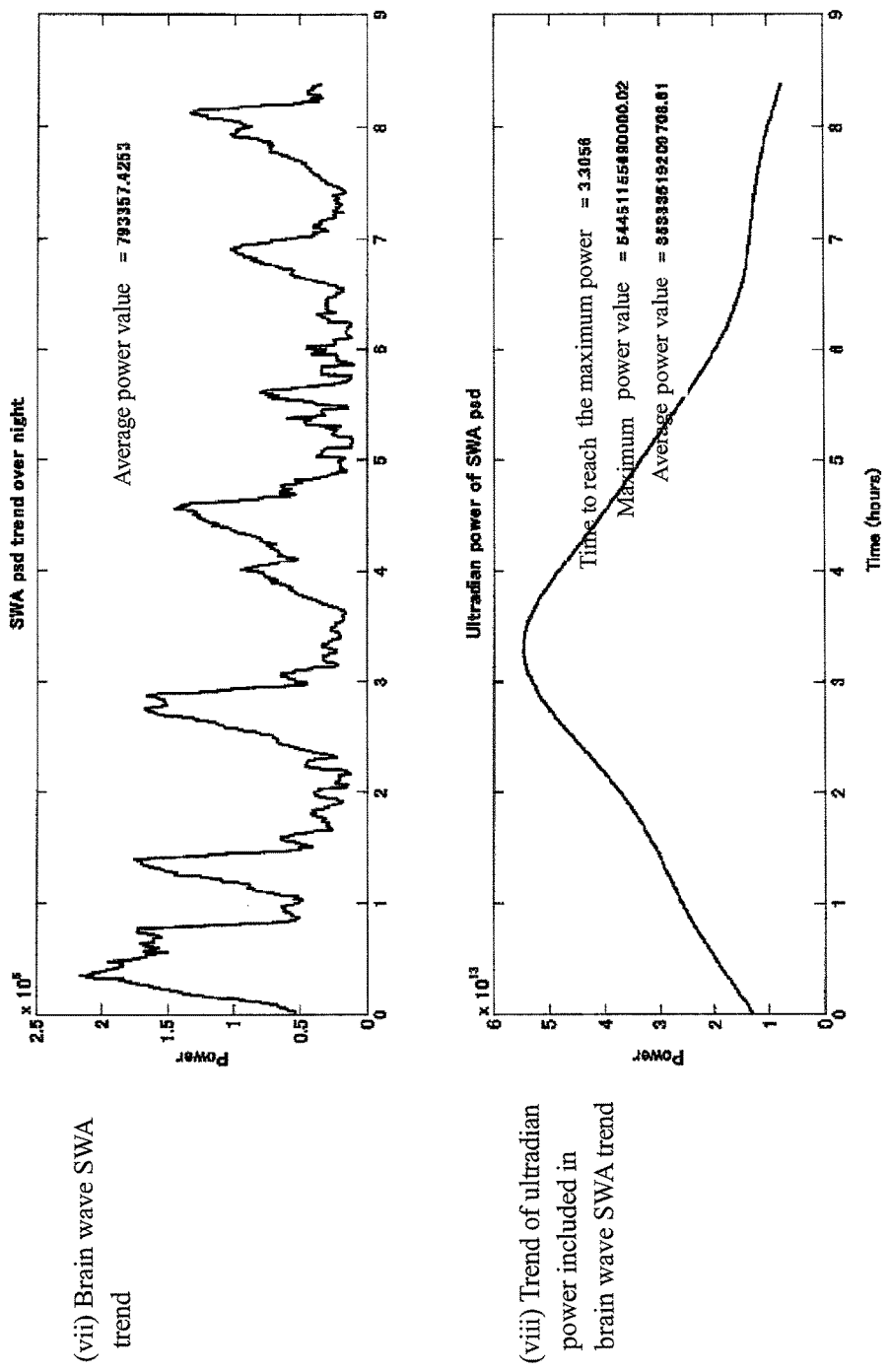
FIG. 25 is each index graph of the third case.
Figure 26:
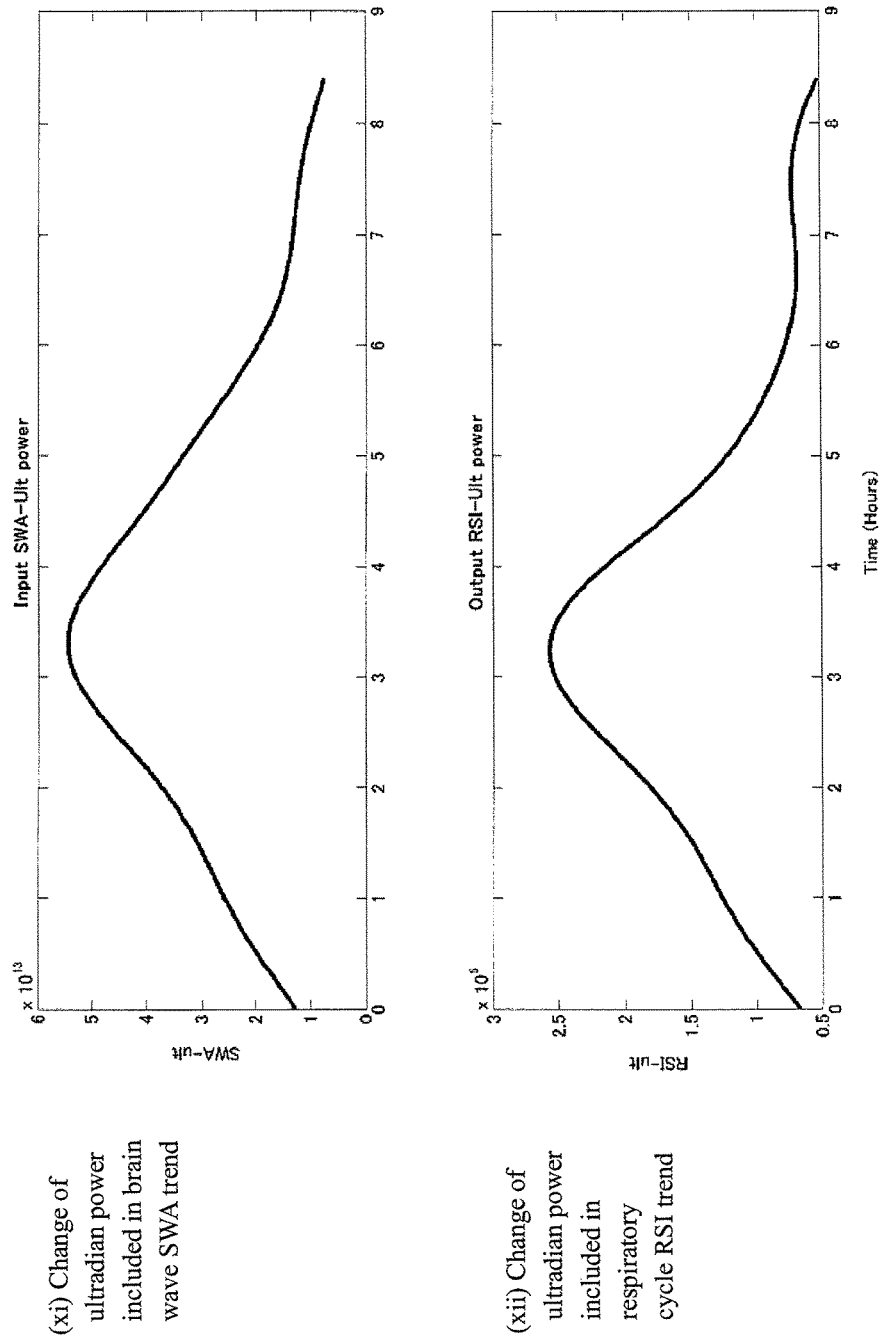
FIG. 26 is each index graph of the third case.
Figure 27:
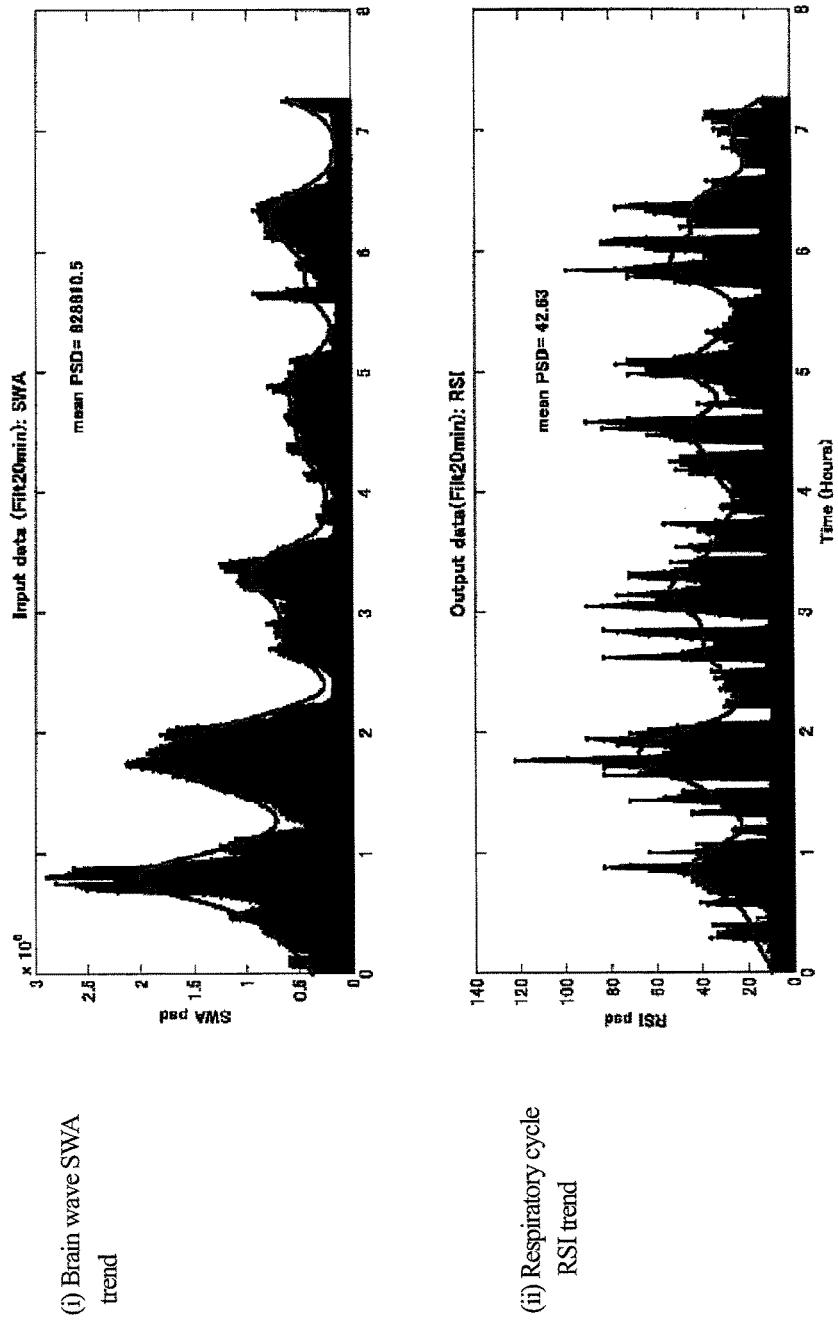
FIG. 27 is each index graph of a fourth case.
Figure 28:
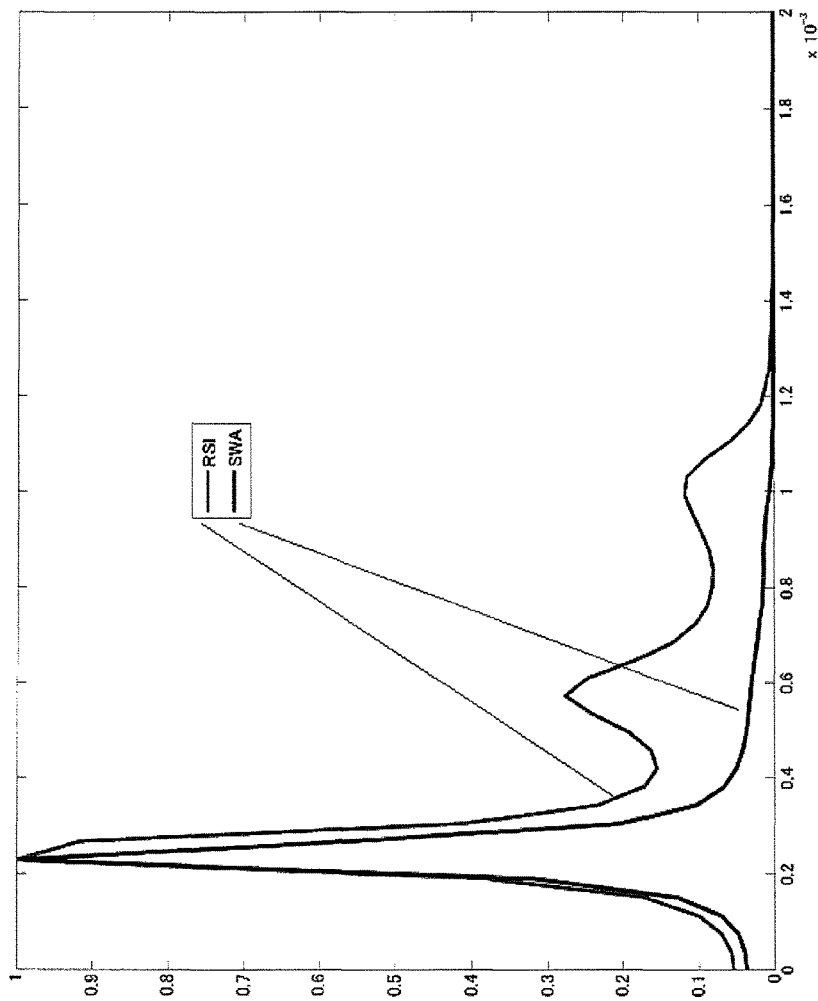
FIG. 28 is each index graph of the fourth case.
Figure 29:
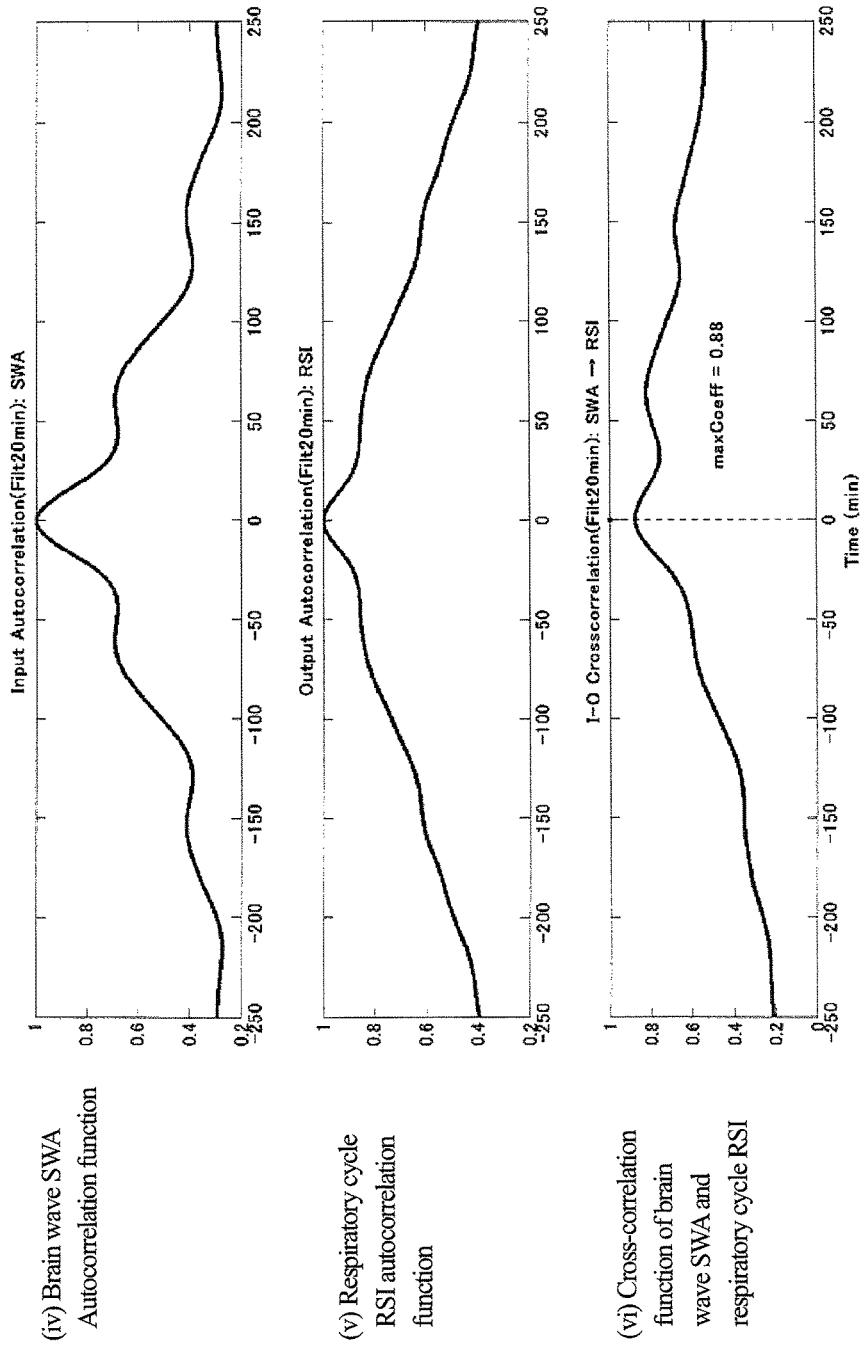
FIG. 29 is each index graph of the fourth case.
Figure 30:
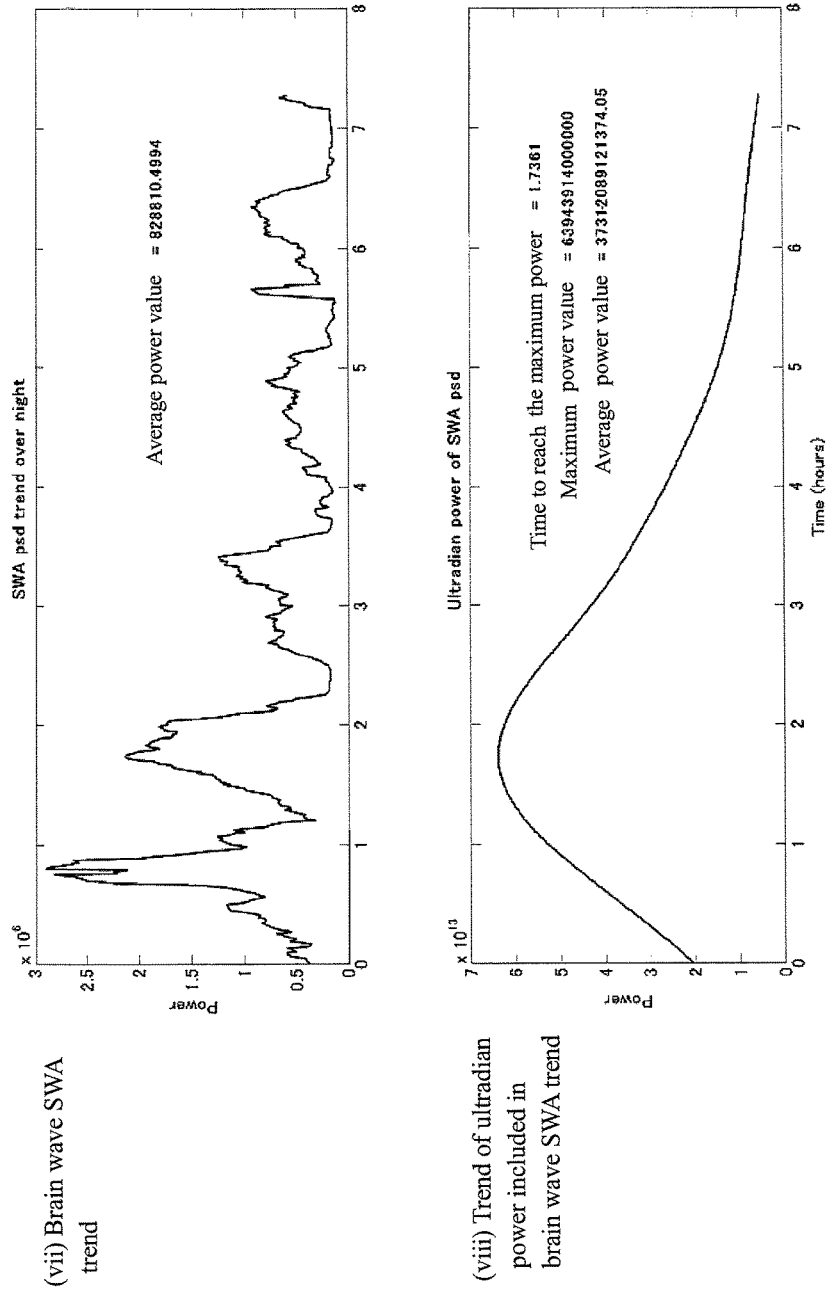
FIG. 30 is each index graph of the fourth case.
Figure 31:
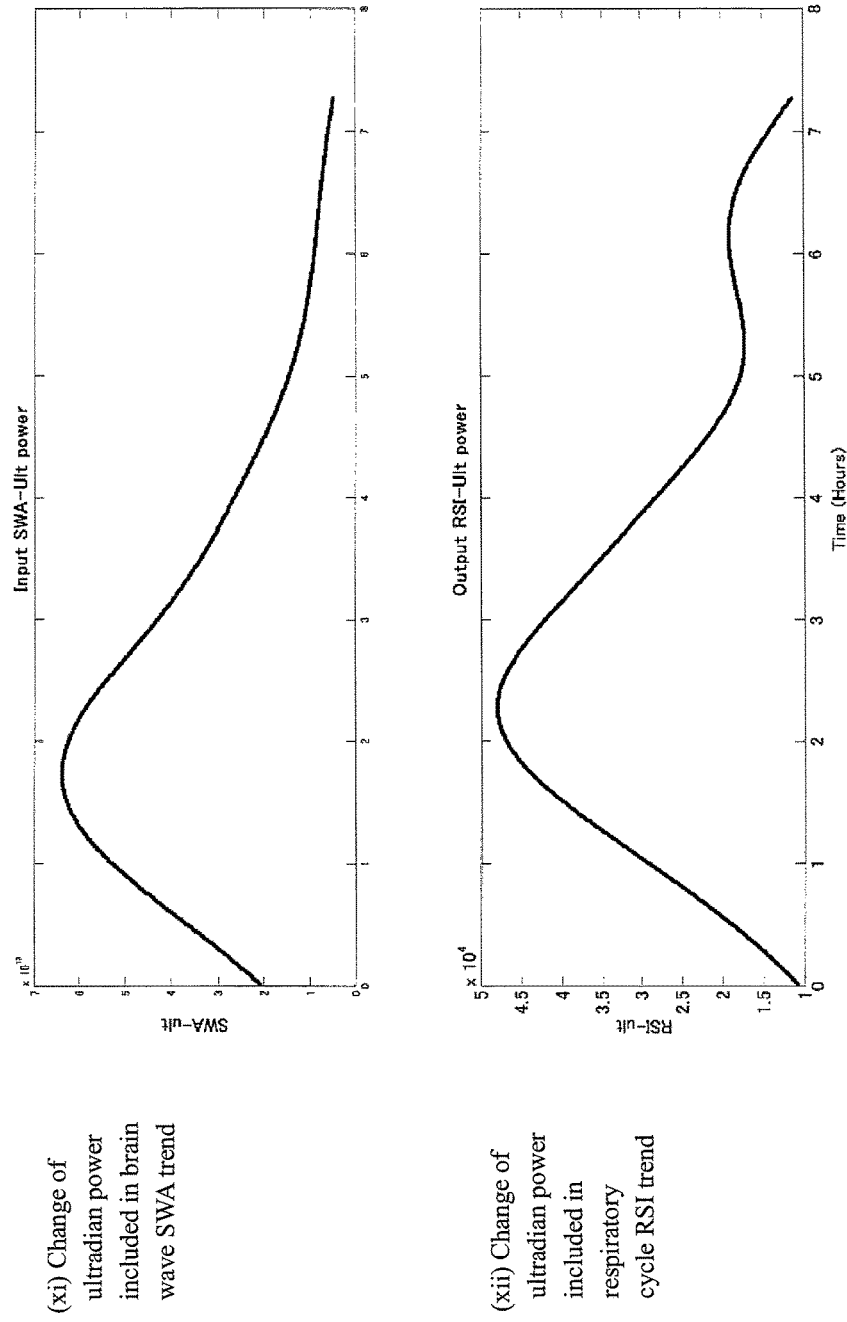
FIG. 31 is each index graph of the fourth case.

In FIG. 10 schematically illustrating a frequency spectrum of the respiratory operation cycle waveform mean lung power, for example, which is a frequency spectrum after extraction of the respiratory frequency, the frequency spectrum in a state in which sleep is deep, respiration of a subject is slow, displacement of the frequency is less, and a respiratory operation is stable is, as illustrated in a graph 10a, such that the width of shape of the envelope around the frequency average value fxbar-s is small, and the standard deviation thereof expressed as fSDs is considered to be also small.

On the other hand, in a state in which sleep is shallower, the respiratory operation becomes rapid, the respiratory frequency shifts to a higher frequency average value fxbar-r, and the fluctuation of the respiratory frequency also becomes larger and thus, the width of the envelope shape is widened, and the standard deviation fSD-r in this state also becomes larger.

Therefore, as described above, by examining a temporal change of RSI, which is an inverse number of the standard deviation, a regular period (graph 10a) and an irregular period (a graph 10b) as illustrated in FIG. 10 can be visually observed and diagnosed easily.

The above-described numerical values of the Fourier window periods are only exemplifications and capable of execution at other values as appropriate, and regarding the above-described method of calculating the RSI using the inverse number of the standard deviation, an index obtained by other calculating methods indicating regularity of the respiratory cycle can be also used, and they are also a part of the present invention.

Also, as illustrated in FIG. 10, it may be so configured that the SD, RSI and the like are calculated by using only the data from the peak to 95% of the respiratory frequency graph and the data of the lowest 5% is eliminated so as to suppress the influence of noises.

Moreover, as described above, in addition to display of each graph waveform over the entire sleep period for one night of a subject, it may be so configured that a medical staff specifies a time domain in which the staff wants the graph waveforms to be particularly enlarged and observed and can make the waveform of each graph in the time domain and a frequency distribution (spectrogram) of each waveform in the time domain displayed.

FIG. 11 is an example thereof, and since a medical staff observes each waveform over the whole region of sleep and selects a specific region with particularly large CSR, as illustrated in FIG. 11(2) in each waveform graph in the selected region for 300 seconds and as illustrated in FIG. 11(1), a spectrogram of each waveform in this selected time domain can be displayed. According to FIG. 11, it can be visually recognized easily that the spectral power of CSR is large from (1) and that the CSR waveform cyclically repeats increase/decrease from (2). That is, the CSR is found in the subject in this region.

Since the configuration of selecting a specific time domain by using operating means and displaying a spectrogram and a power waveform in that region as described above can be easily realized from a known technology, detailed description thereof will be omitted in order to avoid cumbersomeness.

[Wavelet Analysis]

Next, in the generated waveform on the basis of the respiratory waveform described above, a result of comparison and examination of cases particularly using RSI (Respiration Stability Index) will be described.

Prior to the description, in the analysis target waveform like RSI, a wavelet analysis, which is a mathematical method of accurately analyzing how the power of a specific frequency component such as ultradian rhythm or a basic physiological cycle of sleep (approximately 90 minutes) changes with time will be described as preparation.

As a traditional analysis method for an irregularly continuous signal system including a biological signal, Fourier analysis has been well known.

The Fourier analysis is, as disclosed in detail in the following known document 1, for example, an analysis in which a method of Fourier-series expansion of a function having a cycle is further expanded to a non-periodic function so as to express an arbitrary irregular continuous signal series by superposition including infinite order of a functional waveform having a periodicity of a sinusoidal waveform and self-similarity.

Known document 1: "Introduction to Digital Signal Processing" by Kennichi Kido, pp. 13 to 15, (issued on Jul. 20, 1985, by Maruzen)

That is, a function x(t) having time t present in an infinite interval on the time axis as a variable and a function X(f) having a frequency f present in an infinite interval on a frequency axis as a variable can be selected so that the following expression 1 and expression 2 hold, and these two expressions in this case are referred to as a Fourier transform pair, and X(f) is referred to as Fouier transform of x(t).

$$X(f) = \mathcal{F}[x(t)] = \int_{-\infty}^{\infty} x(t)\exp(-j2\pi ft)dt \quad \text{[Numerical expression 1]}$$

$$X(t) = \mathcal{F}^{-1}[X(f)] = \int_{-\infty}^{\infty} X(f)\exp(j2\pi ft)df \quad \text{[Numerical expression 2]}$$

That is, the Fourier transform pair indicates a relationship between x(t) and X(f) when the waveform x(t), which is a function of the time t, is expressed as a collection of complex exponential functions $\exp(j2\pi ft)$ of a complex amplitude X(f), which is a function of the frequency f (here, since the frequency domain is a complex region, the complex exponential function is used instead of a real sine function or a real cosine function). The Fourier transform indicated in the expression 1 is to acquire the frequency function from the time function and the Fourier inverse transform indicated in the expression 2 is to acquire the time function from the frequency function. That is, the function having the time domain as a variable region is converted to a function having the time domain as a variable region by means of the Fourier transform.

The Fourier analysis, which is an analysis method using the above-described Fourier transform, is to make frequency analysis of the function waveform as an analysis target in the entire variable region thereof, and thus, it is extremely effective in an analysis of a discontinuous signal, with which a tendency of localization on the time axis is not a problem, but as illustrated in the following known document 2, if it is used for an analysis of a discontinuous signal having a specific characteristic, there is a problem hard to be solved, and the wavelet analysis has been recently proposed as means of analyzing them.

Known document 2: "What is Wavelet Transform" by Michio Yamada, ("Mathematical Science", December 1992, pp. 11 to 14, Saiensu-sha Co., Ltd.)

According to the above known document 2, the Fourier spectrum, which is information in the frequency domain obtained by Fourier transform, has lost information relating to time, and thus, it is difficult to find a correspondence relationship between the spectrum and the local phenomenon.

For example, even if the frequency increases with time monotonically, it is impossible to determine the tendency of the frequency change only from the spectrum. Also, even if a clear power law of the spectrum appears only in the data having clear local similarity at each time, that is, in the vicinity of the respective times, if time with different similarity is mixed in the time series, the clear power law of the spectrum cannot be expected, and it is substantially impossible to determine the characteristics of similarity by the shape of the spectrum.

Such disadvantageous nature of Fourier transform is caused since it is a function whose integral kernel $\exp(j2\pi ft)$ is uniformly expanded.

Thus, a method of Fourier transform by limiting the transform target data to a local portion on the time axis (window Fourier transform) might be used, but due to the uncertainty principle of Fourier analysis, there is a problem that accuracy cannot be improved at the same time for time and frequency. That is, the window Fourier transform corresponds to a situation in which periodicity and similarity are both partly destroyed and localized.

On the other hand, in the Wavelet transform, Fourier transform is localized with some break-down of periodicity while the similarity is strictly maintained.

This wavelet transform does not have high frequency resolution but is extremely suitable for analysis of local similarity of data from the locality and similarity of the kernel function. The wavelet analysis can be considered a tool which replaces periodicity in the Fourier analysis by locality.

Specific procedures of the wavelet analysis will further be described in accordance with the description in the known document 2, and in a case of one dimension, one function $\varphi(t)$ is selected, and this is called analyzing wavelet or mother wavelet. Qualitative description of conditions which should be satisfied by this $\varphi(t)$ is "a function which attenuates far and sufficiently fast". As a specific example of the analyzing wavelets, a plurality of wavelets including Mexican Hat function have been proposed and actually used in analysis.

By using this analyzing wavelet, a function system (collection consisting of a large number of functions) with two parameters as in the following expression 3 is created and this is called wavelet:

$$\varphi^{(a,b)}(t) = \frac{1}{\sqrt{a}}\varphi\left(\frac{t-b}{a}\right), \quad \text{[Numerical expression 3]}$$

$$(a, b \in R, a \neq 0)$$

The wavelet is made of mutually similar functions and when compared with Fourier transform, a has a role in a period (an inverse number of frequency) but b is a parameter of time and there is no corresponding one in Fourier transform.

Continuous wavelet transform in the case where the parameters a and b are continuous can be considered to have used the above analyzing wavelet (Expression 3) as the integral kernel $\exp(j2\pi ft)$ in Fourier transform, and forward transform and inverse transform are present similarly to Fourier transform, which are expressed by the following expressions 4 and 5, respectively:

$$T(a, b) = \frac{1}{\sqrt{C_\varphi}} \int_{-\infty}^{\infty} \varphi^{(a,b)}(t)^* f(t)dt \quad \text{[Numerical expression 4]}$$

(The sign * indicates a complex conjugate number)

$$f(t) = \frac{1}{\sqrt{C_\varphi}} \int_{-\infty}^{\infty} \int_{-\infty}^{\infty} T(a, b)\varphi^{(a,b)}(t) \frac{dadb}{a^2} \quad \text{[Numerical expression 5]}$$

$$C_\varphi \equiv \int_{-\infty}^{\infty} \frac{|\varphi(\omega)|^2}{|2\pi f|} 2\pi df < \infty \quad \text{[Numerical expression 6]}$$

$$\left(\hat{\varphi}(2\pi f) = \int_{-\infty}^{\infty} \exp(-j2\pi ft)\varphi(t)dt\right)$$

Here, T(a,b) is called a (continuous) wavelet transform of the target function or analysis f(t), and also called "wavelet coefficient" in the following.

In the continuous wavelet transform, an expression similar to the relationship of Parseval in Fourier analysis holds, and the following isometric form, that is, the following expression 7, which is a relational expression of the "equi-partition law of energy" holds:

$$\int_{-\infty}^{\infty} |f(t)|^2 dt = \int_{-\infty}^{\infty} \int_{-\infty}^{\infty} |T(a, b)|^2 \frac{dadb}{a^2} \quad \text{[Numerical expression 7]}$$

From this expression 7, it is possible to discuss the characteristics of a time series by defining that the "energy of a component of the frequency 1/a at time b" is $|T(a, b)|^2$. Also, such a use can be considered that $|T(a, b)|^2$ (this is referred to as "power") is displayed on an ab plane as a bird's eye view or a color plot, for example, and various phenomena included in the time series can be classified by using patterns found therein.

That is, by applying the wavelet transform to the waveform to be analyzed, wavelet coefficients corresponding to the respective points in two variable spaces, which are the frequency 1/a and the time b, are calculated, and by using these wavelet coefficients, power can be calculated as an index of energy with respect to each frequency 1/a and the time b.

Also, in the following known document 3, an application of the wavelet analysis or particularly a discontinuous signal detection function is described.

Known document 3: "Wavelet Analysis~Birth/Development/Application" by Ryuichi Ashino, Shizuo Yamamoto, pp. 23 to 25 and 131 to 133 (issued on Jun. 5, 1997, Kyoritsu Shuppan Co., Ltd.)

Considering an application of the wavelet analysis, the most important function is detection of a discontinuous signal. Discontinuous signals found in natural phenomena are extremely small and moreover, covered by noises. The wavelet transform has a capability to detect this discontinuity of signals. This is because an absolute value of the wavelet coefficient at a discontinuous point on the time axis is larger than the other points, and the discontinuous point can be detected.

As described above, the wavelet analysis is considered to act effectively for analyses of complex discontinuous signal waveforms in which various frequency components are superimposed with a localization tendency, and the inventor has paid attention to this point and reached the finding described below and the present invention.

[Cases]

Results of comparison using RSI and ultradian rhythm power changing waveforms and other analysis results for two case groups or four cases in total will be described below. The two case groups are as follows:

Case Group I (Healthy Group)
Number of cases: 1 (first case, FIGS. 12 to 16)
Cardiac diseases: None
Remarkable CSR
None
Quality of sleep: Favorable
Case group II (disease group)
Number of cases: 3 (second case, FIGS. 17 to 21, third case, FIGS. 22 to 26, and fourth case, FIGS. 27 to 31)
Cardiac diseases: Chronic heart failure
Remarkable CSR: Yes
Quality of sleep: Unfavorable The pathosis of the cases included in the case group II (disease group) is as follows:
Second case: NYHA Class I, BNP=47 pg/ml
Third case: NYHA Class II, BNP=115 pg/ml
Fourth case: NYHA Class III, BNP=1000 pg/ml Here, NYHA is classification of the degree of a heart failure symptom determined by New York Heart Association (NYHA), and the severity of heart failure is classified into four classes as follows:

NYHA Class I: No symptoms and no limitation in ordinary daily life.
NYHA Class II: Slight to medium limitation in daily life. No symptoms at rest but fatigue/palpitation/shortness of breath and/or angina occurs in usual behaviors.
NYHA Class III: Marked limitation in daily life. No symptoms at rest but symptom occurs even during less-than-ordinary activity such as walking on a flatland.
NYHA Class IV: Some symptoms even in extremely light activity. Symptoms of heart failure/angina might occur even at rest.

Also, the BNP test (brain natriuretic peptide) is a test for measuring an amount of hormone secreted from the heart (mainly from the ventricles) into blood if a burden is applied to the heart, and the higher this BNP value is, the larger burden is considered to be applied to the heart. Clinically, this test is useful for diagnosis/prognostication of cardiac infarction or heart failure and the only test that can measure cardiac diseases by blood test.

Ascertainment of heart disease pathosis using the BNP test value is as follows:
18.4 pg/ml or less: Within a standard range.
18.5 ph/ml or more: Exceeding the standard range. The value rises in accordance with deterioration of the pathosis.

Also, in FIGS. 12 to 31 for explaining each case, the following graphs explaining the characteristics of the present invention are illustrated in common to each case:

(i) Brain wave SWA trend: A trend graph of data obtained by calculating the above-described SWA from the brain waves for 5 minutes and by repeatedly executing it up to 8 hours by shifting by 50 seconds. Therefore, the sampling frequency of this graph is 50 seconds each (0.02 Hz).

(ii) Respiratory cycle RSI trend: A trend graph of data obtained by calculating the above-described RSI from the respiratory curve for 5 minutes and by repeatedly executing it up to 8 hours by shifting by 50 seconds. Therefore, the sampling frequency of this graph is 50 seconds each (0.02 Hz).

An envelope obtained by filtering the waveform is added to both (i) and (ii) so that the rhythm of the waveform trend can be easily seen.

(iii) Frequency distribution of brain wave SWA and respiratory cycle RSI

Frequency analysis by MEM (Maximum Entropy Method) is applied to the data of SWA and RSI (0.02 Hz) for approximately 8 hours, and major vibration components included in these time-series signals are extracted. Emphasis is placed on grasping of the frequency domain, which is normalized by the respective maximum power in illustration.

(iv) Brain wave SWA autocorrelation function

The autocorrelation function of the above SWA waveform, that is, a change of the correlation coefficient by shifted comparison between SWA waveforms is illustrated. Presence of an important rhythm latent in the waveform is to be statistically demonstrated.

In order to clarify description by omitting duplicated illustrations, (xi) and (xii) are omitted in the first case and (ix) and (x) are omitted in the second to fourth cases.

(v) Respiratory cycle RS autocorrelation function

Similarly, the autocorrelation function of the RSI waveform, that is, a change of the correlation coefficient by shifted comparison of the RSI waveforms is illustrated.

(vi) Mutual correlation functions of brain wave SWA and respiratory cycle RSI

A change of the correlation coefficient by shifted comparison of the SWA waveform and RSI waveforms is illustrated. This is a graph which statistically demonstrates whether or not the correlation between the both is high.

(vii) Brain wave SWA trend

The waveform in (i) is made into a continuous waveform.

(viii) Change of ultradian power included in brain wave SWA trend

A change of the ultradian rhythm power included in the waveform of (vii) is illustrated in a graph using the above-described wavelet analysis method. That is, an average value of power at 0.0001 to 0.0003 Hz (90-minute cycle) is tracked, and a change of the depth of sleep is illustrated.

(ix) Respiratory cycle RSI trend

The waveform in (ii) is made into a continuous waveform.

(x) Change of ultradian power included in respiratory cycle RSI trend

A change of the brain wave SWA ultradian rhythm power included in the waveform of (ix) is illustrated in a graph using the above-described wavelet analysis method. That is, an average value of power at 0.0001 to 0.0003 Hz (90-minute cycle) is tracked, and a change of the depth of sleep is illustrated.

(xi) Change of ultradian power included in brain wave SWA trend

The same as (viii).

(xii) Change of ultradian power included in respiratory cycle RSI trend

The same as (x).

From each of the graphs (i) to (xii) relating to the first to fourth cases, the following points are found:

First, from (i) and (ii), it is clearly seen that the time phases of the brain wave SWA trend and the respiratory cycle RSI trend match each other. Similarly, from this data, it is understood that respiration is regularly stabilized when a certain depth of sleep is obtained, and the regularity of respiration is constant (the regularity has reached the upper limit) even if the sleep gets deeper. It is predicted that there is an SWA threshold value for RSI to become regular during sleep. That is because the RSI does not react when the rightmost SWA peak appears in the first case.

Subsequently, from (iii), the ultradian rhythm of 0.0001 to 0.0003 Hz (approximately 90 to 100 minute cycle) is clearly found in both of the brain wave SWA trend and the respiratory cycle RSI trend.

Also, from (iv), (v), and (vi), it is found that in the autocorrelation function, both the brain wave SWA trend and the respiratory cycle RSI trend have periodicity and that the cycle is approximately 90 to 100 minutes from the peak interval of the autocorrelation function waveform and matches the ultradian rhythm. The maximum correlation of the both in the mutual correlation function shows a high value of approximately 0.9, which means that the both are closely related to each other.

The most important point to be noted is that the periodicities of the ultradian rhythm included in the brain wave SWA trend and the respiratory cycle RSI trend are larger in healthy people and that as the NYHA class proceeds and the cardiac disease becomes more serious, expression of the periodicity becomes small. That can be known from a difference in the size of a peak found in the autocorrelation function of the respective trend waveforms.

Also, if the data of a healthy person asleep (first case) is compared with the data of a patient with a heart failure (second to fourth cases), the respective features of the brain wave SWA and the respiratory cycle RSI are found, and the following interesting characteristics can be understood:

The brain wave SWA increases its power in accordance with the depth of sleep, but the respiratory cycle RSI is expected to have something like a threshold value at which regularity in the sleep at the depth not less than a certain level becomes clear. This is because the respiratory cycle RSI becomes suddenly regular at some degree of sleep and cannot be more regular than that (regularity has an upper limit value).

Therefore, since the size of the peak in the respiratory cycle RSI becomes constant at some degree or more, it is likely that the maximum value cannot be found easily with the wavelet analysis as in the brain wave SWA.

Particularly in the case of deep sleep throughout the night as in a healthy person, the wavelet of the respiratory cycle RSI is considered to easily show the ultradian power like a wide trapezoid (first case).

Rather, the respiratory cycle RSI is considered to easily show a peak, matching deep sleep sometimes found in a seriously-ill patient with sleep disorder (second and third cases).

From the above, the respiratory cycle RSI is considered to sharply reflect deep sleep at a certain level or more (non-REM sleep, requiring comparison with the depth).

The above consideration was made based on a comparison between the brain wave SWA trend and the respiratory cycle RSI trend of each case as a main viewpoint.

Next, attention is paid to a change of the respiratory cycle RSI trend of each case and the ultradian rhythm power included therein, and a difference between the case group I (healthy group) and case group II (disease group) will be considered.

If these two groups are compared based on the viewpoint of the change in the illustrated RSI and ultradian rhythm power, the following differences between the groups are marked. Therefore, by using the RSI, a change in the ultradian rhythm waveform or both, it is possible to discriminate between the "group without chronic heart failure or marked CSR and with a favorable quality of sleep" and the "group with chronic heart failure and marked CSR and a unfavorable quality of sleep" by diagnosis.

Particularly clear differences are as follows:

TABLE 1

| Difference | Case group I | Case group II |
|---|---|---|
| Position of RSI peak | Clear in the first half of sleep. A peak is found in 1.5- to 2-hour cycle, and 3 to 4 peaks are found during the sleep | Only irregular peaks are found. Not synchronized with the cycle of typical good-quality sleep at all. |
| Size of RSI | The value of a peak is large. A time integral value is also large. | A peak is small and a time integral value is also small. Particularly in the fourth case, both are markedly small. |
| Peak position of ultradian rhythm power | Continuous peak is found in the first half of sleep. | There is no continuous peak and there are even cases without clear peaks. |
| Size of ultradian rhythm power | Relatively large. | Relatively small. |

[Change of Index by Administration of Oxygen]

At the end of the description using the cases, the fifth case will be described using FIGS. 32 and 33.

This fifth case is affected with a chronic heart failure, marked Cheyne-Stokes respiration is found, and the quality of sleep is poor.

Figure 32:
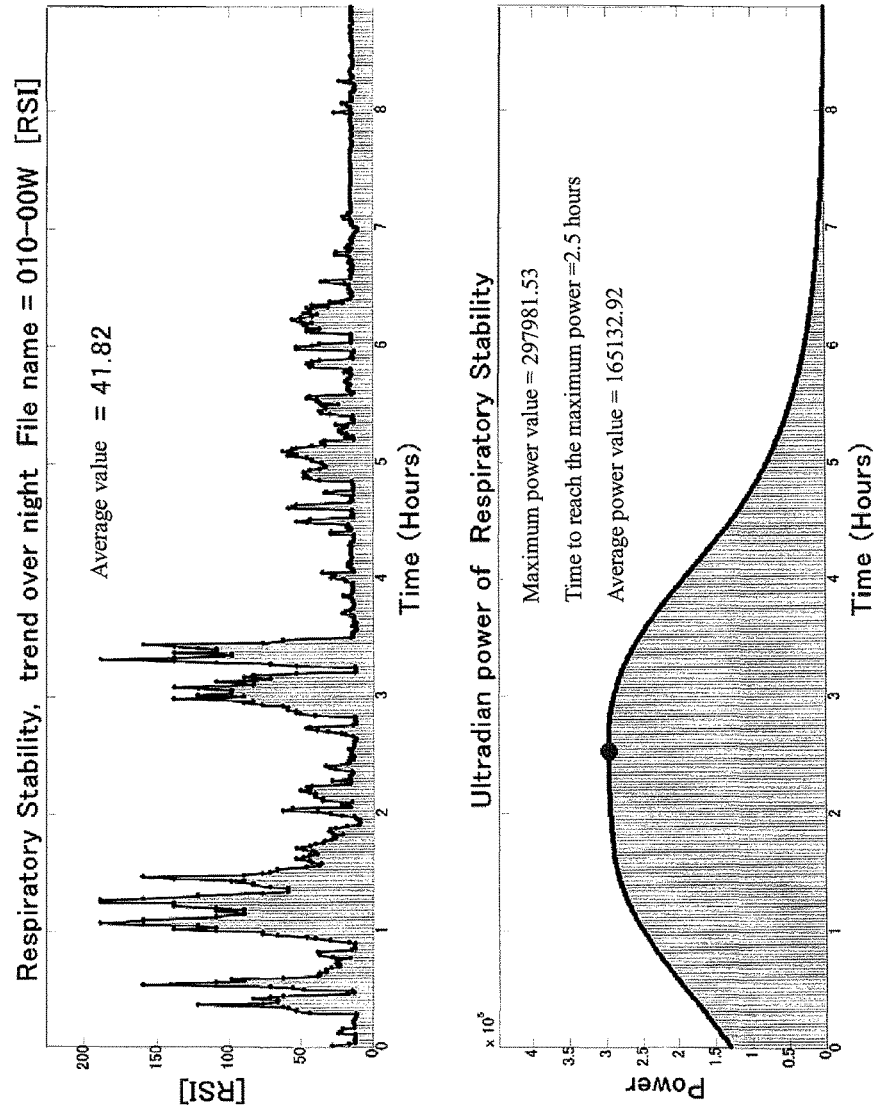
FIG. 32 is each index graph of a fifth case.

FIG. 32 illustrates a change during the sleep of the RSI and the ultradian rhythm of this fifth case patient before administration of an oxygen treatment.

Figure 33:
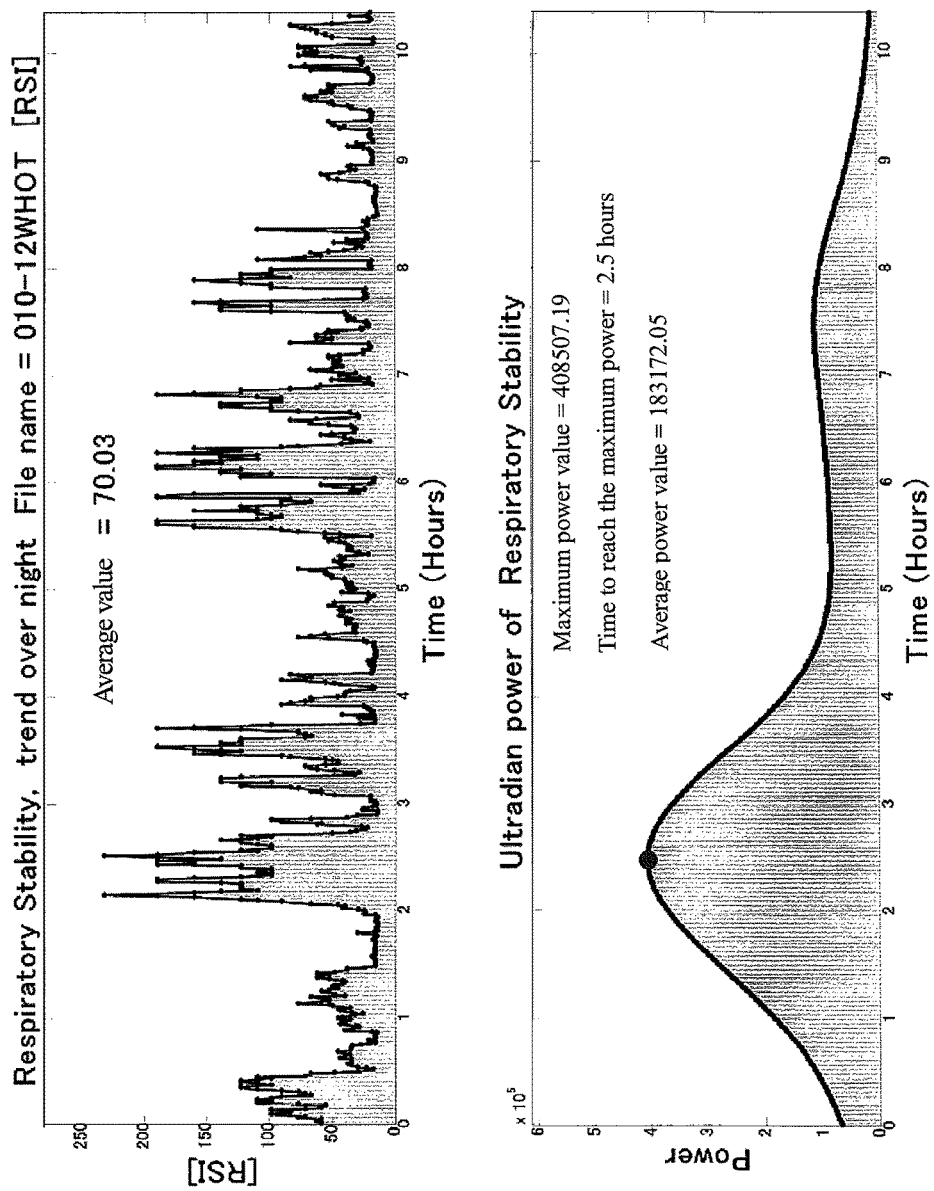
FIG. 33 is each index graph of the fifth case.

FIG. 33 also illustrates a change during the sleep of RSI and the ultradian rhythm of the fifth case patient after the oxygen treatment is started in which 90% oxygen is continuously administered.

By comparing FIGS. 32 and 33, it is clearly understood that after the oxygen administration is started, the value of RSI increases and also, a time domain in which the value of RSI is markedly large, that is, a time domain in which the respiratory cycle of the patient is stable and the sleep is deep is expanded as compared with that before the administration.

Moreover, similarly by comparing the both figures, it is understood that the size of the ultradian power increased than that before the administration, and it is also understood from this point that the quality of sleep of the patient has improved by the oxygen administration.

[Variation No. 1—Application to Telemedicine]

In putting the present invention into practice, there can be various variations other than the above embodiment.

For example, instead of the configuration in which a respiratory waveform is measured and recorded by a portable respiratory waveform measuring device and then conveyed to a medical institution, the present invention can be put into practice in a telemedicine system in which the respiratory waveform is directly transmitted to an analyzing device via a communication path or by a configuration in which not only a change of each frequency component in the respiratory waveform is displayed but automatic evaluation is made (however, definite diagnosis is made by a medical staff) in a screening manner in accordance with the number, size, clarity or position of peaks.

[Variation No. 2—Display of Change of Respiratory Frequency Stability]

Next, a configuration having a particular importance as a variation of the system in the present invention will be described.

The inventor has obtained the following finding in making sleep evaluation diagnoses of a large number of cases by using respiratory waveform measurement information of subjects as above.

As described above, in the sleep, 6 types of sleep stages are typically repeated with a 90-minute cycle three times for one night, and a change in the physiological data in each cycle can be clearly observed by the SWA (Slow Wave Activity) of the brain wave as follows. It is known that, in the case of a subject whose comfort level including the quality of sleep has lowered due to some cause such as apnea, the cycle in the sleep stages in the SWA breaks down and cannot be clearly observed.

Thus, a respiratory operation of a subject during sleep is focused, and by paying attention to variation in the respiratory cycle obtained by measurement or particularly in the stability of the respiratory cycle, it is likely that observation of this sleep cycle and hence, evaluation of the comfort level including the quality of sleep can be performed.

The stability of the respiratory cycle can be indicated in the following manner: a band of a respiratory cycle is extracted from the respiratory waveform obtained by measurement; first, an average value (X bar) of the respiratory frequency is calculated; second, a standard deviation (Sd) of the respiratory frequency is calculated by using a known statistical method; and an inverse number of this standard deviation (Sd) is calculated.

Similarly to the above-described embodiment, the inverse number of the standard deviation of measured respiratory waveform is called RSI (Respiration Stability Index) here. By forming a graph from this RSI so that a temporal change in sleep for one night is known, medical staff should be able to easily determine through observation if the sleep cycle is clearly exhibited and the comfort level including the quality of sleep is good or if the sleep cycle cannot be clearly observed and the comfort level including the quality of sleep is poor.

Thus, in the system of the variation in the present invention, the configuration in which, from the inputted respiratory waveform, a frequency band of 0.1 to 0.5 Hz including 0.4 Hz, which is a typical respiratory cycle of a human body, is extracted from a plurality of Fourier spectra at the time which becomes a start point of each Fourier window period obtained by executing fast Fourier transform (FFT) by shifting time by 5 seconds in the Fourier window period of 5 minutes is the same as the above-described configuration.

Moreover, in the system of the variation in the present invention, the analysis part 3-3 calculates the average value (X bar) and the standard deviation (Sd) of the frequency included in the respiratory frequency band for each Fourier window obtained with the shift interval of 50 seconds, creates a graph indicating a temporal change of the RSI in which the RSI, which is an inverse number of this Sd, is calculated for each Fourier window period having this 50-second shift interval and plotted on the axis orthogonal to the time axis and displays, prints or outputs this to the outside as information of the calculation result.

By observing this graph of RSI, clarity of the sleep cycle and hence the comfort level including the quality of sleep can be easily observed and diagnosed.

[Variation No. 3—Device which Automatically Evaluates Comfort Level Including Quality of Sleep]

The above-described variation is a method in which the index RSI indicating the regularity of the respiratory cycle is calculated from an inverse number of the standard deviation of the respiratory frequency and a like and a temporal change of this RSI is displayed so that a medical staff observes and diagnoses it.

However, since a trend graph of the RSI in the case where the comfort level including the quality of sleep is good and the sleep cycle is clearly exhibited is known, it is possible to automatically determine the comfort level including the quality of sleep from the obtained SRI trend graph.

Specifically, they include the size of a peak of the RSI graph, an area held by the graph with the time axis, that is, a time integral value of the RSI graph, predicted RSI trend graph rising time, that is, deviation from the start time of a respiratory stability period, a figural displacement amount from a geometrical numerical value from the RSI graph in the case where the comfort level including the ideal quality of sleep of the subject or a general subject is good and the like. Others may be also used.

From these approaches, by using the configuration of the sleep evaluation system 1 in the present invention, a configuration of automatic evaluation of the comfort level including the quality of sleep can be easily reached, and detailed description of the specific configuration will be omitted.

Next, as another variation of the present invention, an example in which the sleep evaluating technology on the basis of the above-described respiratory waveform analysis is specifically applied to a treatment device used for a treatment of a patient will be described.

[Variation No. 4—Embodiment of the Invention Relating to Airway Positive-Pressure Respiratory Assisting Device]

First, an embodiment in which the present invention is applied to an airway positive-pressure respiratory assisting device, which is a treatment device for sleep apnea syndrome (hereinafter SAS) caused by airway obstruction (hereinafter also referred to as "CPAP device" or "respiratory assisting device"), will be described.

In the example relating to the CPAP device which will be described below, feeding-out pressure control of a gas to be supplied to a patient is executed by a control unit provided inside the device.

A configuration in which a device which supplies a gas to a patient and a device which controls the supply pressure are not formed integrally but provided separately has been already introduced into the market. Thus, other than the configuration in which a function unit which supplies a gas and a function unit which executes supply pressure control are integrally provided inside the CPAP device as will be described below, the supply control may be executed by a separate device, and the configuration will be described below by also including such a variation in the range.

The CPAP device is an airway positive-pressure respiratory assisting device in which the pressure of atmospheric air is boosted by approximately 30 cmH$_2$O and supplied to a nasal cavity unit by using a nasal mask as a respiratory auxiliary means.

In detail, this is a medical instrument provided as one method of treatment means for sleep apnea syndrome, in which a boosted air is fed into the respiratory airway through the nasal cavity unit, the inside of the airway is maintained at a positive pressure and the respiratory airway is made to flow through the airway in order to prevent drop in oxygen concentration in the blood due to respiratory arrest caused by obstruction of the airway unit. Specific configuration of the CPAP device is disclosed in Japanese Patent Laid-Open No. 7-275362, for example.

The sleep apnea syndrome (SAS) is a collective name for a disease in which apnea is intermittently repeated during sleep and as a result various symptoms such as daytime somnolence are presented.

The apnea is defined as airway arrest for 10 seconds or more, and regarding SAS, in the case of apnea of 30 times or more during sleep for 7 hours for one night, if an apnea index AI (number of times of apnea per 1 hour of sleep) is AI≥5 (times/hour) or in actual clinical use, apnea hypopnea index (AHI) in which hypopnea is added to apnea is used. Apnea hypopnea index: the number of times of apnea and hypopnea added together per hour of sleep.

Hypopnea: a state in which airway is not completely closed but made narrow and a ventilation amount becomes small. Drop of ventilation by 50% or more accompanied by drop of oxygen saturation (SpO2) by 3% or more.

SAS is classified by the causes into obstruction type (also referred to as occlusive) (Obstructive Sleep apnea=OSA, upper airway is obstructed during sleep and the airway is arrested, and respiratory motions of a chest wall and an abdominal wall are found even during apnea, but a paradoxical motion in which the motions are opposite to each other is shown), center type (also referred to as central) (Central Sleep apnea=CSA, due to functional abnormality of the respiratory center, stimulus to a respiratory muscle is lost during sleep mainly in the REM period and becomes apnea), and a mixed type of OSA and CSA (starts with the central apnea and moves to obstructive apnea in the second half in many cases. Often classified as one of obstructive apnea.).

Patients to be treated by the CPAP device among them are OSA patients.

OSA develops since apnea or hypopnea occurs due to occlusion of an upper airway.

The causes of the occlusion are (A) morphological abnormality (fat deposition on the airway due to obesity, swollen amygdala, macroglossia, deviation of the nasal septum, adenoid, micrognathia (jaw is small) and the like) and (B) functional abnormality (the force to maintain muscles constituting the airway is lowered).

Deep sleep (non-REM sleep) is found at the beginning of the sleep pattern of healthy people but in the OSA patients, oxygen in blood decreases due to apnea, the intrapleural pressure becomes negative, an arousal reaction occurs repeatedly during sleep, and deep sleep cannot be obtained, and thus, symptoms such as daytime somnolence are presented.

For such OSA patients, the CPAP device feeds air with a certain positive pressure through a nasal mask and expands the upper airway and as a result, performs an operation of preventing apnea by solving the airway obstruction. The pressure to expand the airway (hereinafter also referred to as a "positive pressure") differs depending on the patients.

For respiratory attenuation such as CSA characteristically found in specific diseases such as heart failure, other than CPAP which maintains a certain level of pressure (positive pressure) of compressed air applied to the patient's airway, auxiliary artificial respiratory devices such as a device which has two different pressures, respectively, for the expiratory period and the inspiratory period of the patient (referred to as Bilevel-PAP) and such as a device which monitors the respiratory state of the patient (presence, airflow level, interval and the like) all the time and applies an optimal pressure while changing it every moment (referred to as servo-type automatically controlled auxiliary ventilation) might be used, and the optimal pressure is different depending on the patients or symptoms.

Whichever the method is, the positive-pressure level is determined as prescription on the basis of a doctor's findings. Such a configuration that the comfort level including the quality of sleep of the treatment target patient is directly evaluated and the optimal positive-pressure level is determined in order to keep favorable comfort level including the quality of sleep has not been known.

Figure 34:
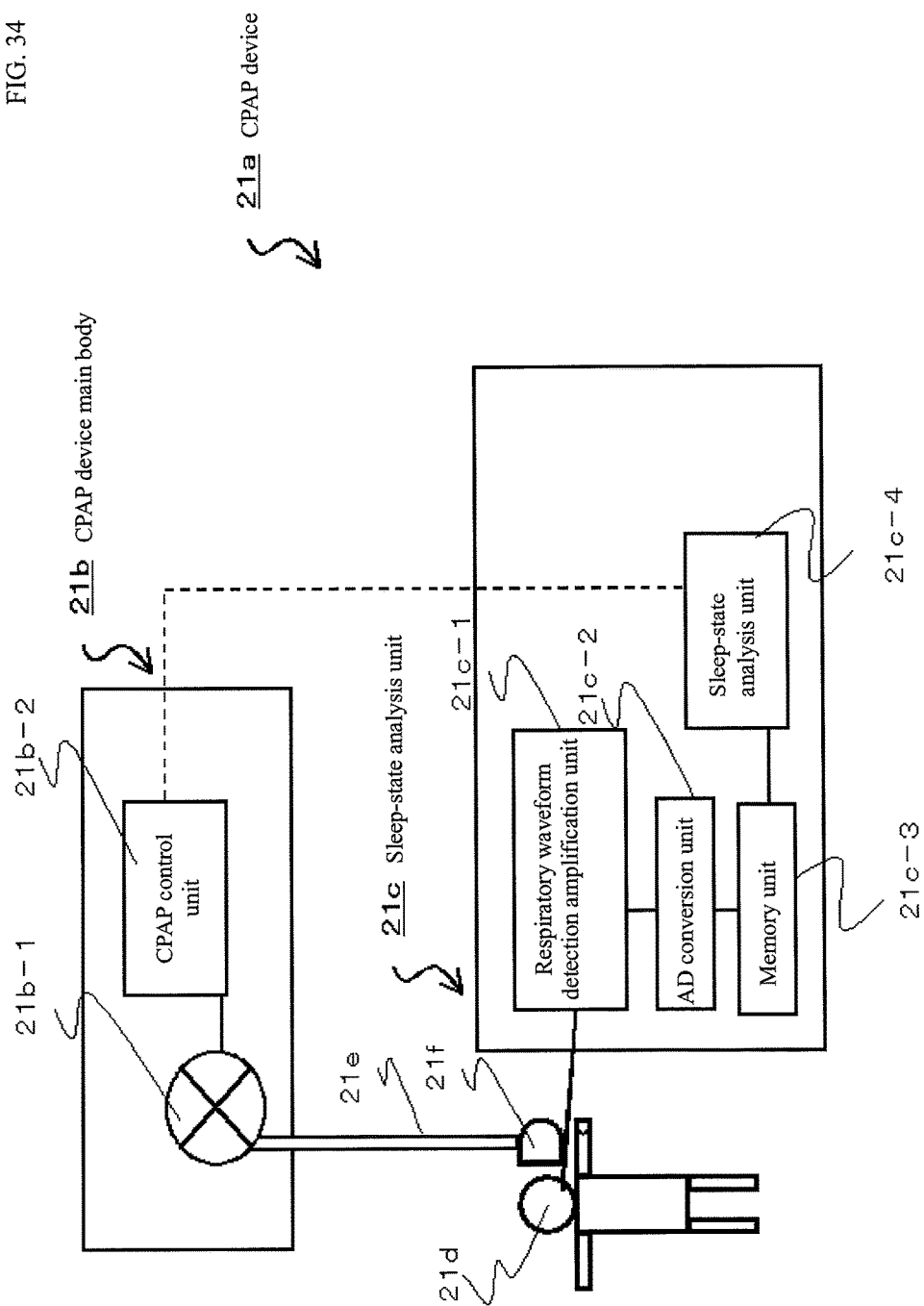
FIG. 34 is a configuration diagram of a CPAP device according to the present invention.

In order to solve these prior-art problems, a CPAP device 21a in this embodiment has, as illustrated in FIG. 34, the following configuration.

First, a CPAP device main body 21b is a device configured capable of variable control of the positive-pressure level and has a blower 21b-1 which generates compressed air and feeds it out to the outside of the device and a CPAP control unit 21b-2 which executes operation control of the CPAP device main body 21b including change control of the pressure (positive-pressure level) of the compressed air fed out by the blower 21b-1.

The compressed air (positive-pressure air) fed out of the CPAP device main body 21b is supplied through a mask 21f via a duct 21e into the airway of the patient.

For the configuration of the CPAP device main body 21b, the already disclosed prior-art configuration can be used except the characteristic configuration described below.

A respiratory sensor 21d has the configuration similar to the respiratory sensor in the sleep evaluation system 1.

A sleep state analysis unit 21c is provided separately from or integrally with the CPAP device main body 21b and has a respiratory waveform detection amplification unit 21c-1 which receives and amplifies the output of the respiratory sensor 21d, and AD conversion unit 21c-2 which digitalizes the analog output, a memory unit 21c-3 which accumulates information of the digitalized waveforms so as to be made accessible, and a sleep state analysis unit 21c-4, which will be described below.

The sleep state analysis unit 21c-4 can obtain the digitalized signal of the detected waveform inputted form the respiratory sensor 21d as above, sequentially execute Fourier transform in the Fourier window period, and create a temporal change of an extracted signal of a respiratory frequency band and of the RSI obtained therefrom on a real-time basis.

The operation principle of the CPAP device 21a of this embodiment is as follows.

In the sleep, 6 types of sleep stages are typically repeated with a 90-minute cycle three times for one night, and a change in the physiological data in each cycle can be clearly observed by the SWA (Slow Wave Activity) of the brain wave as follows. It is known that, in the case of a subject whose comfort level including the quality of sleep has lowered due to some cause such as apnea during sleep, the cycle in the sleep stages in the SWA breaks down and cannot be clearly observed.

Thus, a respiratory operation of a subject during sleep is focused, and by paying attention to variation in the respiratory cycle obtained by measurement or particularly in the stability of the respiratory cycle, it is likely that observation of this sleep cycle and hence, evaluation of the comfort level including the quality of sleep can be performed.

The stability of the respiratory cycle can be indicated in the following manner: a band of a respiratory cycle is extracted from the respiratory waveform obtained by measurement; first, an average value (X bar) of the respiratory frequency is calculated; second,; a standard deviation (Sd) of the respiratory frequency is calculated by using a known statistical method, and an inverse number of this standard deviation (Sd) is calculated.

Similarly to the above-described embodiment, the inverse number of the standard deviation of measured respiratory waveform is called RSI (Respiration Stability Index) here. By forming a graph from this RSI so that a temporal change in sleep for one night is known, medical staff should be able to easily determine through observation if the sleep cycle is clearly exhibited and the comfort level including the quality of sleep is good or if the sleep cycle cannot be clearly observed and the comfort level including the quality of sleep is poor, and at the same time, by controlling the pressure of the positive-pressure air using the configuration of the above-described automatic evaluating device of the comfort level including the quality of sleep so that the obtained temporal change of the subject's RSI gets closer to the temporal change in the good-quality sleep, the positive-pressure air is supplied to the patient under the optimal CPAP treatment condition in accordance with the individual patients or in accordance with the state of the day of the patient, and the optimal sleep state can be obtained.

This positive-pressure level control is effective if feedback control is executed. Regarding the sleep-state analysis unit 21c-4 and the CPAP control unit 21b-2, analysis and a change of the positive-pressure level may be performed at a single or a plural time points during sleep or the control may be continued so that the optimal positive-pressure level is obtained on the real time basis by monitoring the time changing waveform of the RSI all the time.

Also, this positive-pressure level control may be executed either in a method in which the control is executed only as a test for determining the positive-pressure level of the patient in that case only or in a method in which the control is executed all the time if the OSA patient is treated using this CPAP device 21a.

As a target patient for whom treatment is given by using the CPAP device 21a, a patient with sleep apnea syndrome was described above similarly to the case where the CPAP device having the prior-art configuration was employed.

On the other hand, the CPAP device 21a, with the characteristics in the configuration according to the embodiment of the present invention, can expand the target to a patient with chronic heart diseases or particularly to a patient with heart failure in addition to the above patient with sleep apnea syndrome.

That is, the treatment using Bilevel-PAP assisting a respiratory pump function for a patient with chronic heart diseases or particularly for a patient with heart failure is known to improve hemodynamics.

However, the patients with chronic heart diseases have excessively elevated sympathetic nerve activity due to the heart failure or the like, that is, in an excited state, and many of them have disorder of initiating sleep, and in such a situation, the Bi-PAP treatment requiring attachment of a mask might further deteriorate the comfort level including the quality of going to sleep, and long-term use thereof has tended to be avoided.

In order to solve that situation, by using the CPAP device 21a of this embodiment, a result of the respiratory waveform analysis can be fed back, and the pressure level and the pressure waveform are adjusted so that night use is made possible, thereby realizing long-term treatment.

Next, in an airway positive-pressure respiratory assisting device of this embodiment, unlike the CPAP device whose pressure applied to a patient is constant or the Bilevel-PAP having only two phases of pressure change, if it is configured on the basis of a servo-type automatic control auxiliary ventilator (Adaptive Servo Ventilator: ASV) which executes automatic control so that both of or either one of the pulmonary ventilation and the respiratory frequency of a patient gets closer to a predetermined amount set in advance by applying an optimal pressure for the moment while changing it and monitoring the state of the respiration of the patient (presence, airflow level, interval and the like) all the time, the advantage of the present invention is further improved, which will be described below.

In normal respiration (8 to 15 times a minute), the heart beat increases in inspiration and decreases in expiration. Since this respiratory sinus arrhythmia (change in the heart beat caused by respiration) completely disappear if the heart vagus nerve is blocked by atropine, it is understood that the heart vagal activities are mainly involved.

One of the causes that the vagal activities are weakened in synchronization with the inspiration phase is the central mechanism in which the heart vagal activities are suppressed by interference from the respiratory center (Hamlin R L, Smith C R, Smetzer D L. Sinus arrhythmia in the dogs. Am J Physiol 1966; 210:321-328. Shykoff B E, Naqvi S J, Menon A S, Slutsky A S. Respiratory sinus arrhythmia in dogs. J Clin Invest 1991; 87: 1612-1627.).

This is based on the fact that the increase in the heart beat in synchronization with the activities of the diaphragmatic nerve in inspiration is found even if there is no motion in lungs or thoracic cage.

On the other hand, as a peripheral mode which causes the respiratory heart beat fluctuation, gating effects are known in which the vagal nerve activities are blocked in synchronization with the inspiration due to afferent input from stretch receptors of the lungs. In fact, in a patient with lung implant in which the vagal efferent is maintained but the vagal afferent from the lungs are blocked, it is known that the respiratory heart beat fluctuation clearly weakens (Tara B H, Simon P M, Dempsey J A, Skatrud J B, Iber C. Respiratory sinus arrhythmia in humans: an obligatory role for vagal feedback from the lungs. J Appl Physiol 1995; 78: 638-645.).

Therefore, as described above, in the CPAP device which executes control by using the respiratory pressure as an index, if a cycle or a ventilation amount of a respiratory operation of a treatment patient is not constant but fluctuates in a sleep process, it might affect a change of the respiratory frequency.

However, in the servo-type automatic control auxiliary ventilator, as described above, since the control is executed so that both of or either one of the pulmonary ventilation and the respiratory frequency of the patient gets closer to a predetermined amount set in advance by applying an optimal pressure for the moment while changing it and monitoring the state of the respiration of the treatment patient (presence, airflow level, interval and the like) all the time, if this servo-type automatic control auxiliary ventilator is used, the control using the ventilator is made possible so that fluctuation in the operation cycle or the pulmonary ventilation in the respiratory operation of the patient in sleep becomes relatively smaller.

Therefore, if the airway positive-pressure respiratory assisting device of this embodiment having the above-described characteristics is configured based on the servo-type automatic control auxiliary ventilator, the control can be performed by using an index indicating regularity of the respiratory cycle of the patient or the temporal change of the RSI, for example, so that the comfort level including the quality of sleep can be improved. Since the control loop is formed only via the respiratory frequency of the patient, the control is direct and response to the control is improved. As a result, a sleep evaluation result with higher accuracy is obtained and the control using the result can be realized, thus the advantages specific to this embodiment, that is, provision of sleep with better quality to a treatment patient can be further improved as compared with the other types of CPAP devices (the types other than the servo-type automatic control auxiliary ventilator).

The above-described servo-type automatic control auxiliary ventilator has been introduced in the market by Teijin Pharma Limited with the product name of "AutoSet (Trade Mark) CS" in 2007.

The above-described "AutoSet (Trade Mark) CS" have the technical features of the configuration thereof covered by patents, patent applications or the like in countries cited below by using abbreviations: AU 691200, AU 697652, AU 702820, AU 709279, AU 724589, AU 730844, AU 731800, AU 736723, AU 734771, AU 750095, AU 750761, AU 756622, AU 761189, AU 2002306200, CA 2263126, EP 0661071, EP 1318307, JP 3635097, JP 3737698, NZ 527088, U.S. Pat. Nos. 4,944,310, 5,199,424, 5,245,995, 5,522,382, 5,704,345, 6,029,665, 6,138,675, 6,152,129, 6,240,921, 6,279,569, 6,363,933, 6,367,474, 6,398,739, 6,425,395, 6,502,572, 6,532,959, 6,591,834, 6,659,101, 6,945,248, 6,951,217, 7,004,908, 7,040,317, 7,077,132.

[Embodiment of the Invention Relating to a Testing Device Used for Titration of Respiratory Assisting Device]

Next, an embodiment of the invention relating to a testing device, which is an embodiment of the present invention described above and is effective in use for titration of the respiratory assisting device including CPAP will be described.

The titration of the respiratory assisting device is a work performed by a medical staff to determine an appropriate pressure (treatment pressure) of the respiratory assisting device such as CPAP, and detailed description is made in the information "Kobe Kyodo Hospital—Sleep Apnea Syndrome", accessibly placed on the World Wide Web http://homepage3.nifty.com/SAS-kyo/titration.pdf#search="titration".

There has been a method (manual titration: manual pressure adjustment) in which an operating pressure of the respiratory assisting device is started from the minimum pressure while sleep polygraphy (PSG) test is being conducted throughout the night, the operating pressure is adjusted while the respiration state is observed, and the pressure is manually changed so as to be raised/lowered so that apnea, hypopnea and snoring are resolved each time apnea or hypoxia state is observed, and the minimum pressure at which the sleep state of the patient becomes favorable and respiratory disorder is resolved in the end is the optimal pressure (treatment pressure). This method is a work requiring remarkable labor of observation throughout the night, and there is also a method of auto-titration in which the human labor is saved by using an Auto-CPAP device, that is, a device which automatically changes and records the pressure.

Also, other than the methods of performing the titration work for a subject in sleep as a target as above, there is a method in which a medical equipment such as a respiratory assisting device assumed to be used is attached to a subject in arousal and adequateness of the medical device for the subject or setting conditions are determined through trial use for a short time.

In the following description, not only the titration work for the subject in sleep but also the titration work for the subject in arousal as above are collectively referred to as "titration" and described.

The present invention realizes improvement in accuracy and work efficiency of the titration work more favorably adapted to the physiology of human bodies, and specifically, the operating pressure of the respiratory assisting device supplied to a subject in sleep or arousal is manually or automatically changed and a temporal change of the operating pressure is recorded, and also, the respiratory waveform of the subject is continuously recorded, and a temporal change of the waveform of the above-described RSI is created and recorded.

The operating pressure and the temporal change of RSI may be observed by a medical staff who performs the titration on a real time basis so as to be used for diagnosis, or the waveforms may be recorded or the waveform may be created later on the basis of the recorded data so that they are displayed on a monitor device, printed by a printer device or transmitted to the outside.

The medical staff compares the operating pressure changing waveform and the RSI waveform which can be simultaneously observed and by changing the operating pressure every 5 minutes, for example, if the RSI waveform changing in accordance with that has the maximum value, the medical staff can determine the operating pressure at that time as the appropriate treatment pressure. This is because the behavior of a respiratory operation cycle of a human body is directly governed by the brain center and there are few disturbance elements, and the effect of pressure application by the respiratory assisting device can be observed more directly as compared with the observation of other physiological information or heart rate, for example, and thus, the accuracy of titration can be further improved.

In addition, the medical staff can determine appropriate device for the treatment from at least any of (1) pressure value of compressed air; (2) change pattern of the pressure value of compressed air; and (3) selection of a device from a plurality of respiratory assisting devices, that is, a CPAP device, a Bi-level PAP device, an ASV (servo-type automatic control auxiliary ventilator) and the like described above.

Also, since the behavior of the respiratory cycle is observed, appropriate titration can be made also by means of observation during arousal not only in sleep, and titration can be completed in a short time during outpatient treatment without requiring hospitalization or home-visit treatment at patient's home, and thus, a burden on the patient can be reduced and medical economic effects can be improved.

The titration according to the present invention is effective not only for the CPAP but also for various respiratory assisting devices which feed out pressurized air or other respiratory gases under spontaneous respiration of the patient but the above-described titration using the prior-art technologies is effective only for measurement for titration, and if a change occurs in the symptom, the patient needs to be hospitalized again, and the titration should be performed again.

On the contrary, by performing the titration according to the embodiment of the present invention as described above, the quality of sleep or comfort level can be directly evaluated, and thus, the titration can be arbitrarily performed by the switching operation initiated by the patient himself at desired timing such as change in the symptom not only in the hospital but also at home, for example, so that an optimal condition according to the symptom can be found and automatically set.

[Embodiment of the Invention Relating to Sleep Inducing Device]

Next, an example in which the present invention is adapted to a sleep inducing device with the purpose of realizing favorable sleep by inducing an insomniac or a healthy person into a sleep state will be described as another embodiment of the present invention.

In this type of sleep inducing device, as described in Japanese patent No. 3868326, for example, sound is emitted from a loudspeaker for a patient who is going to sleep and by analyzing the contents of an operation of the patient who operated a joy stick in response to the sound, emitted sound is selected and controlled so that the patent can go to sleep as soon as possible.

Also, Japanese Patent Laid-Open No. 2003-199831 discloses a device which emits ultrasonic waves from a loudspeaker incorporated in a pillow and by sequentially changing the mode of the ultrasonic waves over time, the target is first made to feel relaxed and then, gradually induced to sleep.

However, according to these prior-art technological configurations, though some physical stimulation such as sound or ultrasonic waves is given to the target, the physical stimulation is determined in advance as a program or selected by estimating progress of sleep from an operation of the target who has not fallen asleep yet, and a mode of an optimal physical stimulation is not selected by using feedback control while the comfort level including state of sleep or the quality of sleep of the target is directly evaluated.

Figure 35:
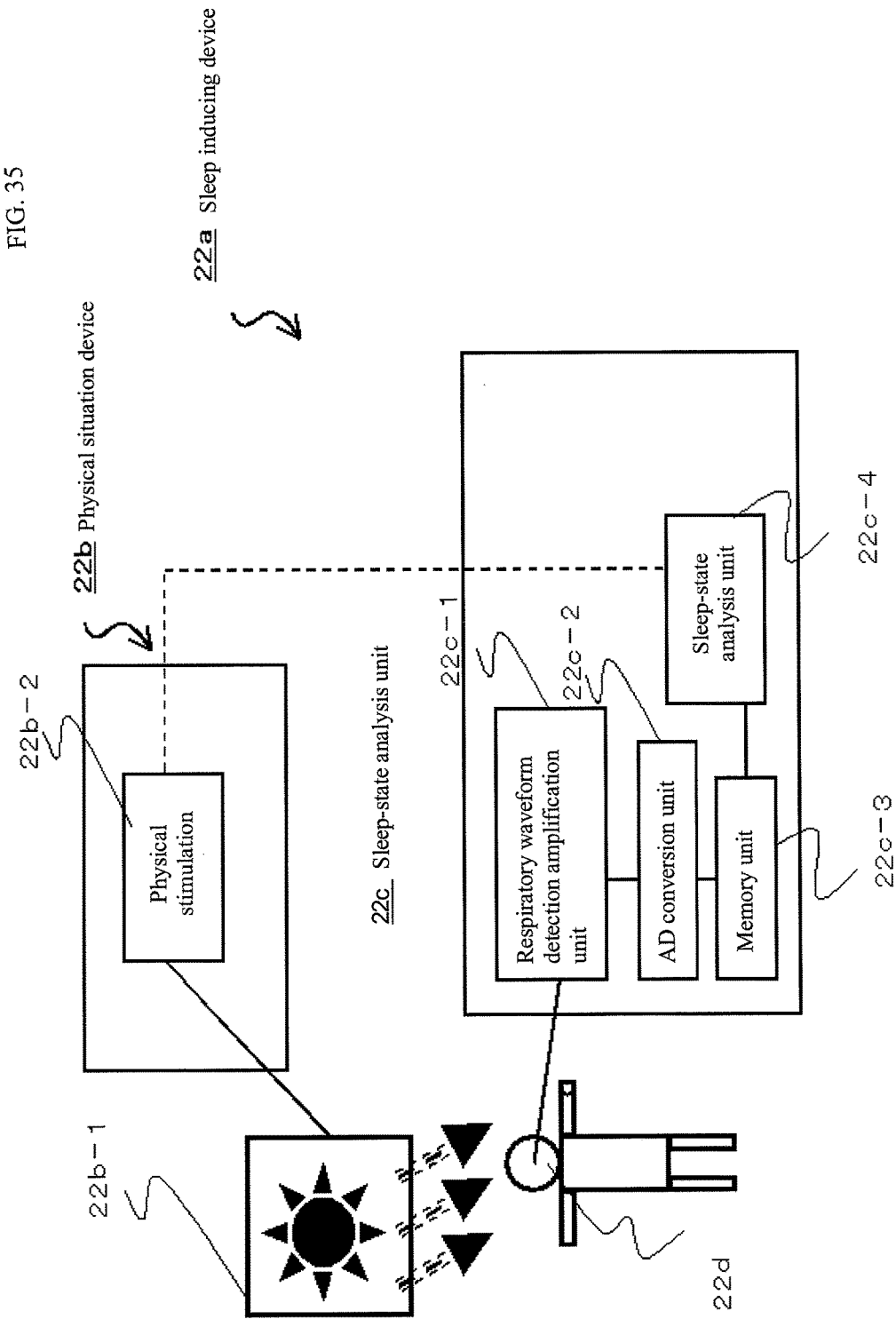
FIG. 35 is a configuration diagram of a sleep introducing device according to the present invention.

On the contrary, a sleep inducing device $22a$ of this embodiment has the following configuration exemplified in FIG. 35.

First, a physical stimulation device $22b$ is configured to give some physical stimulation such as light, sound, ultrasonic waves, heat, wind, images, smell, contact stimulation, electric stimulation, magnetic stimulation or the like from an output unit $22b$-1 to a target who is going to sleep, and the mode of the physical stimulation can be changed by a function of a physical stimulation control unit $22b$-2. For example, if the physical stimulation is light, the intensity, wavelength (color), presence or interval of flashing, area, shape or position of a light emitting body or moreover, even presence of light emission can be changed.

If the physical stimulation is sound, its intensity, wavelength (musical pitch), sound emitting pattern or interval, sound emitting direction or position or moreover, even presence of sound emitting can be changed.

A respiratory sensor $22d$ has a configuration similar to the respiratory sensor in the above-described sleep evaluation system 1.

A sleep-state analysis unit $22c$ is provided separately from or integrally with the physical stimulation device $22b$, and has a respiratory waveform detection amplification unit $22c$-1 which receives and amplifies the output of the respiratory sensor $22d$, an AD conversion unit $22c$-2 which digitalizes the analog output, a memory portion $22c$-3 which accumulates information of the digitalized waveform so as to be made accessible, and a sleep-state analysis unit $22c$-4 which will be described below.

The sleep-state analysis unit $22c$-4 can obtain a digitalized signal of a detected waveform inputted from the respiratory sensor $22d$ as described above, sequentially execute Fourier transform in the Fourier window period and create an extraction signal of the respiratory frequency band and a temporal change of the above-described RSI, for example, obtained from that on a real time basis.

Therefore, the analysis part is configured to control the operation conditions of the sleep inducing device $22a$ by watching the temporal change of the RSI and the like so that the comfort level including the quality of sleep is further improved.

[Embodiment of the Invention Relating to Massaging Device]

Next, an example in which the present invention is adapted for a massaging device which automatically performs a massaging operation with a mechanical attachment unit for the target will be described as another embodiment of the present invention.

As this type of massaging devices, Japanese Patent Laid-Open No. 2007-89716 discloses a massaging device of a parallel-link mechanism type in which movement of a treatment element is controlled stably and with good reproducibility in the vertical direction, right and left width directions, and advance/retreat direction independently with respect to a human body so that a desired massaging motion can be made by the treatment element.

Also, Japanese Patent Laid-Open No. 2003-310679 discloses a foot massager comprising a foot pressing bag having a lined unit for calf that is formed substantially into the shape of a boot so as to be brought into close contact with a calf, a heal, and a toe at the same time and having a joint unit capable of being opened/closed so as to be opened when a leg is inserted from the toe; an air filling bag body bonded to the substantially whole surface of a skin material of the foot pressing bag 2; an air pump which supplies and discharges air to and from the air filling bag body; and a connection pipe which connects an air supply/discharge hole provided in the air filling bag body and the air pump.

However, according to these prior-art technological configurations, the massaging pattern is determined in advance as a program or is selected on the basis of subjective comfort or discomfort of the massage target, and an optimal massaging pattern is not selected by using feedback control while the physiological state of the target is directly evaluated.

Figure 36:
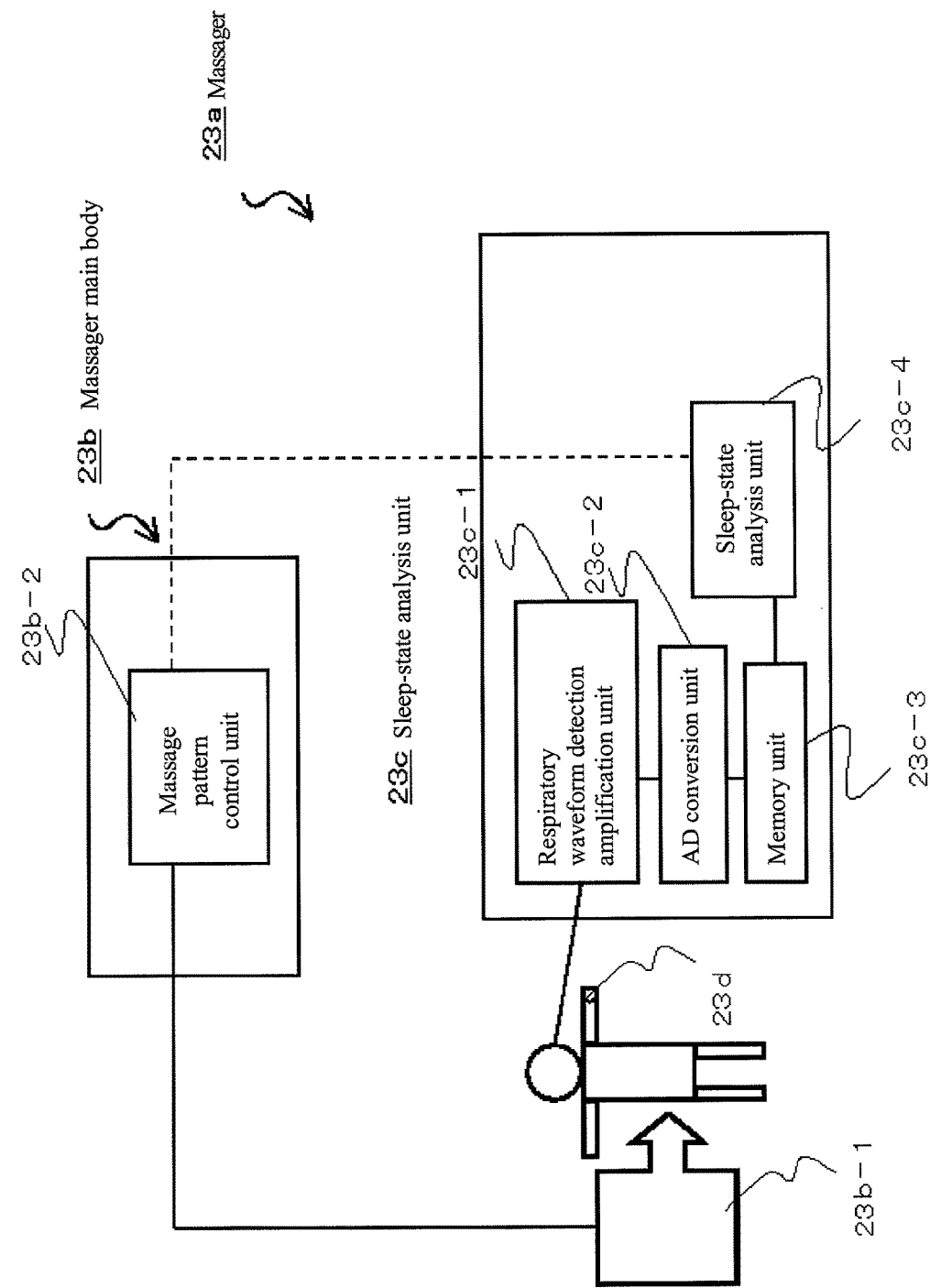
FIG. 36 is a configuration diagram of a massaging device according to the present invention.

On the contrary, a massager 23a, which is this embodiment, has the following configuration as exemplified in FIG. 36.

First, a massager main body 23b has a massage stimulation unit 23b-1 and a massaging pattern control unit 23b-2.

The massage stimulation unit 23b-1 has a configuration for performing the massaging operation by using attachments such as a roller, a hand, an air cuff and the like for the massage target, and specifically, the attachments similar to those of known massaging devices can be used.

The massaging pattern control unit 23b-2 changes and controls the mode of massage performed by the massage stimulation unit 23b-1 and controls all the operations including presence of a massaging operation, strength and patterns of the massage and the like.

The respiratory sensor 23b has the configuration which has been already described.

The sleep-state analysis unit 23c is provided separately from or integrally with the physical stimulation device 23b and has a respiratory waveform detection amplification unit 23c-1 which receives and amplifies an output of a pulse oximeter 23d, an AD conversion unit 23c-2 which digitalizes the analog output, a memory unit 23c-3 which accumulates information of the digitalized waveform so as to be made accessible, and a sleep-state analysis unit 23c-4, which will be described below.

The sleep-state analysis unit 23c-4 can obtain the digitalized signal of the detected waveform inputted from the respiratory sensor 23d as described above, sequentially execute Fourier transform in the Fourier window period, and create an extraction signal of the respiratory frequency band and a temporal change of the above-described RSI, for example, obtained from that on a real time basis.

Therefore, the analysis part is configured to control the operation conditions of the massager 23a by watching the change of the RSI and the like so that the comfort level including the quality of sleep is further improved.

[Embodiment of the Invention Relating to Blood-Pressure Measurement System]

Next, an example in which the present invention is adapted for a blood-pressure measurement system for measuring a blood pressure of a subject with favorable reliability and reproducibility and in a simplified mode will be described as another embodiment of the present invention.

According to a guideline relating to diagnosis and treatment of circulatory diseases by Kazuyuki Shimada, et al., joint research report in 1998-1999 "Guideline relating to use standard of 24-hour blood pressure meter (ABPM)" (Japanese Circulation Journal Vol. 64, Suppl. V, 2000. Hereinafter referred to as "Guideline"), a blood pressure value of a human body fluctuates under various conditions such as during activities, at rest, in sleep and the like, and it is known that these blood pressures are not necessarily correlated with casual blood pressure in an examination room.

As also indicated in the above Guideline, a 24-hour blood-pressure measurement method (ambulatory blood pressure monitoring: ABPM method) is used for measurement of a blood pressure value of a hypertensive patient.

1) If the blood pressure in an examination room or at home substantially fluctuates;

2) White coat hypertension (blood pressure is normal in a daily life but hypertension is presented in a medical environment with good reproducibility and repeatedly) is suspected;

3) Drug-refractory hypertension

4) Indication of hypotension during administration of antihypertensive drugs; and 5) Hypertension is indicated early in the morning.

The ABPM method is roughly a method for conducting blood pressure measurement during a period including sleep typically with intervals of 15 to 30 minutes by attaching a blood pressure meter to a subject.

Evaluation of night blood pressure is possible only by this ABPM method.

Reliability and accuracy of the blood pressure value measured at night is described in the Guideline as follows:

"The night sleep blood pressure can be measured only by the ABPM method. The term "night" includes a physiological state of sleep. However, the night blood pressure does not necessarily match sleep blood pressure. Also, the blood pressure is different depending on the sleep phase based on the brain waves such that the blood pressure is the lowest in the slow-wave sleep phase (deep sleep) and large blood-pressure fluctuation is found in the REM sleep. Therefore, even at night, if an arousal time domain is long, the night blood pressure is considerably higher than genuine sleep pressure.

Particularly, elderly people often wake up for night urination, and this should be considered in evaluation. Also, since the ABPM method is conducted by using upper-arm cuff pressurization, those who take the ABPM method for the first time might be aroused or have shallow sleep and have the blood pressure raised due to the pressurization, and particularly, patients with sleep disorder are reported to be aroused during cuff pressurization and have the blood pressure is increased (14/4 mmHg).

Since the night blood pressure fluctuates by sleep depth, its reproducibility is not necessarily satisfactory. Thus, a method is proposed in which circadian blood pressure is divided into two phases of square waves of daytime blood pressure (BP high) and night blood pressure (BP low), and the night blood pressure (BP min) is estimated with favorable reproducibility by a method of calculating optimal two-phase square waves (square wave fit) and a cumulative addition (cumulative sums) method. Tochikubo et al. propose stochastic "basal blood pressure value" at night derived from the correlation equation of between heart rate and blood pressure and the minimum heart rate."

That is, in the case of the blood pressure of a subject in sleep (at night), the depth of sleep affects the measured value.

Thus, for the propose of measuring the basal blood pressure value of the subject with favorable reproducibility, in order to measure the blood pressure value of the subject in a deep sleep state of the non-REM period, the period of the slow wave sleep (non-REM sleep) of the subject is diagnosed and specified from the change of the above-described brain wave SWA waveforms, by using a large-scale testing device such as a polysomnography test (PSG test) performed during hospitalization as described above, for example, and the measured value of blood pressure during the slow wave sleep period may be employed, or the blood pressure measuring device may be controlled so as to perform the blood pressure measurement operation upon knowing that the subject is in the slow wave sleep period at present. By configuring as above, the blood pressure value can be stably measured after medically confirming that the subject is in the slow wave sleep state on the basis of the physiological data of the subject.

However, the PSG test requires hospitalization as described above and is not a test performed by the subject, sleeping at home, without a burden.

Also, various methods are proposed in which the basal blood pressure value at night is estimated from statistical methods but the blood pressure value of the subject in the basal state cannot be directly measured in the first place.

With the blood-pressure measurement system 24a according to this embodiment of the present invention, by paying attention to the above-described index indicating stability of the respiratory cycle or RSI, for example, the blood pressure value of the subject in the non-REM period can be directly measured by a simplified method that can be conducted at home without requiring hospitalization.

Figure 37:
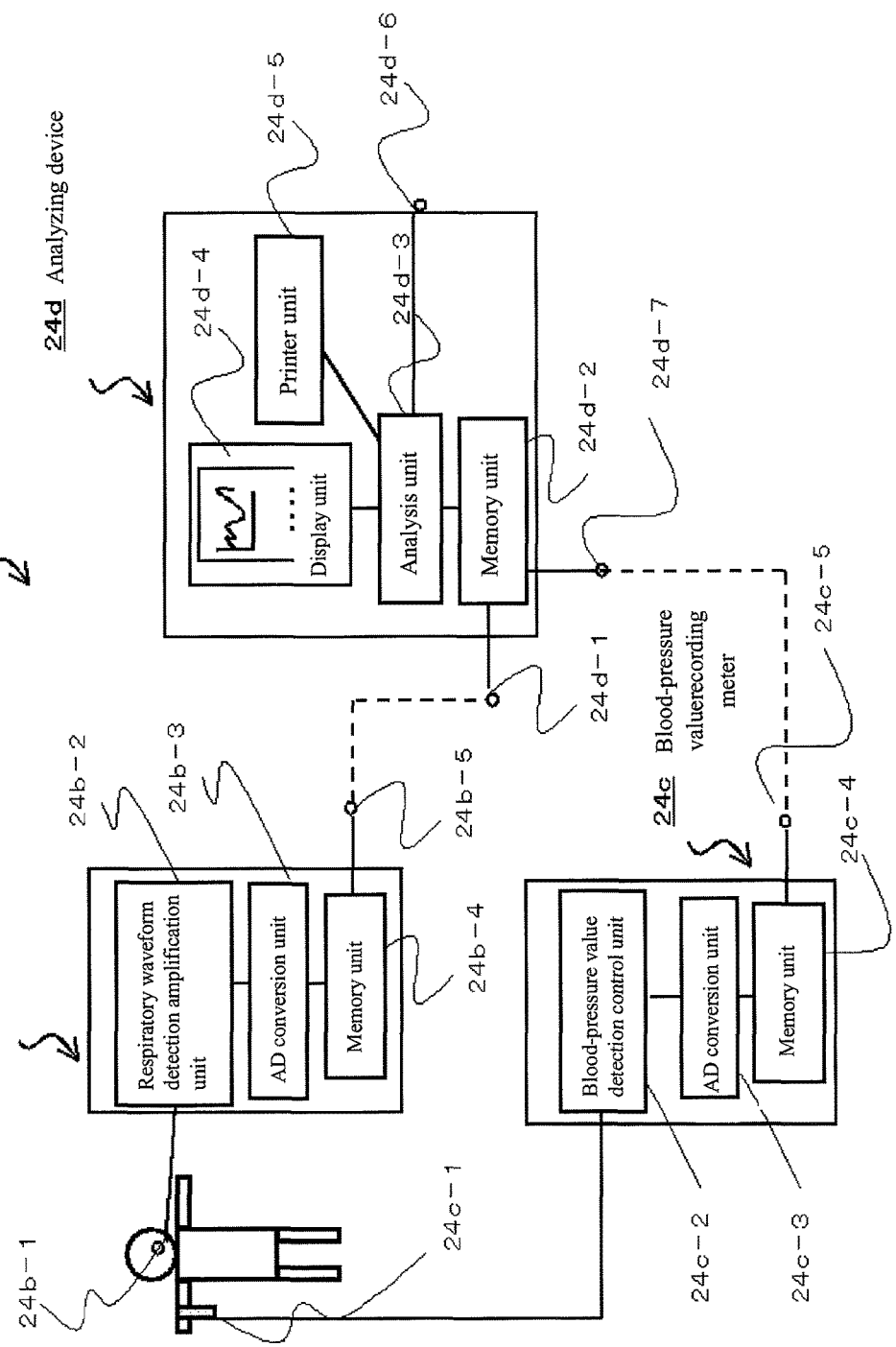
FIG. 37 is a configuration diagram of a blood-pressure measurement system according to the present invention.

By referring to FIG. 37, the configuration of the blood-pressure measurement system 24a of this embodiment will be described. This system 24a is provided with a respiratory waveform recording meter 24b which may be configured to be portable, a blood pressure value recording meter 24c which may be also configured to be portable, and an analyzing device 24d which is realized by a personal computer or the like.

The respiratory waveform recording meter 24b is preferably a device which can record the respiratory wave meter and can be also configured to be portable and is typically lent by a medical institution to a subject so that the subject can continuously record and maintain the recorded waveforms in sleep for one night at home and the recorded waveforms are conveyed to the medical institution after that.

It is needless to say that the recording of the respiratory waveforms may be recorded in the medical institution or the data of the recorded waveforms may be conducted in a flash memory or the like and transported or delivered via a communication path to a device for performing analysis, that is, the analyzing device 24d.

In order to realize the above-described functions, the respiratory waveform recording meter 24d has a respiratory airflow sensor 24b-1 attached to the skin surface in the vicinity of the nasal cavity of the subject, a respiratory waveform detection amplification unit 24b-2, an A/D conversion unit 24b-3, a memory unit 24b-4 which records and maintains the respiratory waveform as a digital signal, and an output terminal 24b-5 which outputs the digital respiratory waveform data from the memory unit 24b-4 to the outside.

The respiratory airflow sensor 24b-1 may be a thermal sensor which is attached to the vicinity of the nasal cavity of the subject and measures presence or intensity of the airflow by respiration of this subject by making measurement and detection after discriminating the temperature of the respiratory airflow and the other outside air temperature, or may be a method of resistance change caused by deformation of a strip-shaped member by the respiratory airflow, a method using rotation of a wind-mill structure by the airflow or any other types as long as the presence and intensity of the respiratory airflow can be detected, for example.

Particularly, use of a pressure-sensing respiratory sensor provided with a PVDF (polyvinylidene fluoride) piezoelectric film is a preferable mode as a pressure sensor which detects respiration.

Moreover, the respiratory operation (ventilation motion) of the subject may be measured and recorded not by directly measuring the respiratory airflow but by measuring tension caused by extension of a band wrapped around the chest or stomach of the subject by the respiratory motion or by providing a pressure-sensing sensor in a mat laid below the subject.

These various respiratory sensors are attached to a predetermined part of a patient in order to detect the respiratory airflow of the patient or respiratory efforts (ventilation motion) of the patient, and the medical institution should give guidance on the attachment method to the patient prior to the test. However, as compared with attachment of an electrode for measurement of electrocardiogram at a specific position on the epidermis on the chest of the patient, allowance in the position, direction and the like to attach the respiratory sensor is larger than the case of a sensor for electrocardiogram, and it is easy for a patient or the patient's family to attach the sensor in compliance with the guidance by the medical institution and to obtain a correct measured value.

Moreover, in recent years, instead of detection of a respiratory operation by attaching some sensing means to a subject as above, many types of a non-contact respiratory sensor have been proposed which emits electromagnetic waves to the subject from a distant position and detects the body motion or respiratory operation of the subject by analyzing reflection waves.

As described in the above embodiment, it is needless to say that as a respiratory sensor, a sensor for detecting a respiratory operation on the basis of the analysis result of the reflection waves from the subject of the irradiated electromagnetic waves such as those disclosed in the document "Microwave respiratory sensor for evaluation", which is posted on the World Wide Web and can be accessed (http://www3.ocn.ne.jp/mwlhp/kokyu.PDF), Japanese Unexamined Patent Application Publication No. 2002-71825, which is also a known document and disclosed as "human body detecting device using microwave", Japanese Unexamined Patent Application Publication No. 2005-237569, which is also a known document, and Japanese Unexamined Patent Application Publication No. 2005-270570, which is a known document and disclosed as "biological information monitoring device".

Also, the blood pressure value recording meter 24c of this system 24a is a device which measures the blood pressure of a subject and can be configured on the basis of the measurement principle similar to that of the known automatic blood pressure meter including the device used in the above-described 24-hour blood pressure measurement method (ABPM).

Specific measurement principle is that the following indirect stethoscopic blood pressure measurement method is automated.

That is, a cuff is attached to the upper arm or the like of the subject, the cuff pressure is applied to approximately a median value of the blood pressure predicted from the state of the subject or approximately 100 mmHg (millimeter of mercury), for example, and it is confirmed that Korotkoff sounds can be heard. If the Korotkoff sounds are heard, the cuff pressure is raised until it is not heard and then, the cuff pressure is slowly lowered while the display is watched. The first pulsation sound to be heard is the Korotkoff sounds first phase, and by reading the scale at this point of time, the maximal blood pressure is obtained. Then, the sound which suddenly becomes to be heard clearly indicates the second phase. The tone changes again, which indicates the third phase. The point of time when the Korotkoff sounds are no longer heard indicates the minimal blood pressure.

In order to conduct measurement on the basis of this principle, the blood pressure value recording meter 24c is provided with a cuff 24c-1. The cuff 224c-1 is provided with a cuff unit which applies a pressure to the upper arm or the like and a sound sensor unit (microphone) for auscultation.

The cuff 24c-1 may be configured not only by a microphone (KM) method in which a manual auscultation method is replaced by a microphone and a blood pressure is measured by automatically determining blood vessel sounds (Korotkoff sounds) as described above but also by an oscillometric (OS) method in which the blood pressure is measured by analyzing a pressure pulsation (oscillation) caused by pulse pressure of the cuff pressure or any other alternative methods.

Also, the blood pressure value detection control unit 24c-2 executes pressure control of the cuff pressurization, hearing and analysis of the Korotkoff sounds, all the pressurization control on the basis of the analyzed Korotkoff sounds and acquirement and feeding-out of the blood pressure value measured by the above procedures in order to have the cuff 24c-1 perform the above-described operations.

The measurement of the blood pressure value is continuously made over a period including sleep at night. The time interval of blood pressure measurement is typically 15 to 30 minutes.

The AD conversion unit 24c-3 converts the obtained blood pressure value in analog value to a digital signal and the memory unit 24c-4 has an interface function of temporarily storing the digitalized blood pressure value and sending it out to the outside. The sending of the digital blood pressure value data to the analyzing device 24d may be made via a communication path or by a method of delivery of a medium in which the data is stored in a portable memory medium and the medium is attached.

The analyzing device 24d which similarly constitutes this blood-pressure measurement system 24a is realized by a personal computer system typically including a display screen and a printer and a computer program which is installed in the computer and performs the operation, and the analyzing device is installed in a medical institution or the like, in which respiratory waveform data and the blood pressure value data from the subject are transmitted or the medium is delivered as described above, and in accordance with the procedures which will be described later, the calculation using the respiratory waveform data is made. Moreover, the respiratory waveforms, a (temporal) change of the waveform which is the result of calculation on the basis of the respiratory waveforms, and a change of the blood pressure value to be compared with the respiratory waveform change are displayed on the display screen in a time series, printed by a printer or the both are performed, and as a result, a medical staff who observes the screen display or the printed result can make diagnosis of the basal blood pressure value.

The analyzing device 24d which realizes these functions is provided with an input terminal 24d-1 which takes in digital data of the respiratory waveform from the outside, an input terminal 24d-7 which takes in digital data of the blood pressure value similarly from the outside, a memory unit 24d-2 which records and maintains the taken-in data once, an analysis unit 24d-3 which reads out the recorded data and performs a calculation operation using that as will be described later, a display unit 24d-4 which displays a respiratory cycle stability index, which is the result of calculation outputted form the analysis unit 24d-3 or time-series data such as the blood pressure value changing waveform on a display screen, a printer unit 24d-5 which prints the similarly outputted time-series data, and a data sending-out terminal 24d-6 which sends out the time-series data to the outside.

[Operation of Analyzing Device]

Subsequently, the operations such as calculation of the respiratory waveform, comparable output of the blood pressure value and the like performed by the analyzing device 24d, which is a characteristic configuration of this system 24a, will be described.

The above-described analysis unit 24d-3 provided in the analyzing device 24d extracts the above-described respiratory operation cyclic waveform, mean lung power, for example, as a respiratory cycle band from the respiratory waveforms obtained by measurement in accordance with the principle similar to the sleep evaluating device 1 on the basis of the respiratory waveform described by using FIG. 1, firstly calculates an average value (X bar) of the respiratory frequency and further calculates the standard deviation (SD) of the respiratory frequency by using a known statistical method so that the size of fluctuation of the respiratory cycle can be known. Moreover, by taking an inverse number of this standard deviation (SD), stability of the respiratory cycle can be indicated.

Instead of using the average value (X bar) of the respiratory frequency, other indexes such as the above-described respiratory cycle peak frequency (Respiration Stability Index) may be used.

Similarly to the above-described other embodiments, the inverse number of the standard deviation of the measured respiratory waveform is referred to as RSI (Respiration Stability Index). By forming a graph of this RSI so that a temporal change in sleep for one night can be known, medical staff observing the graph can easily judge whether the sleep cycle is clearly indicated and the comfort level including the quality of sleep is good or the sleep cycle cannot be observed and the comfort level including the quality of sleep is poor. Also, in the RSI changing waveform in which the sleep cycle can be clearly observed, it can be detected that, in the time domain in which the value of RSI is large, the subject is in the non-REM period at present, that is, in a deep sleep state.

Figure 38:
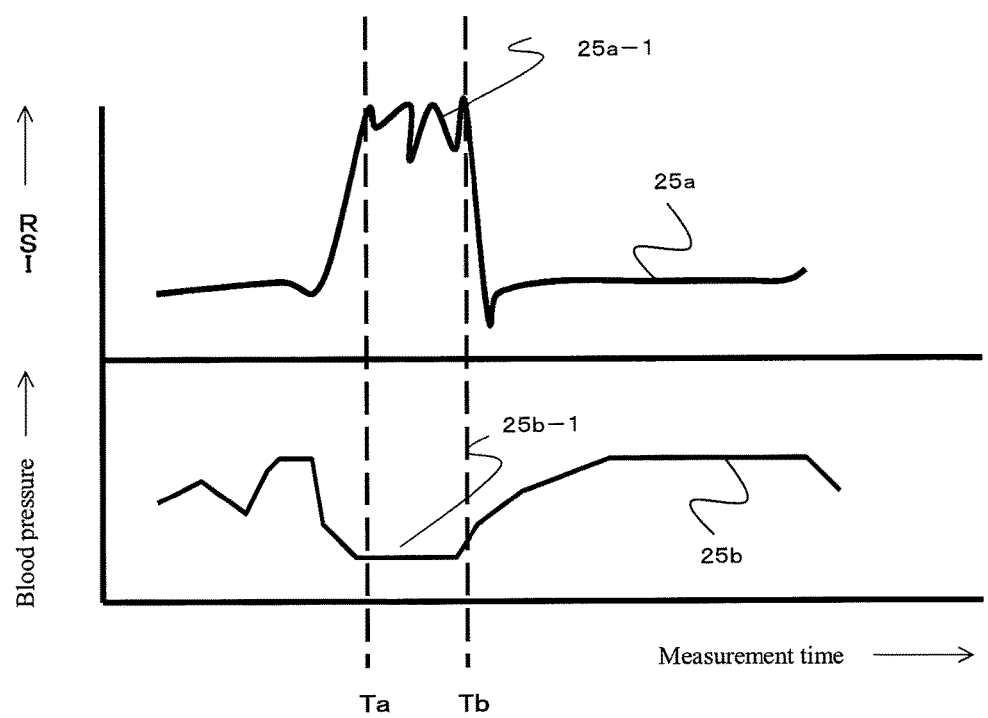
FIG. 38 is a schematic diagram of a graph outputted by the system in FIG. 37.

In FIG. 38 schematically explaining the graph outputted by this system 24a in the form of display, print and the like, the lateral axis indicates measurement time of the physiological data of the subject, and the vertical axis indicates the sizes of the RSI and the blood pressure value.

The RSI and the blood pressure value are displayed by superimposing them vertically by using the same measurement time for the two kinds of physiological data so that the RSI and the blood pressure value for the same time can be observed for comparison.

The observer who saw the graph illustrated in FIG. 38 first observes an RSI changing waveform 25a identifies the time domain with large RSI (Ta to Tb, 25a-1 in FIG. 38) and understands that the subject is in a deep sleep state in this domain.

Subsequently, the observer observes a blood pressure value changing waveform 25b-1 in Ta to Tb at the same time in the blood pressure value changing waveform 25b and can determine that the low blood pressure value in this domain should be employed as the basal blood pressure.

As a result, without using large-scale testing equipment such as PSG or without relying on indirect means such as statistical means, the blood pressure value of the subject in the deep sleep state can be obtained, and the basal blood pressure can be measured with favorable reproducibility, high accuracy and ease.

Thus, in the system of the present invention, as already described, from a plurality of Fourier spectrums at the time which becomes a start point of each Fourier window period obtained by executing fast Fourier transform (FFT) by shifting time by 5 seconds for the Fourier window period of 5 minutes from the inputted respiratory waveform, a frequency domain of 0.11 to 0.50 Hz including 0.4 Hz, which is a typical respiratory cycle of a human body is extracted. Moreover, in the system of the variation of the present invention, the analysis portion 24d-3 calculates the average value (X bar) and the standard deviation (SD) of the frequency included in the respiratory frequency band for each Fourier window obtained with the shifting interval of 50 seconds. And it is so configured that the above-described RSI is calculated from the inverse number of the standard deviation and displayed in a mode in which comparison can be made with the blood pressure value.

The respiratory waveform and the blood pressure value are preferably measured in parallel at the same time, but if they share a period when they match each other, it is only necessary to configure that the data of the both can be compared and evaluated in the matched period, and the measurement periods of the both may be different.

Also, the system may be used such that the respiratory waveform and the blood pressure value are continuously measured by the above-described method for the subject not only in the sleep state at night but in arousal and the blood pressure value is measured when the RSI is large, that is, when the physiological state of the subject is in a stable period.

The configurations of these embodiments may be expanded and the same also applied to the following variations.

[Variation of Blood-Pressure Measurement System]

In the above-described embodiment, the blood pressure measurement is described to be made continuously during the sleep of a subject with typical measurement intervals of 15 to 30 minutes similarly to the ABPM method.

The automatic blood pressure meter makes blood pressure measurement by pressurizing and tightening a cuff on the upper arm of the subject, and it is likely that the measurement awakes the subject.

Thus, as a variation of the above-described embodiment of the present invention, instead of continuous blood pressure measurement for a subject in sleep, it may be so configured that the blood pressure measurement by using cuff pressurization is performed only when the RSI exceeds a pre-set threshold value and in a deep sleep state.

Alternatively, though the blood pressure measurement is made continuously in the sleep of the subject, it may be so configured that storage of the measured blood pressure value data to a memory, information transmission or output such as display is executed only if the RSI exceeds a pre-set threshold value. By configuring as above, memory capacity can be reduced, communication error risk in information transmission can be decreased, and work efficiency in observation by an observer of the waveform data can be improved.

Since the configurations of these variations are the same as the blood-pressure measurement system 24a described above except the above-described difference, the description will not be repeated here in order to avoid cumbersomeness.

[Application of the Present Invention to Polysomnography Test (PSG Test)]

The blood-pressure measurement system described above has an advantage that an operation at home is easy on the basis of the respiratory waveform which can be measured easily since the slow wave sleep state is known from the change of the RSI, for example, as an index of stability of a respiratory cycle so that the basal blood pressure value can be detected.

In putting the present invention into practice, the index and physiological data to know presence of the slow wave sleep state are not limited to the respiratory waveforms and the index of RSI obtained therefrom.

For example, as described above, medical staff can diagnose the depth of the sleep, that is, presence of the slow wave sleep from the change of the brain wave SWA waveforms, and thus, it may be so configured that by continuously measuring the brain waveforms and the blood pressure values in parallel for a period including sleep, the medical staff specifies a time domain in which the subject is in the slow wave sleep state based on the change of the brain waveforms or particularly, the brain wave SWA waveforms and employs the measured blood pressure value in that domain as a basal blood pressure value.

Alternatively, the blood pressure measurement system may be so configured that the brain waveforms of a subject is continuously measured over a predetermined period including sleep and the power of the brain wave SWA waveform, which is a component obtained by extracting the low-frequency region, for example, is continuously monitored, and if the power of the brain wave SWA waveforms exceed the pre-set threshold value, it is determined that the subject is in the slow wave sleep state at present, and the measuring device automatically directs execution of measurement of the blood pressure value so that the blood pressure value in the slow wave sleep region, that is, the basal blood pressure value can be automatically measured.

Moreover, as the physiological data for detecting the slow wave sleep state of the subject, a single or a plural pieces of physiological data other than the brain waveforms may be employed, these plural pieces of physiological data are continuously measured and displayed, respectively, or the device may be configured to automatically determine the presence of the slow wave sleep by a predetermined condition under which these plural pieces of physiological data are combined.

Since sleep can also be considered as a physiological and functional state of the brain, by using a configuration in which the brain waveforms are used for measurement, for example, the state of the brain itself can be observed and the basal blood pressure value can be measured and determined as confirmed diagnosis.

As a configuration which can be a basis of such embodiment of the present invention, a polysomnography testing device (PSG testing device) which has been used for detecting a slow wave sleep state of a subject will be described below.

The PSG testing device is a testing device which quantitatively calculates depth of sleep (sleep stage), fragmentation of sleep, presence of arousal reaction, sleep organization, sleep efficiency and the like along with details of a respiratory state by measuring more detailed biological information from brain waves, electromyogram, motion of eye balls and the like in addition to basic items such as a respiratory airflow, snoring sound, arterial oxygen saturation ($SpO_2$) and the like.

In order to conduct the PSG test, a patient is hospitalized in a medical institution or a dedicated test facility called sleep lab, attached with various sensors belonging to a testing instrument called a sleep polygraphy measurement recording device (hereinafter referred to as a PSG testing device) to body parts of the patient and goes to sleep. During the sleep, output signals from each of the sensors are continuously recorded in a predetermined recording medium (a hard disk of a personal computer, a memory card and the like).

The recorded data is analyzed in a manual analysis in which medical staff directly analyzes the test data or using a dedicated device called sleep polygraphy automatic analyzer. In the case of the automatic analysis, a report collecting evaluations of a plurality of items is automatically created. The plurality of evaluation items include the following items, for example:

TABLE 2

"Examples of PSG measurement and items"

| Measurement | Evaluation |
| --- | --- |
| Brain wave | Type and depth of sleep, arousal |
| Eye movement | Presence of REM sleep |
| Mental electromyogram | Presence of REM sleep |
| Respiration (thermistor) | Presence of airflow in mouth/nose |
| Ventilation | Detection of ventilation in chest and abdomen |
| Electrocardiogram | Arrhythmia and heart rate change |
| Arterial oxygen saturation | Grasping of hypoxia |
| Body posture | Dorsal posture often increases generation frequency of apnea |
| Inferior limb electromyogram | Presence of restless legs syndrome |

Product examples of the PSG testing device include "Sleep Watcher E Series" (marketing authorization holder Teijin Pharma Limited, Medical equipment authorization No. 21400BZY00026000, management medical equipment class, specified maintenance and management medical equipment).

This "Sleep Watcher E Series" is designed based on a brainwave meter and can measure up to 55 channels at the maximum and display fine waveform with a high sampling rate (512 Hz at the maximum) and A/D resolution of 14 bits. A pulse oximeter and a pressure sensor are built in the main body, and such advantages are provided that an operation is easy in a simple design, various testing environments can be handled through LAN, and the system is expandable. The system can be easily expanded to a two-bed system through a HUB and can handle digital video image input (optional). The system is capable of operations in Japanese, and easy to understand, so that work efficiency of test/diagnosis is improved, and various analysis results can be freely laid out including report layouts in a rich text.

Also, the "Sleep Watcher E Series" is capable of handling the following data as input test channels, that is, physiological data to be measured:

AC electrode (brainwave sleep diagnosis channel): 32 ch
AC input (respiration, limb motion channel): 8 ch
DC input (posture and other channels): 4 ch
Oximeter: 1 ch
Pressure sensor: 2 ch
External DC input (optional): 8 ch These prior-art PSG testing devices do not include the blood pressure value in the physiological data to be measured.

The stage determination of the sleep brainwaves is made on the basis of polygraph finding in which brainwave (EEG), eye movement (EOG), mental electromyogram (EMG) and the like are combined. As a determination standard for sleep stages, an international standard (Rechtshaffen & Kales, 1968) is set.

Therefore, it can be so configured that, by newly using the blood pressure value as the measurement target physiological data of a subject in sleep in addition to the measurement target physiological data of the prior-art PSG testing device as above, medical staff can comprehensively analyze the plural pieces of physiological data, specify the blood pressure value in the slow wave sleep and determine the basal blood pressure value.

Alternatively, it may be so configured that the device automatically determines the presence of the slow wave sleep under a predetermined condition by using one or a combination of a plurality of the physiological data, and performs output such as display, print or transmission of presence of the slow wave sleep and the measured blood pressure value to the outside so that they are contrasted with each other.

Alternatively, it may be so configured that measurement of the blood pressure value of the subject is performed when the presence of the slow wave sleep is automatically determined by the device.

Since specific configurations of these embodiments of the present invention are obvious from the configuration of the above-described other embodiments of the present invention and the configuration of the PSG testing device, the description will not be repeated in order to avoid cumbersomeness.

[Application of the Present Invention to Oxygen Concentrator]

Subsequently, as another aspect of the present invention, an embodiment of an oxygen supply device of the present invention which evaluates the physiological state of a human body or particularly, a comfort level by using stability of a respiratory cycle and the like will be described by referring to the attached drawings.

Figure 39:
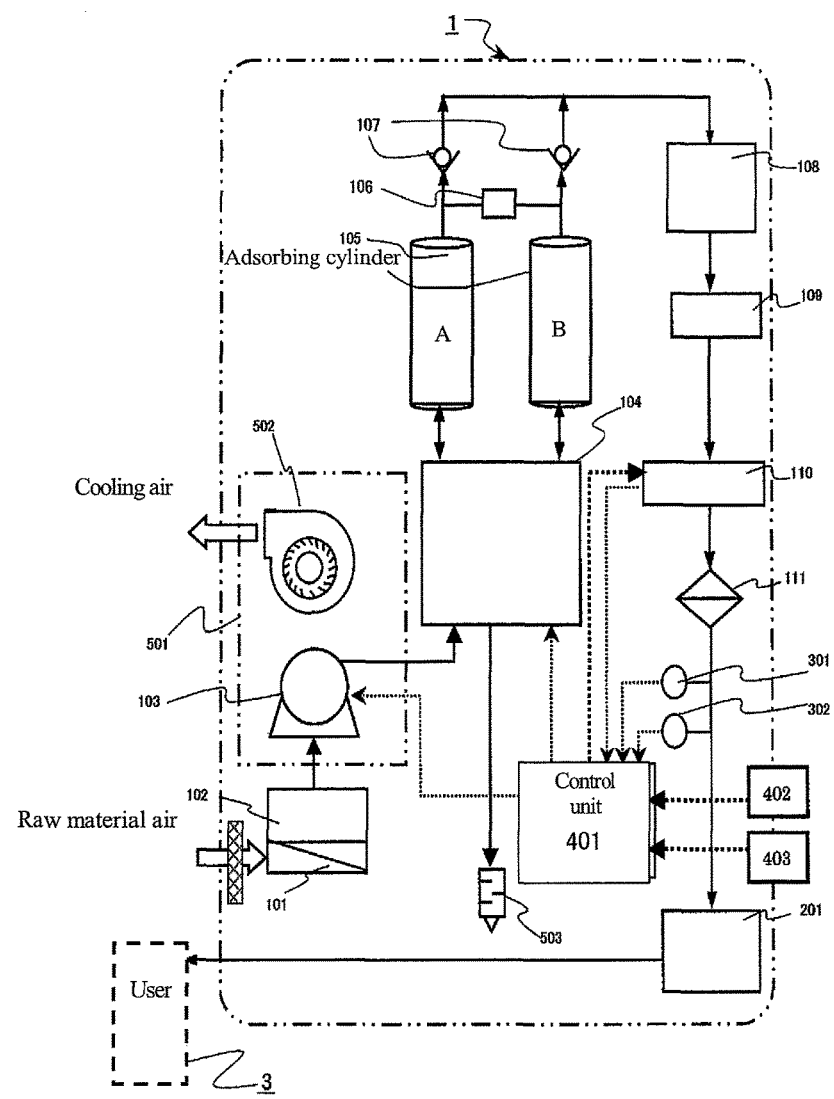
FIG. 39 is an outline device configuration diagram exemplifying a pressure-variable adsorption type oxygen concentrating device, which is an embodiment of the present invention.

FIG. 39 is a schematic diagram of a device configuration exemplifying a pressure-variable adsorption-type oxygen concentrator, which is an embodiment of the present invention.

An oxygen concentrator 1 of this embodiment is provided with a respiration synchronization unit 201 which detects at least either of inspiration or expiration of a patient and a control unit 401 as its characteristic configuration. The respiration synchronization unit 201 exerts a function of reducing a power amount required for the operation of the oxygen concentrator and of reducing the size of the configuration of the oxygen concentrator used in the prior-art technologies as they are by supplying oxygen concentrated gas only during the inspiration period of the patient and also exerts a function of creating respiratory waveform information of the patient by using the detection function of the inspiration and expiration. The control unit 401 calculates an index of respiratory cycle stability called RSI, which was described above, from the obtained respiratory waveform information, continuously monitors a change of this RSI and controls change of a supply flow of oxygen concentrated gas by changing an opening of a control valve 110 which controls a flow of the oxygen concentrated gas for intake in a direction to a state in which the RSI becomes a higher value, that is, the comfort level of the patient is improved. As a result, according to this embodiment, the optimal oxygen gas amount in accordance with the actual physiological state of the patient can be supplied more precisely and since addition of the new function to the oxygen concentrator needs mainly a change of an operation control program of the oxygen concentrator, the new sophisticated function can be added while the device remains simple and requiring only a low cost without requiring large-scaled addition of mechanisms or electronically controlled components.

The oxygen concentrator 1 of this embodiment including a part overlapped with an oxygen concentrator having a respiration synchronization function according to the prior-art technology will be described below.

In FIG. 39, which is an outline configuration diagram of this embodiment, reference numeral 1 denotes an oxygen concentrator and reference numeral 3 denotes a user (patient) who inspires humidified oxygen enriched air (also referred to as "oxygen concentrated gas"). The pressure-fluctuation adsorption-type oxygen concentrator 1 is provided with an HEPA filter 101 which removes fine dusts having passed through an air filter provided at a raw material air inlet, an inspiration silencer 102, a compressor 103, a channel switching valve 104, an adsorption cylinder 105, a check valve 107, a product tank 108, a pressure control valve 109, flow setting means 110, and a particle filter 111. As a result, oxygen concentrated gas in which oxygen gas is concentrated can be manufactured from the raw material air taken in from the outside.

Also, in a housing of the oxygen concentrator, a humidifier (not shown) which humidifies the produced oxygen concentrated gas, the control part 401 which controls the compressor and the channel switching valve 104 by using a set value of the flow setting means 110 and measured values of an oxygen concentration sensor 301 and a flow sensor 302, a compressor box 501 which isolates noise of the compressor, and a cooling fan 502 which cools the compressor are built in.

First, the raw material air taken in from the outside is taken in through the air inlet provided with the outside air inlet filter 101 which removes foreign substances such as dusts and the inspiration silencer 102. At this time, approximately 21% of oxygen gas, approximately 77% of nitrogen gas, 0.8% of argon gas, and 1.2% of carbon dioxide and other gases are contained in the normal air. In such a device, only the oxygen gas is concentrated and taken out as a gas for respiration.

This taking-out of the oxygen gas is performed by sequentially switching the target adsorption cylinder by the channel switching valve 104 among the adsorption cylinders in which is filled adsorbent made of zeolite and the like which selectively adsorb nitrogen gas molecules rather than the oxygen gas molecules in the raw material air while supplying the raw material air by pressurizing the same by the compressor 103, and by selectively adsorbing and removing approximately 77% of the nitrogen gas contained in the raw material air in the adsorption cylinder.

As such adsorption cylinders, a multiple-cylinder type formed of a cylindrical container filled with the absorbent and usually having three cylinders or more is used in addition to single-cylinder and double-cylinder types, but in order to manufacture oxygen enriched air from the raw material air continuously and efficiently, a multiple-cylinder type adsorption cylinders are preferably used. Also, as the compressor, a swing-type air compressor is used, and rotation-type air compressors including a screw type, a rotary type, a scroll type and the like are also used in some cases. A power supply of a motor which drives this compressor may be AC or DC.

The oxygen concentrated gas mainly composed of the oxygen gas not adsorbed in the adsorption cylinder 105 flows into the product tank 108 through the check valve 107 provided to prevent backflow into the adsorption cylinder.

Also, the nitrogen gas adsorbed by the adsorbent filled in the adsorption cylinder needs to be desorbed from the absorbent in order to adsorb the nitrogen gas again from the newly introduced raw material air. Thus, the pressurized state realized by the compressor is switched by the channel switching valve to a reduced-pressure state (an atmospheric pressure state or negative pressure state, for example), and the adsorbed nitrogen gas is desorbed so as to regenerate the adsorbent. In this desorption step, in order to improve the desorption efficiency, the oxygen concentrated gas may be made to backflow as a purge gas from the product end side of the adsorption cylinder during the adsorption process or from the product tank.

Since a large airflow sound is usually generated in desorption of the nitrogen, a nitrogen exhaust noise silencer 503 is generally used.

The oxygen concentrated gas produced from the raw material air is accumulated in the product tank 108. The oxygen concentrated gas accumulated in the product tank contains oxygen gas with high concentration of 95%, for example, and is supplied to the humidifier (not shown) while the supply flow and pressure thereof are controlled by the pressure control valve 109 and the flow setting means 110, and the humidified oxygen concentrated gas is supplied to the patient. Such humidifiers include a non-water supply type humidifier which takes in moisture from the outside air by a moisture permeable membrane module having a moisture permeable membrane and supplies it to the oxygen concentrated gas in a dried state, a bubbling-type humidifier using water as a humidification source, or a surface-evaporation type humidifier can be used.

As the flow setting means 110, a control valve is used. If a first mode in which a supply flow of the oxygen concentrated gas is manually set is selected, the opening of the control valve is controlled by the control portion 401 through an up/down button 402 of the oxygen supply flow provided in the oxygen concentrator, and the flow is changed to a predetermined flow. Other than this first flow setting mode, as a second flow setting mode, which is a characteristic of the present invention, the supply flow rate of the oxygen concentrated gas can be controlled, by monitoring the stability of the respiratory cycle included in the respiratory waveform information which is one type of biological information, in the direction in which the comfort level of the patient is improved, wherein the comfort level can be evaluated based on the stability of the respiratory cycle. The above-described two modes can be selected and operated by a patient or a helper of the patient by a selection operation of a mode selection switch 403.

The respiration synchronization part 201 is a major constituent element of this second flow setting mode and a major element in realizing the respiration synchronization function which realizes reduction of a power amount required for the operation of the oxygen concentrator, size reduction of the configuration of the oxygen concentrator and the like by supplying the oxygen concentrated gas only during the inspiration period of the patient. The respiration synchronization function will be described first.

A highly sensitive pressure sensor (a semiconductor pressure sensor, for example) arranged in the respiration synchronization unit 201 detects a slight negative pressure when the patient inspires the oxygen concentrated gas through a duct called cannula, and the control unit 401 makes control of opening/closing of the control valve 110 so that the oxygen concentrated gas is supplied for the whole period or a partial period of inspiration in the respiration cycle of the patient on the basis of the signal outputted from this sensor. This embodiment is configured so that the control valve 110 also works as a so-called on/off valve, but a control valve which determines a flow and a switching valve which switches shut-off/flow of the gas can be configured separately.

In general, inspiration occupies ⅓ and expiration occupies ⅔ of time in the respiration cycle of a human being, and by supplying the oxygen concentrated gas with a high flow on a continuous basis for the whole period or a partial period of this inspiration period, the oxygen concentration gas is supplied only when the patient actually inspires oxygen. Also, since the supply of the oxygen concentrated gas is stopped for the expiration period, the amount of the oxygen concentrated gas to be supplied to the patient is saved (conserved), and as a result, the operation power amount is reduced, and the same oxygen gas supply can be performed with a smaller-sized oxygen concentrator configuration.

As described above, the respiration synchronization unit 201 is provided with a pressure sensor inside and can detect inspiration/expiration timing of the patient and as a result, create the respiratory waveform information.

Then, in the oxygen concentrator 1 of this embodiment, by examining the respiratory cycle of the patient from the respiratory waveform information obtained as above, calculating the stability as RSI, for example, described above, and continuously recording the change of the RSI, the control unit 401 can detect the physiological stability or comfort level of the patient and how it changes.

If the second supply flow setting mode is selected, the control unit 401 continuously monitors the change of the RSI and changes the opening of the control valve 110 so that the RSI becomes a higher value, that is, the comfort level of the patient is improved and controls the change of the supply flow of the oxygen concentrated gas.

For each patient, a doctor determines the oxygen supply amount of the oxygen treatment as prescription, but the oxygen amount physiologically required by a human body is different depending on the activity state of the human body and other situations, and the prescribed flows are determined by the doctor with different values for the exertion period (when activities are high), the rest period, and the sleep period, respectively, for example, but according to this embodiment, the optimal oxygen gas amount is supplied in accordance with the actual physiological state of the patient more finely.

Also, this embodiment is particularly useful when a patient walks while pulling a portable oxygen concentrator for going to hospital or performing a walking exercise (rehabilitation).

It is needless to say that such control of the supply amount should be made under instructions and control of doctors.

Also, according to this embodiment, since a respiratory pressure sensor which the respiration synchronization type oxygen concentrator is already equipped with is used, further configuration for measuring the respiratory waveform is not needed, and the configuration of the oxygen concentrator becomes simple and inexpensive, which is an advantage.

This embodiment is capable of many variations being put into practice other than the above-described modes, and they also correspond to embodiments of the present invention.

For example, other than the oxygen concentrator, application to an oxygen gas cylinder or a device which supplies oxygen for inspiration from a liquid oxygen bottle is possible, and any application is possible as long as continuous measurement of various types of physiological data such as heart rate, cardiogram, brain waves, body temperature, oxygen saturation in blood, respiration volume, walking speed, blood pressure value and the like other than the respiratory waveform can be made and the physiological state or comfort level of a human body can be evaluated.

Also, as a sensor for obtaining the respiratory waveforms, other than the pressure sensor for the respiration synchronization function, an airflow sensor, a temperature sensor, a sound sensor and the like may be used.

[Application of the Present Invention to Medical Equipment Monitoring System and Telemedicine System]

Next, an example in which the present invention is applied to a medical equipment monitoring system which transmits operation information and the like of various types of medical equipment or particularly an oxygen concentrator installed at patient's home to a remote monitoring center or a telemedicine system which transmits/receives physiological data will be described on the basis of the attached drawings.

A remote system which transmits measured physiological data (vital data) of a patient such as blood pressure, body temperature, respiratory frequency, oxygen saturation in blood and the like to a reception terminal via a communication path or a so-called telemedicine system has been used for remote diagnosis or a state observation of a patient.

However, transmission of physiological stability or an index of comfort level of a patient, instead of such direct physiological data, to a reception terminal via a communication path or creation of the physiological stability or an index of comfort level of the patient on the basis of the physiological data received via the communication path has not been known or proposed, either.

A system such as the Teijin Oxygen-concentrator Monitoring System (TOMS)® operated by Teijin Pharma Limited, the applicant of this application, in which an operation state of a medical equipment used by a patient at home or the like is monitored by a monitoring center is proposed and actually utilized. A configuration in which a function of transmitting physiological data of a patient such as oxygen saturation in blood, for example, is given to the operation monitoring of a medical equipment so that the state of the patient can be observed by the monitoring center is also proposed. However, not such transmission/reception and use of the direct physiological data but transmission of the physiological stability or an index of comfort level of the patient to a reception terminal via a communication path or creation of the physiological stability or an index of comfort level of the patient on the basis of the physiological data received via the communication path has not been known or proposed, either.

This embodiment is configured such that an index of physiological stability or comfort level of a patient as exemplified by RSI, which is an index of the above-described respiratory cycle stability or the physiological data used for creating this index can be transmitted.

If a monitoring center or a medical staff grasps such physiological stability or comfort level of a patient, applications become possible wherein a state of the patient which cannot be known from simple measured values of the physiological data, the change of the state and effects of the treatment conducted at home of the patient such as an at-home oxygen treatment can be confirmed, preventive maintenance is made possible by trend observation before the state actually deteriorates, and the like.

Figure 40:
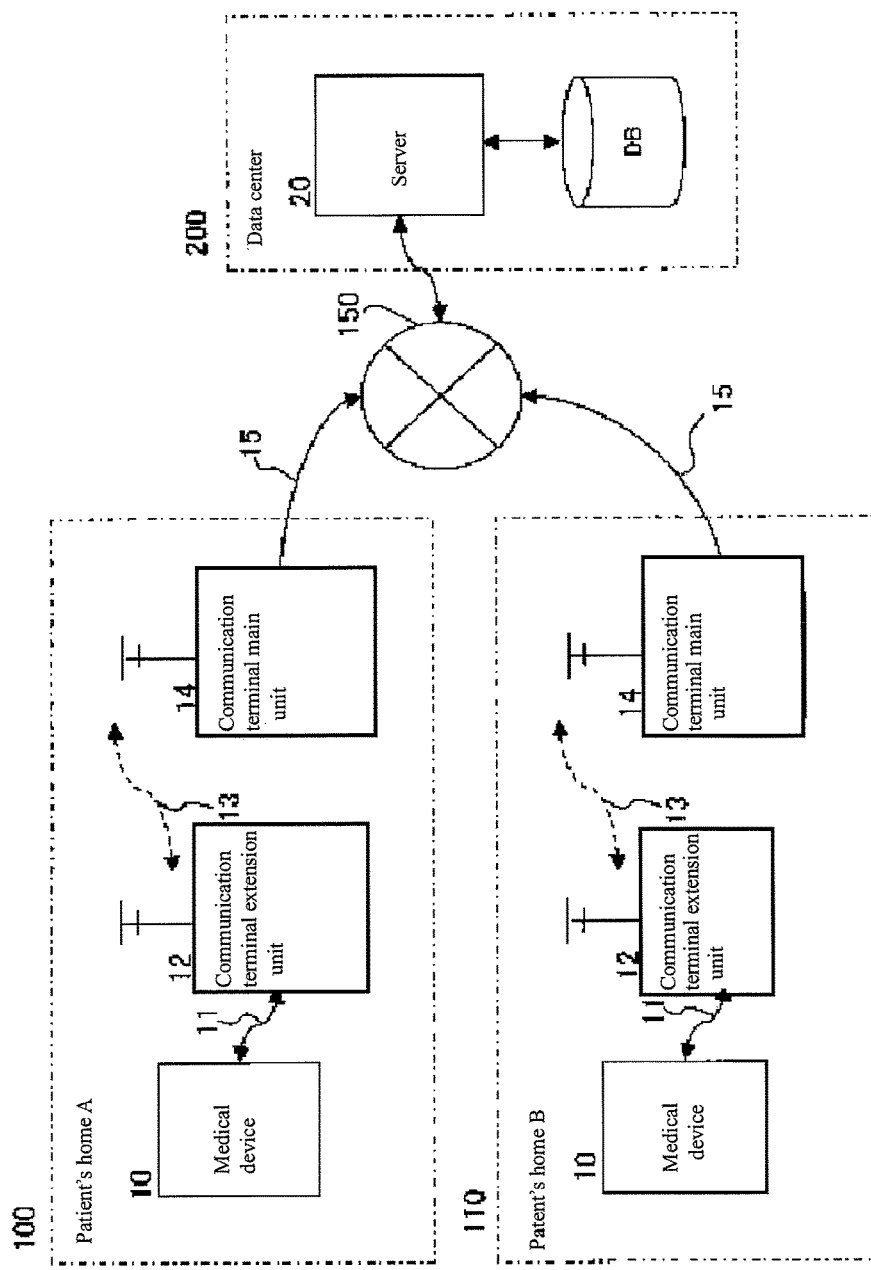
FIG. 40 is a diagram illustrating an example of a medical support system in this embodiment.

FIG. 40 is a diagram illustrating an example of a medical support system in this embodiment.

In putting this embodiment into practice, it is needless to say that, without limiting to the configuration in which information such as RSI is put into the monitoring system of medical equipment operation information as illustrated in FIG. 40, the system may be configured mainly for transmitting physiological data as the prior-art telemedicine system or various index values created from the physiological data. These systems are configured in such a way that the respiratory waveform information of the patient is obtained by measurement methods of airflow, temperature change, movement of chest or abdomen, body motion during sleep, change of the gravity center position and the like and the respiratory waveform information is sent via a communication path or converted to RSI before the transmission and the RSI is transmitted via the communication path.

In FIG. 40, which is an example in which the invention is applied to a monitoring system of the medical equipment operation information, in patient locations 100 and 110 including a patient's home, elderly people's home, children's welfare facility, medical institution where patients are hospitalized or go for treatment and the like, a medical equipment 10 such as a medical oxygen concentrator described above used for at-home treatment, a communication terminal extension unit 12 connected to the medical equipment 10 through a communication cable 11 or the like, and a communication terminal main unit 14 capable of information communication with the communication terminal extension unit 12 via a wireless communication medium or a wired communication medium 13 or the like are installed. The communication terminal main unit 14 uploads information to a server 20 in a data center 200 located far from the medical device 10 through a public communication network such as a public telephone line 150. Into the server 20 in the data center, a database DB which stores information of medical equipment and patients and the operation information of the medical equipment is connected. This server 20 might be installed at a remote location from the patient's home or at a location far from the medical equipment in the medical institution.

The communication terminal extension unit 12 might be housed in a housing of the medical equipment 10 and connected through a communication connecting member. The communication terminal main unit 14 is connected to the public communication network 150 by connecting a telephone line cable 15 to a modular jack of a telephone installed in the patient's home. Thus, the communication terminal main unit 14 shares the public communication network 150 with the communication equipment such as an installed telephone set at the patient's home.

In the normal state, the oxygen concentrator, which is the medical equipment 10, concentrates oxygen in the air and generates highly concentrated oxygen gas with the concentration of 90%, for example, and the patient inhales oxygen in compliance with the prescription by a doctor. The medical equipment 10 creates operation information including when, for how long and how much the oxygen was supplied, for example, and outputs the information to the communication terminal extension unit 12. Then, the communication terminal main unit 14 obtains this operation information and uploads it to the server 20 at preset upload timing. This upload timing is uniquely determined for each of the plurality of medical equipment with a cycle of once in 24 hours, for example. By determining the upload timing for each of the plurality of medical equipment, concentrated uploading to the server is avoided. Also, since the communication terminal main unit 14 shares the public communication network 150 with the communication equipment at the patient's home, the upload timing is set to time zones at night.

The medical equipment 10 creates emergency information if abnormality occurs. For example, the abnormality includes a case in which the value of oxygen concentration or oxygen flow becomes abnormal or each component of the medical equipment departs from a steady state or the like. The emergency information is supplied to the communication terminal main unit 14 via the communication terminal extension unit 12. Then, the communication terminal main unit 14 uploads the emergency information to the server 20 on a real time basis without waiting for the upload timing.

The operation of transmission/reception of the operation information of the medical equipment in this medical equipment monitoring system has so far been described. As described above, the respiratory waveform information of the patient can be obtained from the pressure sensor of the respiration synchronization part of the oxygen concentrator or other sensor means. From this respiratory waveform information, information of the stability of the respiratory cycle or RSI, for example, can be created as described above. Since RSI and the like are indexes indicating the comfort level of the patient, real-time monitoring of the RSI of a patient at home at a remote location and accumulating and recording the information in the server 20 by using this medical support system is extremely effective in observing the state of the patient, predicting deterioration of the state, checking the treatment effects of the oxygen treatment and the like.

Thus, this embodiment system is configured to transmit the information such as RSI and the like in addition to the medical equipment operation information such as oxygen concentrator from the medical equipment side to the server side. The medical equipment is not limited to the oxygen concentrator but any type of medical equipment which uses information such as RSI.

Various configurations can be conceived for the system, and it is possible to transmit the respiratory waveform information to the server so that the server can create the RSI or to create and transmit the RSI on the medical equipment side or to transmit the information if the RSI exceeds a specific threshold value.

The description of this embodiment is only one aspect, and the number of the communication terminal main/extension units may be one terminal or may be built in the medical equipment.

Also, it is needless to say that the communication path for transmitting the information may be a mobile phone line or the information may be delivered to the server using a recording medium such as an USB memory.

Alternatively, information on how the RSI has changed and how much the supply flow rate of the oxygen concentrated gas was at that time and the like for a certain period like one week or one day may be gathered into a journal data of a report format in writing or on a screen so that medical staff and the like can make an access.

INDUSTRIAL APPLICABILITY

According to the present invention, a calculating device of respiratory waveform information used for evaluating the comfort level including the quality of sleep and detecting Cheyne-Stokes respiration syndrome reliably and simply without requiring hospitalized test and also, by using only the respiratory waveforms, a device for evaluating the comfort level including the quality of sleep, a calculating device of physiological data, a computer program for making calculation using the respiratory waveform information, a computer program for evaluating the comfort level including the quality of sleep of the subject, a respiratory assisting device, a treatment device for chronic heart diseases, a testing device used for titration work, a blood-pressure testing device, a computer program for conducting a blood pressure test, a polysomnography testing device and the like are provided.

REFERENCE SIGNS LIST 1 sleep evaluation system (calculating device of respiratory waveform information)
2-1 respiratory sensor (measuring means)
3-3 analysis unit (calculating means)
3-4 display unit (output means)
3-5 printer part (output means)
3-6 output end (output means)

The invention claimed is:

1. A respiratory assisting device for continuously supplying compressed air to a patient in a sleep state, the respiratory device comprising:
at least one non-transitory memory operable to store program code;
at least one processor operable to read said program code and operate as instructed by said program code to:
receive respiratory waveform data of a subject for a measurement period;
create an index at each of a plurality of measurement times during the measurement period, the index indicating stability of measured value as an inverse number of the standard deviation of respiratory frequency (RSI) at each of the plurality of measurement times during the measurement period; and
create data of a temporal RSI during the measurement period based on the index;
a blower configured to feed out compressed air with a pressure higher than an atmospheric pressure to a patient; and
a controller configured to change feeding-out pressure of the blower based on the RSI to improve the quality of sleep of the patient.

2. The device according to claim 1, further comprising: a recording meter configured to record the respiratory waveform data of the subject.

3. The device according to claim 2, wherein the information of the respiratory waveform data recorded in said recording meter is transmitted to the at least one processor via a recording medium or a communication path.

4. The device according to claim 1, wherein the data of a temporal change of the index is one or more selected from the group consisting of RSI trend, frequency distribution of RSI, RSI autocorrelation function, and change of ultradian rhythm power included in RSI trend, and the device is for calculating respiratory waveform information.

5. The device according to claim 1, wherein the measurement period is a measurement period including sleep.

6. The device according to claim 5, wherein
the at least one processor operable to read said program code and operate as instructed by said program code determines automatically a quality of sleep by comparing the created data to data where a quality of sleep is good.

7. A respiratory assisting device for continuously supplying compressed air to a patient in a sleep state, the respiratory device comprising:
creating means which create an index at each of a plurality of measurement times, wherein the index indicates stability of a measured value as an inverse number of the standard deviation of respiratory frequency (RSI) at each of the plurality of measurement times during measurement period;
air feeding means for feeding out compressed air with a pressure higher than an atmospheric pressure to a patient; and
control means for receiving the RSI and changing feeding-out pressure of the air feeding means based on the RSI to improve the quality of sleep of the patient.

* * * * *